United States Patent
Herman et al.

(10) Patent No.: US 7,772,189 B2
(45) Date of Patent: Aug. 10, 2010

(54) PHAGE DISPLAYED CELL BINDING PEPTIDES

(75) Inventors: Richard E. Herman, Redmond, WA (US); Ekaterina G. Makienko, Lynnwood, WA (US); Douglas L. Badders, Seattle, WA (US); Mark Fuller, Roslyn, WA (US)

(73) Assignee: MDRNA, Inc., Bothell, WA (US)

( * ) Notice: Subject to any disclaimer, the term of this patent is extended or adjusted under 35 U.S.C. 154(b) by 0 days.

(21) Appl. No.: 12/701,397

(22) Filed: Feb. 5, 2010

(65) Prior Publication Data

US 2010/0137225 A1 Jun. 3, 2010

Related U.S. Application Data

(62) Division of application No. 11/627,863, filed on Jan. 26, 2007.

(60) Provisional application No. 60/823,894, filed on Aug. 29, 2006, provisional application No. 60/774,496, filed on Feb. 17, 2006.

(51) Int. Cl.
*A61K 38/00* (2006.01)
*C07K 7/06* (2006.01)

(52) U.S. Cl. .......................................... 514/16; 530/329
(58) Field of Classification Search ....................... None
See application file for complete search history.

(56) References Cited

OTHER PUBLICATIONS

Kim et al. "Screening of LPS-specific peptides from a phage display library using epoxy beads", Biochemical and Biophysical Research Communications, 2005, vol. 329, No. 1, pp. 312-317.*

* cited by examiner

*Primary Examiner*—Suzanne M. Noakes
(74) *Attorney, Agent, or Firm*—Mark A. Bales; MDRNA, Inc.

(57) ABSTRACT

This disclosure provides the construction, expression, and selection of the mutated genes that encode novel Trp cage polypeptides with desirable binding properties, as well as the novel Trp cage polypeptides themselves. The substances or targets bound by these novel Trp cage polypeptides may be but need not be proteins or polypeptides. Targets may include other biological or synthetic macromolecules as well as other organic and inorganic substances. Further, targets may also include a single or multiple cell or tissue types. The present invention achieves genetic variants of Trp cage-encoding nucleic acids through controlled random mutagenesis of the nucleic acids yielding a mixture of Trp cage polypeptides that are capable of binding targets.

15 Claims, No Drawings

PHAGE DISPLAYED CELL BINDING PEPTIDES

This application is a divisional claiming the benefit under 35 U.S.C. §121 of U.S. patent application Ser. No. 11/627,863, filed Jan. 26, 2007, which claims the benefit under 35 U.S.C. §119(e) of U.S. Provisional Application Nos. 60/823,894, filed Aug. 29, 2006, and 60/774,496, filed Feb. 17, 2006, each of which is hereby incorporated by reference in its entirety.

BACKGROUND OF THE INVENTION

The delivery of nucleic acids, peptides and other pharmacological agents into animal and plant cells has been an important object of molecular biology and clinical research. A variety of methods are available for delivering nucleic acid artificially into cells. Similar delivery methods are applied to both peptides and other pharmacological agents. The most commonly used methods employ cationic lipids, electroporation and viral transduction and numerous methods that target mechanical or biochemical membrane disruption and/or penetration (e.g., using detergents, microinjection, or particle guns). However, these methods suffer from a variety of disadvantages. For example, while cationic lipids are used most often for DNA and small interfering RNAs (siRNAs) delivery in vitro, they have generally been found to be highly toxic and therefore not appropriate for in vivo delivery applications such as in the treatment of disease. With viral gene delivery, there is a possibility that the replication deficient virus used as a delivery vehicle may revert to wild-type thus becoming pathogenic. Electroporation suffers from poor gene-transfer efficiency and therefore has limited clinical application. Additionally, all of the above delivery methods as applied to patients are not cell or tissue specific resulting in the delivery of nucleic acids, peptides and other pharmacological agents to non-target tissues. This is a highly inefficient means of delivery and subjects a patient's organs and tissues to unneeded metabolic stress.

Alternative methods of delivery included synthetic and biological polypeptides. These delivery methods show great potential as a tool to introduce nucleic acids peptides and other pharmacological agents into cells. However, the repertoire of known polypeptides capable of efficiently delivering pharmacological agents to cells is limited. Moreover, the current state of technology for delivery peptides is still in its infancy and there are no known cell or tissue specific delivery polypeptides.

Thus, there remains a long-standing need in the art for better tools and methods to deliver nucleic acids, peptides and other pharmacological agents into cells, particularly in view of the fact that existing techniques for delivering substances into cells are limited by poor efficiency and/or high toxicity of the delivery reagents. Related needs exist for improved methods and formulations to deliver an effective amount, in an active and enduring state, and using non-toxic delivery vehicles, to selected cells, tissues, or compartments to mediate regulation of gene expression in a manner that will alter a phenotype or disease state of the targeted cells.

BRIEF SUMMARY OF INVENTION

One aspect of the invention is a Trp cage binding domain polypeptide comprised of all or part of amino acid sequence

AAADX$_1$YX$_2$QWLX$_3$X$_4$X$_5$GPX$_6$SGRPPPX$_7$,    (SEQ ID NO: 4)

wherein X$_n$ represents an amino acid found in position n. In one embodiment, the polypeptide binds to human endothelial cells, for example, the polypeptide comprising an amino acid sequence selected from the group consisting of SEQ ID NO: 447 to SEQ ID NO: 529. In an alternate embodiment, the polypeptide binds to human epithelial cells, e.g., human hepatic cells, for example the polypeptide comprising an amino acid sequence selected from the group consisting of SEQ ID NO: 201 to SEQ ID NO: 368. In another embodiment, the polypeptide binds to a protein or a glycan on the surface of a human cell. In another embodiment, the polypeptide conjugates or complexes with a biologically active agent, preferably a drug, e.g., a siRNA molecule. In another embodiment, the polypeptide conjugates or complexes with a fusogenic peptide, e.g., PN73, having the structure SEQ ID NO: 552
NH2-KGSKKAVTKAQKKDGKKRKRSRKESYSVYVYKVLKQ-amide Another aspect of the invention is a cell binding domain polypeptide comprising an amino acid sequence selected from the group consisting of SEQ ID NO: 31 to SEQ ID NO: 529. In one embodiment, the polypeptide binds to human endothelial cells, for example, the polypeptide comprising an amino acid sequence selected from the group consisting of SEQ ID NO: 369 to SEQ ID NO: 529. In an alternate embodiment, the polypeptide binds to human epithelial cells, e.g., human hepatic cells, for example the polypeptide comprising an amino acid sequence selected from the group consisting of SEQ ID NO: 31 to SEQ ID NO: 368, most specifically, NLQEFLF (SEQ ID NO: 61). In another embodiment, the polypeptide binds to a protein or a glycan on the surface of a human cell. In another embodiment, the polypeptide conjugates or complexes with a biologically active agent, preferably a drug, e.g., a siRNA molecule. In another embodiment, the polypeptide conjugates or complexes with a fusogenic peptide, e.g., PN73.

Another aspect of the invention is a method of using a cell binding domain polypeptide for delivery of a drug to a specific tissue, wherein the polypeptide has an amino acid sequence selected from the group consisting of SEQ ID NO: 31 to SEQ ID NO: 529. In one embodiment, the polypeptide binds to a specific cell type within the tissue. In another embodiment, the polypeptide is administered intravenously, or to the lung, or by injection.

DESCRIPTION OF THE INVENTION

Phage display is widely used for the screening of random combinatorial peptide libraries (panning) in drug discovery. A caveat to phage display screening methods is that peptides are typically displayed on the phage as unconstrained linear molecules. Consequently, these peptides adopt numerous conformations of which very few represent the desired binding conformation resulting in the isolation of peptides that exhibit low binding affinity to the target (e.g., cell specific binding). However, by reducing the conformational freedom of the phage displayed peptides, entropy decreases and peptide binding affinity for the target increases. By employing this approach in phage display technology, the ability to obtain novel peptides with high binding affinity to a specific target is enhanced.

Traditionally, constrained phage display libraries with reduced conformational freedom were produced by incorporating a pair of cysteine residues at both ends of linear peptides resulting in disulphide bridges that form peptide loops. These cyclic peptide libraries were reported to increase binding affinity. However, in comparison to cyclic peptide phage display libraries, folded protein scaffold phage display libraries exhibit greater potential to increase binding affinity by providing a more rigid conformation. Examples of folded protein scaffolds include the zinc finger motif, which was used to construct a degenerate library for the isolation of peptides that bind to DNA and RNA, and Kunitz domains, which were used to construct degenerate libraries for the discovery of better serine protease inhibitors.

Another protein that has potential to serve as a scaffold for the generation of a random peptide library is derived from exendin-4, a molecule isolated from the saliva of the Gila Monster (*Heloderma suspetum*). Exendin-4 has the following amino acid sequence:

HGEGTFTSDLSKQMEEEAVR-LFIEWLKNGGPSSGAPPPS (SEQ ID NO: 1).

Exendin-4 contains a highly folded region at the C-terminus consisting of a tryptophan residue surrounded by proline residues. The resulting folded structure resembles a cage and is labeled the Trp cage. The Trp cage motif was derived from the 39 amino acid residue exendin-4 polypeptide. It was shown by NMR that the last 9 amino acid residue at the C-terminus of exendin-4 form a Trp cage. The extensively studied Trp cage folds spontaneously and cooperatively faster than any known protein even though it is only 20 amino acids in length. Of these 20 amino acids, not all are required for protein folding. (See Neidigh, et al., *Biochem.* 40:13188-200, 2001; Snow, et al., *J. Am. Chem. Soc.* 124:14548-49, 2002, hereby incorporated by reference.) Thus, the substitution of amino acids at select positions with the Trp cage protein does not compromise protein folding. Further, these select positions are solvent exposed making them ideal for the display of random amino acids. By utilizing the Trp cage as a folded protein scaffold, a randomized library of high complexity displayed on the major capsid protein of bacteriophage T7 was created.

The present invention relates to the construction, expression, and selection of the mutated genes that encode novel Trp cage polypeptides with desirable binding properties, as well as the novel Trp cage polypeptides themselves. The substances or targets bound by these novel Trp cage polypeptides may be but need not be proteins or polypeptides. Targets may include other biological or synthetic macromolecules as well as other organic and inorganic substances. Further, targets may also include a single or multiple cell or tissue types. The present invention achieves genetic variants of Trp cage-encoding nucleic acids through controlled random mutagenesis of the nucleic acids yielding a mixture of Trp cage polypeptides that are capable of binding targets. It selects for novel mutated Trp cage encoding nucleic acids that encode novel Trp cage polypeptides with desirable binding properties by (1) arranging that the Trp cage polypeptide of each mutated nucleic acid be displayed on the outer surface of a microbe (a cell, spore or virus) that contains the gene, and (2) using affinity selection—selection for binding to the target material—to enrich the population of packages for those packages containing genes specifying novel Trp cage polypeptides with improved binding to that target material. Finally, enrichment is achieved by allowing only the genetic packages, which, by virtue of the displayed novel Trp cage polypeptides, bound to the target, to reproduce.

According to the present invention, a peptide library is produced using random nucleic acid sequences that encode up to about $10^9$ different Trp cage peptides. A nucleic acid sequence that can be used to produce the $10^9$ different Trp cage peptides is:

```
                                        (SEQ ID NO: 2)
5'-CA CAT GCC CCG AAT TCG GCA GCA GCA GAT NNK TAC
NNK CAG TGG TTA NNK NNK NNK GGT CCT NNK TCT GGT
CGT CCT CCC CCC NNK TAA CAA GCT TGA ACA TG-3'
```

The underlined portion of SEQ ID NO: 2 GCAGCAGCA-GATNNKTACNNKCAGTGGTTANNKNNKNNKGGTC-CTNNKTCTGGTCGTCCTCCCCCCNNK (SEQ ID NO: 3), encodes the Trp cage. For the two nucleotide sequences listed above only, K represents equal molar amounts of the nucleotides adenine (T) or cytosine (G) and N represents equal molar amounts of adenine (A), cytosine (C), thymine (T) or guanine (G).

Based on the above nucleotide sequence represented by SEQ ID NO: 3, the deduced amino acid sequence of the Trp cage is as follows:

```
                                        (SEQ ID NO: 4)
A A A D X Y X Q W L X X X G P X S G R P P P X
```

The rest of the oligonucleotide allows it to bind to the extension primer and contains flanking restriction enzyme sites to facilitate cloning. The nucleic acid sequence encoding a polypeptide comprised of SEQ ID NO: 4 would be placed in a phage-display system.

Using the above-described nucleic acid sequence, a plethora of Trp cage peptides can be produced using bacteriophage (phage) display techniques. Phage display is a technique by which non-viral polypeptides are displayed as fusion proteins on the coat protein on the surface of bacteriophage particles.

The display strategy is first perfected by modifying a nucleic acid sequence to display a stable, structured Trp cage binding domain for which a novel Trp cage polypeptide is obtainable. It is believed that a nucleic acid that encodes the polypeptide of SEQ ID NO: 4 encompasses all of the novel Trp cage polypeptides envisioned by the present invention.

Four goals guide the various variegation plans used herein, preferably: (1) a very large number (e.g. $10^9$) of variants is available, (2) a very high percentage of the possible variants actually appears in detectable amounts, (3) the frequency of appearance of the desired variants is relatively uniform, and (4) variation occurs only at a limited number of amino-acid residues, most preferably at residues having side groups directed toward a common region on the surface of the potential binding domain.

To obtain the display of a multitude of different though related potential binding domains, applicants generate a heterogeneous population of replicable microbes each of which comprises a hybrid gene including a first nucleotide sequence which encodes a potential Trp cage binding domain for the target of interest and a second nucleotide sequence which encodes a display means, such as an outer surface protein native to the microbe but not natively associated with the potential Trp cage binding domain which causes the microbe to display the corresponding chimeric protein (or a processed form thereof) on its outer surface.

Another important aspect of the invention is that each potential Trp cage binding domain remains physically associated with the particular nucleic molecule, which encodes it. Thus, once successful Trp cage binding domains are identified, one may readily recover the gene and either express additional quantities of the novel binding protein or further mutate the gene. The form that this association takes is a "replicable genetic package", a virus, cell or spore, which replicates and expresses the Trp cage binding domain-encoding gene, and transports the binding domain to its outer surface. By virtue of the present invention, novel Trp cage polypeptides are obtained that can bind specifically to targets.

In one embodiment, the invention relates to: (a) preparing a variegated population of replicable microbes, each package including a nucleic acid construct coding for an outer-surface-displayed potential binding Trp cage binding domain polypeptide, comprising (i) a structural signal directing the display of the Trp cage binding domain polypeptide on the outer surface of the package, and (ii) a potential Trp cage binding domain for binding said target, where the population collectively displays a multitude of different potential binding domains having a substantially predetermined range of variation in sequence; (b) causing the expression of said Trp cage binding domain polypeptide and the display of said Trp cage binding domain polypeptide on the outer surface of such packages; (c) contacting the microbes with target material with an exposed combining site, so that the potential binding domains of the Trp cage binding domain polypeptides and the target material may interact, and separating microbes bearing a potential Trp cage binding domain polypeptide that succeeds in binding the target material from microbes that do not so bind; (d) recovering and replicating at least one microbe bearing a successful Trp cage binding domain polypeptide; (e) determining the amino acid sequence of the successful Trp cage binding domain polypeptide of a genetic package which bound to the target material; and (f) obtaining the nucleic acid encoding the desired Trp cage binding domain polypeptide from the microbe and placing it into a suitable expression system. (The Trp cage binding domain may then be expressed as a unitary protein, or as a domain of a larger protein).

The invention likewise encompasses the procedure by which the display strategy is verified. The microbes are engineered to display a single Trp cage binding domain polypeptide binding sequence. (Variability may be introduced into nucleotide subsequences adjacent to the Trp cage binding domain subsequence and within the outer surface gene so that the Trp cage binding domain polypeptide will appear on the surface of the microbe.) A molecule, such as an antibody, having high affinity for correctly folded Trp cage binding domain polypeptide is used to: (a) detect a Trp cage binding domain polypeptide on the surface of the microbe, (b) screen colonies for display of Trp cage binding domain polypeptide on the microbe surface, or (c) select microbes that display Trp cage binding domain polypeptides from a population, some members of which might display Trp cage binding domain polypeptides on the surface of the microbe such as in one preferred embodiment, this verification process (part 1) involves: (1) choosing a microbe such as a bacterial cell, bacterial spore, or phage, having a suitable outer surface protein; (2) choosing a novel Trp cage binding domain polypeptide; (3) designing an amino acid sequence that: (a) includes the Trp cage binding domain as a subsequence, and (b) will cause the Trp cage binding domain polypeptide to appear on the surface of the genetic package; (4) engineering a vector sequence that: (a) codes for the designed Trp cage binding domain amino acid sequence, (b) provides the necessary genetic regulation, and (c) introduces convenient sites for genetic manipulation; (5) cloning the vector sequence into the microbe, and (6) harvesting the transformed microbes and testing them for presence of the Trp cage binding domain polypeptide on the surface of the microbe; this test is performed with a target molecule having high affinity for the Trp cage binding domain polypeptide.

For each target, there are a large number of Trp cage binding domain polypeptides that may be found by the method of the present invention.

Display Strategy: Displaying Foreign Binding Domains on the Surface of a Microbe A. General Requirements It is emphasized that the microbe on which selection-through-binding will be practiced must be capable, after the selection, either of growth in some suitable environment or of in vitro amplification and recovery of the encapsulated genetic message. During at least part of the growth, the increase in number is preferably approximately exponential with respect to time. The component of a population that exhibits the desired binding properties may be quite small. Once this component of the population is separated from the non-binding components, it must be possible to amplify it. Culturing viable cells is the most powerful amplification of genetic material known and is preferred. Genetic messages can also be amplified in vitro, e.g., by PCR, but this is not the most preferred method.

Preferred microbes are vegetative bacterial cells, bacterial spores and bacterial DNA viruses. Eukaryotic cells could be used as microbes but have longer dividing times and more stringent nutritional requirements than do bacteria and it is much more difficult to produce a large number of independent transformants. They are also more fragile than bacterial cells and therefore more difficult to chromatograph without damage. Eukaryotic viruses could be used instead of bacteriophage but must be propagated in eukaryotic cells and therefore suffer from some of the amplification problems mentioned above.

Nonetheless, a strain of any living cell or virus is potentially useful if the strain can be: (1) genetically altered with reasonable facility to encode a Trp cage binding domain, (2) maintained and amplified in culture, (3) manipulated to display the Trp cage binding domain where it can interact with the target material during affinity separation, and (4) affinity separated while retaining the genetic information encoding the displayed binding domain in recoverable form. Preferably, the microbe remains viable after affinity separation.

When the microbe is a bacterial cell, or a phage that is assembled periplasmically, the display means has two components. The first component is a secretion signal, which directs the initial expression product to the inner membrane of the cell (a host cell when the package is a phage). This secretion signal is cleaved off by a signal peptidase to yield a processed, mature, Trp cage binding protein. The second component is an outer surface transport signal that directs the package to assemble the processed protein into its outer surface. Preferably, this outer surface transport signal is derived from a surface protein native to the microbe.

For example, in a preferred embodiment, the hybrid gene comprises a DNA encoding a Trp cage binding domain operably linked to a signal sequence (e.g., the signal sequences of the bacterial phoA or bla genes or the signal sequence of M13 phage gene III) and to DNA encoding a coat protein (e.g., the M13 gene III or gene VIII proteins) of a filamentous phage (e.g., M13). The expression product is transported to the inner membrane (lipid bilayer) of the host cell, whereupon the signal peptide is cleaved off to leave a processed hybrid protein. The C-terminus of the coat protein-like component of this hybrid protein is trapped in the lipid bilayer, so that the hybrid protein does not escape into the periplasmic space. (This is typical of the wild-type coat protein.) As the single-stranded DNA of the nascent phage particle passes into the periplasmic space, it collects both wild-type coat protein and the hybrid protein from the lipid bilayer. The hybrid protein is thus packaged into the surface sheath of the filamentous phage, leaving the potential binding domain exposed on its outer surface. (Thus, the filamentous phage, not the host bacterial cell, is the "replicable microbe" in this embodiment.)

If a secretion signal is necessary for the display of the potential binding domain, in an especially preferred embodiment the bacterial cell in which the hybrid gene is expressed is of a "secretion-permissive" strain.

When the microbe is a bacterial spore, or a phage, such as the T7Select® phage display system from Novagen®, San Diego, Calif., whose coat is assembled intracellularly, a secretion signal directing the expression product to the inner membrane of the host bacterial cell is unnecessary. In these cases, the display means is merely the outer surface transport signal, typically a derivative of a spore or phage coat protein.

There are several methods of arranging that the Trp cage binding domain gene be expressed in such a manner that the Trp cage binding domain is displayed on the outer surface of the microbe.

The replicable genetic entity (phage or plasmid) that carries the outer surface protein-Trp cage binding domain genes (derived from the outer surface protein-Trp cage binding domain gene) through the selection-through-binding process, is referred to hereinafter as the operative cloning vector. When the operative cloning vector is a phage, it may also serve as the microbe. The choice of a microbe is dependent in part on the availability of a suitable operative cloning vector and suitable outer surface protein.

Viruses are preferred over bacterial cells and spores. The virus is preferably a DNA virus with a genome size of 2 kb to 10 kb base pairs, such as (but not limited to) the filamentous (Ff) phage M13, fd, and fl; the IncN specific phage Ike and Ifl; IncP-specific *Pseudomonas aeruginosa* phage Pf1 and Pf3; the T7 virus and the *Xanthomonas oryzae* phage Xf.

The species chosen as a microbe should have a well-characterized genetic system and strains defective in genetic recombination should be available. The chosen strain may need to be manipulated to prevent changes of its physiological state that would alter the number or type of proteins or other molecules on the cell surface during the affinity separation procedure.

Phages

In use of a phage one needs to know which segments of the outer surface protein interact to make the viral coat and which segments are not constrained by structural or functional roles. The size of the phage genome and the packaging mechanism are also important because the phage genome itself is the cloning vector. The outer surface protein-Trp cage binding domain gene is inserted into the phage genome; therefore: (1) the genome of the phage must allow introduction of the outer surface protein-binding domain gene either by tolerating additional genetic material or by having replaceable genetic material; (2) the virion must be capable of packaging the genome after accepting the insertion or substitution of genetic material, and (3) the display of the outer surface protein-binding domain protein on the phage surface must not disrupt virion structure sufficiently to interfere with phage propagation.

Bacteriophages are excellent choices because there is little or no enzymatic activity associated with intact mature phage, and because the genes are inactive outside a bacterial host, rendering the mature phage particles metabolically inert.

For a given bacteriophage, the preferred outer surface protein is usually one that is present on the phage surface in the largest number of copies, as this allows the greatest flexibility in varying the ratio of outer surface protein-Trp cage binding domain to wild type outer surface protein and also gives the highest likelihood of obtaining satisfactory affinity separation. Moreover, a protein present in only one or a few copies usually performs an essential function in morphogenesis or infection; mutating such a protein by addition or insertion is likely to result in reduction in viability of the microbe. Nevertheless, an outer surface protein such as M13 gIII protein may be an excellent choice as outer surface protein to cause display of the Trp cage binding domain.

The user must choose a site in the candidate outer surface protein gene for inserting a Trp cage binding domain gene fragment. The coats of most bacteriophage are highly ordered. Filamentous phage can be described by a helical lattice; isometric phage, by an icosahedral lattice. Each monomer of each major coat protein sits on a lattice point and makes defined interactions with each of its neighbors. Proteins that fit into the lattice by making some, but not all, of the normal lattice contacts are likely to destabilize the virion by: (a) aborting formation of the virion, (b) making the virion unstable, or (c) leaving gaps in the virion so that the nucleic acid is not protected. Thus in bacteriophage, unlike the cases of bacteria and spores, it is important to retain in engineered outer surface protein-Trp cage binding domain fusion proteins those residues of the parental outer surface protein that interact with other proteins in the virion. For M13 gVIII, we retain the entire mature protein, while for M13 gIII, it might suffice to retain the last 100 residues (or even fewer). Such a truncated gIII protein would be expressed in parallel with the complete gIII protein, as gIII protein is required for phage infectivity.

An especially useful system is the phage display system produced by Dyax Corporation, Cambridge, Mass. and New England Biolabs, Beverly, Mass.

Filamentous Phage

Compared to other bacteriophage, filamentous phage in general are attractive and M13 in particular is especially attractive because: (1) the 3D structure of the virion is known; (2) the processing of the coat protein is well understood; (3) the genome is expandable; (4) the genome is small; (5) the sequence of the genome is known; (6) the virion is physically resistant to shear, heat, cold, urea, guanidinium Cl, low pH, and high salt; (7) the phage is a sequencing vector so that sequencing is especially easy; (8) antibiotic-resistance genes have been cloned into the genome with predictable results; (9) it is easily cultured and stored, with no unusual or expensive media requirements for the infected cells; (10) it has a high burst size, each infected cell yielding 100 to 1000 M13 progeny after infection; and (11) it is easily harvested and concentrated. The filamentous phage include M13, fl, fd, Ifl, Ike, Xf, Pf1, and Pf3.

The entire life cycle of the filamentous phage M13, a common cloning and sequencing vector, is well understood. M13 and fl are so closely related that we consider the properties of each relevant to both; any differentiation is for historical accuracy. The genetic structure (the complete sequence, the identity and function of the ten genes, and the order of transcription and location of the promoters) of M13 is well known as is the physical structure of the virion. Because the genome is small (6423 bp), cassette mutagenesis is practical on RF M13, as is single-stranded oligonucleotide directed mutagenesis. M13 is a plasmid and transformation system in itself, and an ideal sequencing vector. M13 can be grown on Rec.— strains of *E. coli*. The M13 genome is expandable and M13 does not lyse cells. Because the M13 genome is extruded through the membrane and coated by a large number of identical protein molecules, it can be used as a cloning vector.

Thus we can insert extra genes into M13 and they will be carried along in a stable manner.

The major coat protein is encoded by gene VIII. The 50 amino acid mature gene VIII coat protein is synthesized as a 73 amino acid precoat. The first 23 amino acids constitute a typical signal-sequence which causes the nascent polypeptide to be inserted into the inner cell membrane. Whether the precoat inserts into the membrane by itself or through the action of host secretion components, such as SecA and SecY, remains controversial, but has no effect on the operation of the present invention.

An *E. coli* signal peptidase recognizes amino acids 18, 21, and 23, and, to a lesser extent, residue 22, and cuts between residues 23 and 24 of the precoat. After removal of the signal sequence, the amino terminus of the mature coat is located on the periplasmic side of the inner membrane; the carboxy terminus is on the cytoplasmic side. About 3000 copies of the mature 50 amino acid coat protein associate side-by-side in the inner membrane.

The sequence of gene VIII is known, and the amino acid sequence can be encoded on a synthetic gene, using lacUV5 promoter and used in conjunction with the LacI$^q$ repressor. The lacUV5 promoter is induced by IPTG. Mature gene VIII protein makes up the sheath around the circular ssDNA. The 3D structure of fl virion is known at medium resolution; the amino terminus of gene VIII protein is on surface of the virion. The 2D structure of M13 coat protein is implicit in the 3D structure. Mature M13 gene VIII protein has only one domain. When the microbe is M13 the gene III and the gene VIII proteins are highly preferred as outer surface protein. The proteins from genes VI, VII, and IX may also be used.

Thus, to produce novel Trp cage binding domains of the present invention we can construct a tripartite gene comprising: (1) DNA encoding a signal sequence directing secretion of parts (2) and (3) through the inner membrane; (2) DNA encoding the mutated forms of a Trp cage binding domain sequence, and (3) DNA encoding the mature M13 gVIII protein. This gene causes a Trp cage binding domain polypeptide to appear in active form on the surface of M13 phage.

The gene III protein is a preferred outer surface protein because it is present in many copies and because its location and orientation in the virion are known. Preferably, the Trp cage binding domain is attached to the amino terminus of the mature M13 coat protein.

Similar constructions could be made with other filamentous phage. Pf3 is a well-known filamentous phage that infects *Pseudomonas aerugenosa* cells that harbor an IncP-1 plasmid. The entire genome has been sequenced and the genetic signals involved in replication and assembly are known. The major coat protein of Pf3 is unusual in having no signal peptide to direct its secretion. Thus, to cause a Trp cage binding domain to appear on the surface of Pf3, we construct a tripartite gene comprising: (I) a signal sequence known to cause secretion in *P. aerugenosa* (preferably known to cause secretion of binding domain) fused in-frame to; (2) a gene fragment encoding the Trp cage binding domain sequence, fused in-frame to; and (3) DNA encoding the mature Pf3 coat protein.

Optionally, DNA encoding a flexible linker of one to 10 amino acids is introduced between the binding domain gene fragment and the PO coat-protein gene. Optionally, DNA encoding the recognition site for a specific protease, such as tissue plasminogen activator or blood clotting Factor Xa, is introduced between the binding domain gene fragment and the PO coat-protein gene. Amino acids that form the recognition site for a specific protease may also serve the function of a flexible linker. This tripartite gene is introduced into Pf3 so that it does not interfere with expression of any Pf3 genes. To reduce the possibility of genetic recombination, part (3) is designed to have numerous silent mutations relative to the wild-type gene. Once the signal sequence is cleaved off, the binding domain is in the periplasm and the mature coat protein acts as an anchor and phage-assembly signal. It matters not that this fusion protein comes to rest in the lipid bilayer by a route different from the route followed by the wild-type coat protein.

The amino-acid sequence of M13 pre-coat, is:

```
                                              (SEQ ID NO: 5)
      MKKSLVLKASVAVATLVPMLSFAAEGDDPAKAAFNSLQASATEYI
GYAWAMVVVIVGATIGIKLFKKFTSKAS
```

The best site for inserting a novel protein domain into M13 CP is after A23 because SP-1 cleaves the precoat protein after A23. Trp cage binding domain polypeptides appear connected to mature M13 CP at its amino terminus. Because the amino terminus of mature M13 CP is located on the outer surface of the virion, the introduced domain will be displayed on the outside of the virion.

Another vehicle for displaying the binding domain is by expressing it as a domain of a chimeric gene containing part or all of gene III. This gene encodes one of the minor coat proteins of M13. Genes VI, VII, and IX also encode minor coat proteins. Each of these minor proteins is present in about 5 copies per virion and is related to morphogenesis or infection. In contrast, the major coat protein is present in more than 2500 copies per virion. The gene VI, VII, and IX proteins are present at the ends of the virion; these three proteins are not post-translationally processed.

The single-stranded circular phage DNA associates with about five copies of the gene III protein and is then extruded through the patch of membrane-associated coat protein in such a way that the DNA is encased in a helical sheath of protein. The DNA does not base pair (that would impose severe restrictions on the virus genome); rather the bases intercalate with each other independent of sequence.

The T7 Bacterophage Display System

An alternative method for the production and display of Trp cage ligands is the use of a phage display system based upon the bacteriophage T7. T7 is a double-stranded DNA phage the assembly of which occurs inside *E. coli* cells and mature phage are released by cell lysis. Unlike the filamentous systems described above, the Trp cage ligands displayed on the surface of T7 do not need to be capable of secretion through the cell membrane, which is a necessary step in filamentous display. An example of such a system is the T7Select® phage display system produced by Novagen®, San Diego, Calif.

Bacterial Cells as Recombinant Microbes

One may choose any well-characterized bacterial strain which (1) may be grown in culture, (2) may be engineered to display Trp cage binding domains on its surface, and (3) is compatible with affinity selection. Among bacterial cells, the preferred genetic packages are *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli*. The potential binding mini-protein may be expressed as an insert in a chimeric bacterial outer surface protein (outer surface protein). All bacteria exhibit proteins on their outer surfaces.

In *E. coli*, LamB is a preferred outer surface protein. As discussed below, there are a number of very good alternatives in *E. coli* and there are very good alternatives in other bacterial species. There are also methods for determining the topology of outer surface proteins so that it is possible to systematically determine where to insert a binding domain into an outer surface protein gene to obtain display of a binding domain on the surface of any bacterial species.

In view of the extensive knowledge of *E. coli*, a strain of *E. coli*, defective in recombination, is the strongest candidate.

While most bacterial proteins remain in the cytoplasm, others are transported to the periplasmic space (which lies between the plasma membrane and the cell wall of gram-negative bacteria), or are conveyed and anchored to the outer surface of the cell. Still others are exported (secreted) into the medium surrounding the cell. Those characteristics of a protein that are recognized by a cell and that cause it to be transported out of the cytoplasm and displayed on the cell surface will be termed "outer-surface transport signals."

Gram-negative bacteria have outer-membrane, that form a subset of outer surface proteins. Many outer-membrane proteins span the membrane one or more times. The signals that cause outer-membrane proteins to localize in the outer membrane are encoded in the amino acid sequence of the mature protein. Outer membrane proteins of bacteria are initially expressed in a precursor form including a so-called signal peptide. The precursor protein is transported to the inner membrane, and the signal peptide moiety is extruded into the periplasmic space. There, it is cleaved off by a "signal peptidase," and the remaining "mature" protein can now enter the periplasm. Once there, other cellular mechanisms recognize structures in the mature protein which indicate that its proper place is on the outer membrane, and transport it to that location.

It is well known that the DNA coding for the leader or signal peptide from one protein may be attached to the DNA sequence coding for another protein, protein X, to form a chimeric gene whose expression causes protein X to appear free in the periplasm. That is, the leader causes the chimeric protein to be secreted through the lipid bilayer; once in the periplasm, it is cleaved off by the signal peptidase SP-1.

The use of export-permissive bacterial strains increases the probability that a signal-sequence-fusion will direct the desired protein to the cell surface. Outer surface protein-binding domain fusion proteins need not fill a structural role in the outer membranes of Gram-negative bacteria because parts of the outer membranes are not highly ordered. For large outer surface proteins there is likely to be one or more sites at which outer surface protein can be truncated and fused to binding domain such that cells expressing the fusion will display binding domains on the cell surface. Fusions of fragments of omp genes with fragments of an x gene have led to X appearing on the outer membrane. When such fusions have been made, we can design an outer surface protein-Trp cage binding domain gene by substituting binding domain for x in the DNA sequence. Otherwise, a successful outer-membrane proteins-binding domain fusion is preferably sought by fusing fragments of the best outer-membrane protein to a Trp cage binding domain, expressing the fused gene, and testing the resultant microbes for display-of-Trp cage binding domain phenotype. We use the available data about the outer-membrane proteins to pick the point or points of fusion between omp and binding domain to maximize the likelihood that binding domain will be displayed (spacer DNA encoding flexible linkers, made, e.g., of GLY, SER, ALA and ASN, may be placed between the outer surface protein- and binding domain-derived fragments to facilitate display).

Alternatively, we truncate outer surface protein at several sites or in a manner that produces outer surface protein fragments of variable length and fuse the outer surface protein fragments to a Trp cage binding domain; cells expressing the fusion are screened or selected which display binding domains on the cell surface. Fragments of outer surface proteins (such as OmpA) above a certain size are incorporated into the outer membrane. An additional alternative is to include short segments of random DNA in the fusion of omp fragments to binding domain and then screen or select the resulting variegated population for members exhibiting the display-of-Trp cage binding domain phenotype.

In *E. coli*, the LamB protein is a well understood outer surface protein and can be used. The *E. coli* LamB has been expressed in functional form in *S. typhimurium* cholerae, and *K. pneumonia*, so that one could display a population of Trp cage binding domains in any of these species as a fusion to *E. coli* LamB. *K. pneumonia* expresses a maltoporin similar to LamB, which could also be used. In *P. aeruginosa*, the D1 protein (a homologue of LamB) can be used.

LamB of *E. coli* is a porin for maltose and maltodextrin transport, and serves as the receptor for adsorption of bacteriophages lambda and K10. LamB is transported to the outer membrane if a functional N-terminal sequence is present; further, the first 49 amino acids of the mature sequence are required for successful transport. As with other outer surface proteins, LamB of *E. coli* is synthesized with a typical signal-sequence which is subsequently removed. Homology between parts of LamB protein and other outer membrane proteins OmpC, OmpF, and PhoE has been detected, including homology between LamB amino acids 39-49 and sequences of the other proteins. These subsequences may label the proteins for transport to the outer membrane.

The amino acid sequence of LamB is known, and a model has been developed of how it anchors itself to the outer membrane. The location of its maltose and phage binding domains are also known. Using this information, one may identify several strategies by which a Trp cage binding domain insert may be incorporated into LamB to provide a chimeric outer surface protein, which displays the Trp cage binding domain on the bacterial outer membrane.

When the Trp cage binding domain polypeptides are to be displayed by a chimeric transmembrane protein like LamB, the Trp cage binding domain could be inserted into a loop normally found on the surface of the cell. Alternatively, we may fuse a 5' segment of the outer surface protein gene to the Trp cage binding domain gene fragment; the point of fusion is picked to correspond to a surface-exposed loop of the outer surface protein and the carboxy terminal portions of the outer surface protein are omitted. In LamB, it has been found that up to 60 amino acids may be inserted with display of the foreign epitope resulting. The structural features of OmpC, OmpA, OmpF, and PhoE are so similar that one expects similar behavior from these proteins.

Other bacterial outer surface proteins, such as OmpA, OmpC, OmpF, PhoE, and pilin, may be used in place of LamB and its homologues. OmpA is of particular interest because it is very abundant and because homologues are known in a wide variety of gram-negative bacterial species. Insertion of a Trp cage binding domain encoding fragment at about codon 111 or at about codon 152 is likely to cause the binding domain to be displayed on the cell surface.

Porin Protein F of *Pseudomonas aeruginosa* has been cloned and has sequence homology to OmpA of *E. coli*. The insertion of a Trp cage binding domain gene fragment at about codon 164 or at about codon 250 of the *E. coli* ompC gene or at corresponding codons of the *S. typhimurium* ompC gene is likely to cause the Trp cage binding domain to appear on the cell surface. The ompC genes of other bacterial species may be used.

OmpF of *E. coli* is a very abundant outer surface protein, .gtoreq.104 copies/cell. Fusion of a Trp cage binding domain gene fragment, either as an insert or to replace the 3' part of ompF, in one of the indicated regions is likely to produce a functional ompF::Trp cage binding domain gene the expression of which leads to display of the Trp cage binding domain on the cell surface. In particular, fusion at about codon 111, 177, 217, or 245 should lead to a functional ompF::Trp cage binding domain gene.

Pilus proteins are of particular interest because piliated cells express many copies of these proteins and because several species (*N. gonorrhoeae, P. aeruginosa, Moraxella bovis, Bacteroides nodosus*, and *E. coli*) express related pilins. A GLY-GLY linker between the last pilin residue and the first residue of the foreign epitope to provide a "flexible linker" is very useful. Thus a preferred place to attach a Trp cage binding domain is the carboxy terminus. The exposed loops of the bundle could also be used.

The protein 1A of *N. gonorrhoeae* can also be used; the amino terminus is exposed; thus, one could attach a Trp cage binding domain at or near the amino terminus of the mature P.IA as a means to display the binding domain on the *N. gonorrhoeae* surface.

The PhoE of *E. coli* has also been used. This model predicts eight loops that are exposed; insertion of a Trp cage binding domain into one of these loops is likely to lead to display of the binding domain on the surface of the cell. Residues 158, 201, 238, and 275 are preferred locations for insertion of and binding domain.

Other outer surface proteins that could be used include *E. coli* BtuB, FepA, FhuA, IutA, FecA, and FhuE, which are receptors for nutrients usually found in low abundance.

Bacterial Spores as Recombinant Microbes:

Bacterial spores have desirable properties as recombinant microbe candidates. Spores are much more resistant than vegetative bacterial cells or phage to chemical and physical agents, and hence permit the use of a great variety of affinity selection conditions. Also, *Bacillus* spores neither actively metabolize nor alter the proteins on their surface. Spores have the disadvantage that the molecular mechanisms that trigger sporulation are less well worked out than is the formation of M13 or the export of protein to the outer membrane of *E. coli*.

Bacteria of the genus *Bacillus* form end outer surface protein spores that are extremely resistant to damage by heat, radiation, desiccation, and toxic chemicals. This phenomenon is attributed to extensive intermolecular cross linking of the coat proteins. End outer surface protein spores from the genus *Bacillus* are more stable than are outer surface protein spores from *Streptomyces. Bacillus subtilis* forms spores in 4 to 6 hours, but *Streptomyces* species may require days or weeks to sporulate. In addition, genetic knowledge and manipulation is much more developed for *B. subtilis* than for other spore-forming bacteria. Thus *Bacillus* spores are preferred over *Streptomyces* spores. Bacteria of the genus *Clostridium* also form very durable endospores, but clostridia, being strict anaerobes, are not convenient to culture.

Viable spores that differ only slightly from wild-type are produced in *B. subtilis* even if any one of four coat proteins is missing. Moreover, plasmid DNA is commonly included in spores, and plasmid encoded proteins have been observed on the surface of *Bacillus* spores. For these reasons, we expect that it will be possible to express during sporulation a gene encoding a chimeric coat protein, without interfering materially with spore formation.

Fusions of binding domain fragments to cotC or cotD fragments are likely to cause binding domain to appear on the spore surface. The genes cotC and cotD are preferred outer surface protein genes because CotC and CotD are not post-translationally cleaved. Subsequences from cotA or cotB could also be used to cause a binding domain to appear on the surface of *B. subtilis* spores, but we must take the post-translational cleavage of these proteins into account. DNA encoding Trp cage binding domain could be fused to a fragment of cotA or cotB at either end of the coding region or at sites interior to the coding region. Spores could then be screened or selected for the display-of-binding domain phenotype.

As stated above, in the preferred embodiment of the present invention the microbe for producing the Trp cage library is a bacteriophage. The present invention is also directed towards a method for producing novel Trp cage peptide ligands comprised producing a random set of nucleic acids that encode Trp cage peptide into a phage-display viral vector, growing the resultant virus into bacteria to produce new viruses, analyzing the resultant Trp-cage peptides expressed on the surface of the bacterially-produced viruses to find one that binds to a predetermined receptor or enzyme. The present invention also provides for substrate peptides that complex with enzymes so as to antagonize the interaction of the enzyme with its substrate.

According to the present invention, novel Trp cage polypeptides are produced by first synthesizing the above-described polynucleotide of SEQ ID NO: 2 preferably using a DNA synthesizer such as the Expedite 8900®, PerSeptive Biosystems. At the steps where a nucleotide 'M' is designated, both 'A' and 'C' nucleotides are added preferably in equimolar amounts and 'K' is designated, both 'T' and 'G' nucleotide are added preferably in equimolar amounts. At the steps where a nucleotide 'N' is designated, 'A', 'C', 'T' and 'G' nucleotides are added preferably in equimolar amounts. Thus results in are large number of nucleotide sequences being produced, which are capable of encoding upwards to $10^9$ 23 residue Trp-cage peptide sequences.

The nucleotide sequence, encoding the novel Trp cage peptides is spliced into the phages existing gene 3 sequence, and expressed on one end of the outer protein coat of the phage. Each phage only receives one DNA, so each expresses a single Trp cage peptide. Collectively, the population of phage can display a billion or more Trp cage peptides. This produces a Trp cage peptide library, which is a collection of phage displaying a population of related but diverse Trp cage peptides. Next this library of Trp cage peptides is exposed to receptor or enzymatic targets, which are preferably immobilized. After the phage expressing the Trp cage peptides are given a sufficient time to bind to the potential targets, the immobilized target is washed to remove phage that did not bind to the target. One only need capture one phage that binds to the target by means of an expressed Trp cage peptide. Several million of the positive phage can then be produced overnight providing for enough sequence for nucleotide sequence determination, thus identifying the amino sequence of the Trp cage peptide and the DNA that encodes it. The Trp cage peptides that are created and isolated using the phage display method have a specific interaction with a known disease target, making this a rapid, effective and focused drug discovery method.

Display Strategy: Displaying Trp Cage Ligands on Bacteriophage T7

An alternative method for the production and display of Trp cage ligands is the use of a phage display system based upon the bacteriophage T7. T7 is a double-stranded DNA phage the assembly of which occurs inside *E. coli* cells and mature phage are released by cell lysis. Unlike the filamentous systems described above, the Trp cage ligands displayed on the surface of T7 do not need to be capable of secretion through the cell membrane, which is a necessary step in filamentous display.

All publications, references, patents, patent publications and patent applications cited herein are each hereby specifically incorporated by reference in their entirety.

While this invention has been described in relation to certain embodiments, and many details have been set forth for purposes of illustration, it will be apparent to those skilled in the art that this invention includes additional embodiments, and that some of the details described herein may be varied considerably without departing from this invention. This invention includes such additional embodiments, modifications and equivalents. In particular, this invention includes any combination of the features, terms, or elements of the various illustrative components and examples.

The use herein of the terms "a," "an," "the," and similar terms in describing the invention, and in the claims, are to be construed to include both the singular and the plural. The terms "comprising," "having," "including," and "containing" are to be construed as open-ended terms which mean, for example, "including, but not limited to." Recitation of a range of values herein refers individually to each separate value falling within the range as if it were individually recited herein, whether or not some of the values within the range are expressly recited. Specific values employed herein will be understood as exemplary and not to limit the scope of the invention.

Definitions of technical terms provided herein should be construed to include without recitation those meanings associated with these terms known to those skilled in the art, and are not intended to limit the scope of the invention.

The examples given herein, and the exemplary language used herein are solely for the purpose of illustration, and are not intended to limit the scope of the invention.

When a list of examples is given, such as a list of compounds or molecules suitable for this invention, it will be apparent to those skilled in the art that mixtures of the listed compounds or molecules are also suitable.

EXAMPLES

Example 1

Materials and Methods

The present example illustrates the materials and methods used within the instant application.

Chemicals, Media and Reagents

General chemicals were purchased from Sigma® (St. Louis, Mo.). Components for bacterial growth media were purchased from Fisher® (Fair Lawn, N.J.). T7Select® Cloning kits, vector arms, packaging extracts, S•Tag® antibody, and T7 Tail Fiber Monoclonal Antibody were purchased from Novagen® (EMD Biosciences, San Diego, Calif.). Restriction enzymes EcoRI and HindIII, and Streptavidin were purchased from New England Biolabs® (Beverly, Mass.). EcoRI and HindIII were used according to the manufacturer's instructions. Mammalian cell media, Klenow Fragment of DNA polymerase 1, MagicMark® XP Western Protein Standards and reagents for SDS-PAGE electrophoresis were purchased from Invitrogen® (Carlsbad, Calif.). Goat anti-rabbit IgG HRP and goat anti-mouse IgG HRP antibodies were purchased from Santa Cruz Biotech® (Santa Cruz, Calif.). SuperSignal West Femto Maximum Sensitivity Substrate® was purchased from Pierce® (Rockford, Ill.).

Growth of Bacteria and Bacteriophage:

The hosts for bacteriophage T7Select® phage obtained from Novagen® (EMD Biosciences, San Diego, Calif.) were either *Escherichia coli* (*E. coli*) strain BL21 ((F$^-$, ompT, hsdS$_B$ (r$_B^-$m$_B^-$), gal, dcm); for T7Select® 415-b) or BLT5403 ((F$^-$, ompT, hsdS$_B$ (r$_B^-$m$_B^-$), gal, dcm pAR5403 (Amp$^R$)); for T7Select® 10-3b and 1-1b). BL21 was grown in M9LB liquid media and BLT5403 was grown in M9LB supplemented with carbenicillin (50 µg/ml) at 37° C. *E. coli* strain ER2738 was used as the host for all the M13 libraries. *E. coli* C600 ATCC 23724 (F$^-$, supE44, lacY1, thr-1, leuB6, mcrA, thi-1, fhuA21, lambda$^-$) was obtained from American Type Culture Collection (Manassas, Va.) and V517 was obtained from Larry L. McKay, University of Minnesota. Human bronchial epithelial cell line 16HBE14o— was obtained from D. C. Gruenert, University of California, San Francisco, Calif.

Bacteriophage T7 was titered using the plaque assay method by combining 0.1 ml volumes of serially diluted bacteriophage and the appropriate bacterial host grown to OD$_{600}$=1.0, adding 3.0 ml of molten top agar (0.75% agar in LB), spreading the mixture onto LB solid media (supplemented with carbenicillin as above for BLT5403) and incubation overnight at room temperature or four hours at 37° C.

Bacteriophage were prepared following the instructions in the T7Select® System Manual (Novagen). Briefly, host cells grown to a density of 2×10$^8$ cells/ml were infected with phage at a low multiplicity of infection (MOI=0.001-0.01) and incubated for one to three hours while shaking at 37° C. until cell lysis was observed. Phage lystates typically resulted in titers of 1×10$^{10}$ to 10$^{11}$ pfu/ml.

Phage were purified and concentrated from bacterial lysates that were centrifuged (12,000 g Sorvall SS-34, for 15 minutes at 4° C.) to remove unlysed cells and cell debris by adding ⅙ volume of 20% polyethylene glycol 8000, 2.5 M NaCl (PEG/NaCl) and incubating on ice for at least 60 minutes or overnight at 4° C. Precipitated phage were pelleted by centrifugation at 10,000 g (Sorvall SS-34) for 15 minutes at 4° C. The phage pellet was resuspended in TBS (50 mM Tris, pH 7.5, 150 mM NaCl) and reprecipitated with ⅙ volume of PEG/NaCl on ice for 15 to 60 minutes and centrifuged to form a phage pellet which was resuspended in TBS and stored at 4° C.

Preparation of Phage DNA for Sequencing:

Phage plaques were punched out of solid media and resuspended in 100 µl TE (10 mM Tris pH 8.0, 1 mM EDTA). Host bacteria were grown to a density of 2×10$^8$ cfu/ml and 2.5 µl of the phage suspension was added to 1 ml of the bacteria culture in a 17×100 mm tube followed by incubation for three hours with shaking at 37° C. Then 1 µl of Nuclease mix containing RNase A and DNase I (Promega® Madison, Wis.) was added and incubation was continued for 15 minutes without shaking at 37° C. Cell debris was removed by centrifugation in a microfuge (Eppendorf® 5415C) at 16,000 g for 10 minutes. A 900 µl volume of the supernatant was recovered and transferred to a new 1.5 ml tube containing 200 µl of 20% PEG-8000, 2.5M NaCl and incubated overnight at 4° C. Precipitated phage were collected by centrifugation for ten minutes at 16,000 g. Phage were resuspended in 100 µl TE and disrupted by extraction with an equal volume of phenol:chloroform (1:1), then centrifuged for 1 minute in a microfuge at 16,000 g. The aqueous phase was recovered, extracted with an equal volume of chloroform, then centrifuged for four minutes. The aqueous phase was recovered again and 1/10th volume of 3 M sodium acetate was added. Alternatively, the phage were disrupted by resuspension in 100 μl Iodide Buffer (10 mM Tris pH 8, 1 mM EDTA, 4M NaI). Phage DNA was precipitated by the addition of 250 μl ethanol and incubation for 10 minutes at room temperature. Precipitated DNA was pelleted by centrifugation at 16,000 g for 10 minutes, washed with 70% ethanol and dried briefly under vacuum. The DNA pellet was resuspended in 20 to 30 μl of TE.

DNA Sequencing:

T7 DNA was submitted to Retrogen® (San Diego, Calif.) for automated DNA sequencing by an ABI 3730 DNA Analyzer using the primer T7-125 (TGCGTGACTTGGCTCTG-GAG; SEQ ID NO: 6). A protocol model was constructed for sequence analysis using Teranode software which also served as a sequence database.

Oligonucleotide Synthesis:

The following oligonucleotides were synthesized by Retrogen® (San Diego, Calif.): TC3b (+) Synthesized at 0.2 μM scale and PAGE purified (SEQ ID NO: 7)
5'-AAT TTA TTT ATC GAA TGG CTC AAA AAT GGT GGT CCT

TCC AGT GGT GCT CCT CCC CCT TCC TAA-3'

TC3b (−) Synthesized at 0.2 μM scale and PAGE purified (SEQ ID NO: 8)
5'-AGCT TTA GGA AGG GGG AGG AGC ACC ACT GGA AGG

ACC ACC ATT TTT GAG CCA TTC GAT AAA TA-3'

TC5b (+) Synthesized at 0.05 μM scale and desalted (SEQ ID NO: 9)
5'-AAT TCG GCA GCT GCG AAT TTG TAT ATT CAG TGG CTT

AAG GAT GGT GGT CCT TCG TCG GGG CGG CCT CCG CCA

AGT TAA A-3'

TC5b (−) Synthesized at 0.05 μM scale and desalted (SEQ ID NO: 10)
5'-AG CTT TTA ACT TGG CGG AGG CCG CCC CGA CGA AGG

ACC ACC ATC CTT AAG CCA CTG AAT ATA CAA ATT CGC

AGC TGC CG -3'

T-3 (+) Synthesized at 0.05 μM scale and PAGE purified

5'- CACATGCCCCGAATTCGGCA-3'  (SEQ ID NO: 11)

T-3 (−) Synthesized at 0.2 uM scale and PAGE purified (SEQ ID NO: 12)
5'-CATGT TCA AGC TTG TTA MNN GGG GGG AGG ACG ACC

AGA MNN AGG ACC MNN MNN MNN TAA CCA CTG MNN GTA

MNN ATC TGC TGC TGC CGA ATT CGG GGC ATG TG-3'

Where M represents equal molar amounts of the nucleotides adenine (A) or cytosine (C) and where N represents equal molar amounts of adenine (A), cytosine (C), thymine (T) or guanine (G).

Insertion of Nucleotide Sequences Encoding TC3b or TC5b into T7Select Vectors:

Oligonucleotide pairs were designed to encode the Trp cage TC3b and TC5b proteins based on codons commonly utilized by *E. coli* and T7. Each oligonucleotide was resuspended in TE to 200 pmoles/μl before annealing. Oligonucleotide TC3b (+) was annealed with TC3b (−), and TC5b (+) was annealed with TC5b (−) by combining 25 μl of each of the appropriate oligonucleotides in annealing buffer (10 mM Tris pH7.5, 100 mM NaCl, 1 mM EDTA), the mixture was heated for 5 minutes to 95° C. in a heat block and the block with samples was allowed to cool for two hours at room temperature. The annealed oligos were ligated to the arms of T7Select® 415-1b, 10-3b or 1-1b and packaged in vitro using the T7 Select® Cloning kit (Novagen®) according to the manufacturer's directions. Packaged phage were amplified by growth in liquid media with the appropriate host. After amplification, phage titer was determined and individual well-isolated plaques were selected for nucleotide sequencing to confirm the presence of the correct insert.

Peptide Synthesis:

Peptides were synthesized by solid-phase Fmoc chemistry on TGR-amide resin using a Rainin Symphony synthesizer. Coupling steps were performed for 40 minutes using five equivalents of HCTU and Fmoc amino acid with an excess of N-methylmorpholine for 40 minutes. Fmoc removal was accomplished by treating the peptide resin for two 10 minute cycles with 20% piperidine (Aldrich®, Milwaukee, Wis.) in DMF (Burdick and Jackson, Morristown, N.J.) for two 10-minute cycles. Upon completion of the peptide, the Fmoc group was removed with piperidine and washed extensively with DMF. The peptides were cleaved from the resin by the addition of 10 mL of TFA (Aldrich®, Milwaukee, Wis.) containing 2.5% water and 2.5% triisopropylsilane (Aldrich®, Milwaukee, Wis.) followed by a two hours gentle agitation at room temperature. The resulting crude peptide was collected by trituration with ether followed by filtration. The crude product was dissolved in Millipore water and lyophilized to dryness. The crude peptide was taken up in 15 ml of water containing 0.05% TFA and three ml acetic acid and loaded onto a Zorbax RX-C8 reversed-phase (22 mm ID×250 mm, 5 μm particle size) through a 5 ml injection loop at a flow rate of 5 ml/min. The purification was accomplished by running a linear AB gradient of 0.1% B/min for 180 minutes, where solvent A is 0.05% TFA in water and solvent B is 0.05% TFA in acetonitrile. The purified peptides were analyzed by reverse phase (RP)-HPLC and electrospray mass spectrometry. Peptides were purified to greater than 95% purity as determined by (RP)-HPLC.

Production of Antibody AB167:

The TC5b peptide was synthesized with the addition of a cysteine residue at the N-terminus to allow conjugation of keyhole limpet hemaocyanin (KLH) and designated PN0522 (NH2-CNLYIQWLKDGGPSSGRPPPS-amide: SEQ ID NO: 13). The KLH conjugated protein was used to generate antibodies in New Zealand white rabbits by Orbigen (San Diego, Calif.). For the first immunization each rabbit was injected with 200 μg of antigen in Freud's Complete Adjuvant. There were four boost injections at three week intervals using 100 μg of antigen in Freud's Incomplete Adjuvant. Two weeks after the last boost the final bleed was performed and IgG was purified from scrum by protein G affinity chromatography.

ELISA (Detection of Trp Cage TC5b):

Phage purified by double precipitation with PEG was diluted in Dulbecco's PBS (DPBS) and applied to wells of a 96-well Maxisorp® plate (Nalge Nunc International®, Rochester, N.Y.) and allowed to bind for one hour followed by three washes with 400 μl of OptEIA wash buffer (BD Biosciences) and blocking with 1% BSA in TBS-Tween (0.1%). All washes were done at room temperature with slow orbital shaking. Antibody AB167 diluted 1:500 was applied in PBS-T containing 1% BSA and allowed to bind for one hour at room temperature then washed five times with 400 μl of wash buffer. Bound antibody was detected with the secondary antibody goat anti-rabbit HRP diluted 1:1000 in PBS-T with 1% BSA applied for one hour and washed five times with 400 μl of wash buffer followed by development with OptEIA reagents according to the manufacturer's directions. Means were compared using Student's t-test.

For screening cell-specific binding phage display peptides, confluent HepG2 or HUVEC cells grown in DMEM-F12-complete in a 96-well plate fixed with methanol, stored at 4° C. Applied 250 μl/well of diluted phage and incubated in wells for 1 hour while shaking. Stopped reactions with 75 ul of 1M HCl after ~5-7 min, read at 450 nm.

Phage binding to 16HBE140-cells was analyzed using confluent cells grown with DMEM-F12 complete medium in 96-well collagen coated plates (BD Biosciences, San Diego, Calif.) at 37° C. in 5% $CO_2$. The cells were washed with DPBS and phage diluted in DPBS containing 1% BSA (DPBS-BSA) were applied in 100 μl. Bound phage were detected using primary antibody (mouse IgG T7 tail fiber monoclonal antibody diluted 1:2000 in DPBS-BSA) and secondary antibody (goat anti-mouse IgG HRP diluted 1:5000 in DPBS-BSA) followed by detection with OptEIA reagents as above.

Detection of FITC-Labeled Phage in HepG2 Cells:

The phage microscopy protocol is as follows:

1. Grow HepG2 cells on collagen 1 coated glass chamber slides to 100% confluence.
2. On the day of the experiment, wash cells 3 to 5 times ~300 μl/well of PBS.
3. Fix with 100 μl/well of methanol (chilled at −20 C) for 7 min at room temperature.
4. Wash 3-5 times with ~300 μl/well of PBS.
5. Apply 10 μl/well (~c9 pfu) of FITC-labeled M13 phage.
6. Incubate on a rotating platform at room temperature for 1 hr in the dark.
7. Wash 5 times with ~300 μl/well of PBS.
8. Remove chambers, dry, mount, and visualize at 200×.

Western Analysis of Phage Displaying TC5b:

For Western analysis, phage were purified by double precipitation with PEG and denatured by boiling in Tris-Glycine SDS sample buffer (2×) with 1% beta-mercaptoethanol (BME). A 10 μl sample containing $1 \times 10^{11}$ pfu/ml was loaded into a well of a 1 mm 4% to 20% Tris-Glycine gel (Invitrogen®) and electrophoresed for 1.5 hours at 150 volts (constant voltage) in Tris-Glycine SDS running buffer. The separated proteins were transferred to a PVDF membrane (1.5 hours at room temperature) and blocked with 3% non-fat dry milk in TBS-T (0.05%) for one hour at room temperature. The membrane was probed for two hours with antibody AB167 diluted 1:2500 at room temperature followed by three five minute washes with TBS-T. Goat anti-rabbit HRP diluted 1:5000 was used to detect the bound ABI 67 antibody. It was incubated with the membrane for one hour at room temperature followed by four 10 minute washes and the membrane was developed with SuperSignal West Femto Maximum Sensitivity Substrate® (Pierce®) according to the manufacturer's instructions. MagicMark® XP Western Protein Standards were used for size reference standards.

Construction of the Trp Cage Library:

The Trp cage library was constructed in the T7Select® 10-3b vector using oligo T-3 (−) as a template and T-3 (+) as a primer. The oligo and primer were annealed by combining 310 pmole of the T-3 oligo and 820 pmole of the primer in annealing buffer (10 mM Tris pH 7.5, 100 mM NaCl, 1 mM EDTA) for a final volume of 50 μl, the mixture was heated to 95° C. in a heat block for five minutes and the block was allowed to cool for two hours at room temperature.

The primer was extended with the Klenow fragment of DNA polymerase I by combining 310 pmole of annealed oligo/primer, dNTP mixture (New England Biolabs®), REact 2 buffer (Invitrogen®) and Klenow (10 units) in a total volume of 250 μl for 10 minutes at 37° C. The reaction was stopped by incubation at 65° C. for 15 minutes followed by phenol/chloroform extraction and ethanol precipitation.

The extended duplexes were double digested with EcoRI and HindIII and the cleavage products were subjected to electrophoresis in a 20% TBE gel. The desired band was excised from the gel and extracted by shaking overnight in 100 mM sodium acetate, pH 4.5, 1 mM EDTA, 0.1% SDS at room temperature. Gel fragments were removed by centrifugation and the DNA was purified from the supernatant by phenol/chloroform extraction and ethanol precipitation before being resuspended in TE.

The extracted inserts were ligated into arms of T7Select® 10-3b and packaged in vitro using the T7Select® Cloning kit (Novagen®) according to the manufacturer's directions. Primary clones were titered and amplified in E. coli strain BLT5403. Ligation and packaging was repeated until greater than $1 \times 10^9$ primary clones were generated and amplified.

The amplified clones were pooled, treated for 15 minutes with DNase at 37° C. and centrifuged (Sorvall SS34, 8000 rpm, 10 minutes) to remove cell debris. Phage were concentrated by adding solid PEG 8000 to 10% (w/v), allowing the precipitate to form overnight at 4° C. and collecting the precipitated phage by centrifugation (Fiberlite F14-6, 8000 rpm, 10 minutes, 4° C.). The phage pellet was resuspended in 1M NaCl, 10 mM Tris pH 8, 1 mM EDTA. For further purification, the concentrated phage were layered on top of a CsCl density block gradient consisting of 1.5 ml 62%, 3.0 ml 41%, 3.0 ml 31% and 3.0 ml 20% CsCl in TE and centrifuged for 98 minutes at 28,000 rpm in a Beckman SW28.1 rotor at 25° C. The phage band was recovered by side puncture and dialyzed against three changes of 20 mM Tris pH 8.0, 100 mM NaCl, 6 mM $MgSO_4$.

Construction of a Suppressor Host Strain for T7Select®:

Plasmid pAR5403 was isolated from BLT5403 using a QIAprep® Spin Miniprep Kit (Qiagen®, Valencia, Calif.) following the manufacturer's instructions. E. coli strain C600 ATCC 23724 was made competent for transformation by inoculating LB broth with a 1% innoculum of fresh overnight culture and incubating at 37° C. with shaking until the cell density reached $OD_{600}$=0.3, cells were pelleted by centrifugation (480 g, 10 min), resuspended in ice-cold 0.1 M $CaCl_2$, re-centrifuged and resuspended in $\frac{1}{50}^{th}$ volume of ice-cold 0.1 M $CaCl_2$. Transformation was accomplished by combining 200 ul of competent cells with 2 ul of pAR5403 (200 ng/μl), incubating on ice for 30 min, heat shocking at 42° C.

for 90 seconds, then placing on ice for two minutes. Transformants were selected by inoculating 100 ul of heat shocked cells into three milliliters of molten top agar which was then spread onto LB solid media containing 50 μg/ml carbenicillin and incubated at 37° C. overnight. Plasmid DNA was prepared from transformants by QIAprep® Spin Miniprep and examined after electrophoresis (65 volts for two hours) through a 10×15 cm 0.6% SeaKem® LE (Cambrex®, Rockland, Me.) agarose gel in TBE (89 mM Tris, 89 mM boric acid, 2 mM EDTA) running buffer followed by staining with ethidium bromide (0.5 μg/ml).

Mutant Growth Experiment:

A fresh overnight culture of BLT5403 was used to inoculate a 100 ml of M9TB/carb broth and incubated at 37° C. with shaking until $OD_{600}$=0.85 (~1×10$^8$ cfu/ml). The culture was divided into three 20 ml cultures and each culture was infected with a total of 4×10$^7$ pfu of either the mutant, non-mutant or mixed in a 1:1 ratio (MOI=0.02). The infected cultures were incubated with shaking at 37° C. for three hours or until lysis was complete and progeny were grown on LB (carb) using BLT5403 as described for phage titering. After overnight incubation at 37° C., 24 plaques resulting from the progeny of the mixed infection were punched out of the plate and 12 plaques resulting from the progeny of the single infections were punched out of the plates. Phage were eluted by suspending each plaque in 100 μl TE and, subsequently, 10 μl of each eluate was used to infect 1 ml cultures of mid-log BLT5403. These cultures were incubated for three hours at 37° C. and then centrifuged to remove cell debris in order to obtain a stock of each progeny clone. A 800 μl volume of each was stock was mixed with 140 ul 20% PEG-8000, 2.5M NaCl and incubated for one hour on ice. Precipitated phage were collected by centrifugation for 10 minutes at 14,000 rpm. Phage were disrupted by resuspension in 100 μl Iodide Buffer. Phage DNA was precipitated by the addition of 250 μl ethanol and incubated for 10 minutes. Precipitated DNA was pelleted by centrifugation for 10 minutes at 14,000 rpm, washed with 70% ethanol and dried briefly under vacuum. The DNA pellet was resuspended in 30 μl of TE and submitted for nucleotide sequencing.

One-Step Growth Experiment:

BLT5403 was grown in LB broth at 37° C. to a density of 2×10$^8$ cfu/ml and centrifuged to sediment a cell pellet. The cell pellet was resuspended in one-half the original volume of LB broth and then titered to determine input cells. One-half milliliter of resuspended cells (approximately 4×10$^8$ cfu/ml) was placed in a 17×100 mm tube and incubated for five minutes at 30° C. before adding 0.5 ml of the appropriate phage stock adjusted to a titer of 4×10$^9$ pfu/ml to provide a multiplicity of infection (MOI) of 10. Incubation at 30° C. was continued (T=0 minutes). At T=5 minutes after phage infection, 2 μg of T7 antiserum (Novagen T7 Tail Fiber Monoclonal Antibody, Cat No. 71530-3) was added to neutralize phage that had not yet infected a cell. At T=10 minutes, the cell and phage mixture was diluted 10$^4$-fold in a Growth Flask with LB broth. Incubation continued with vigorous shaking. At T=15 minutes, one milliliter was removed from the growth flask and mixed with one milliliter of LB broth containing two to three drops of $CHCl_3$. This mixture was vortexed and titered to determine the number of unadsorbed phage. At T=20 minutes, one ml was removed from the Growth Flask and the number of infected cells were determined. At T=90 minutes, two to three drops of $CHCl_3$ was added to the Growth Flask and the number of progeny phage were titered.

Streptavidin Panning:

Wells of a 96-well plate were coated with 200 ng of streptavidin (2 ng/μl) for at least one hour and blocked with 1% BSA in DPBS with 0.1% Tween-20 (DPBS-T) for one hour, then rinsed three times with 200 μl of DPBS-BT. For panning, 1.2×10$^9$ pfu of the library was applied to the well and allowed to bind for one hour at room temperature followed by 6 washes with 200 μl of DPBS-T. Bound phage were eluted by incubating each well for 10 minutes with 1% SDS. Eluted phage was then amplified with BLT5403. The lysate was centrifuged and the supernatant was used for the next round of panning. After a total of 3 rounds of panning, eluted phage were grown on an agar plate with BLT5403. Well isolated plaques were selected for nucleotide sequencing.

Panning Against Human Bronchial Epithelial Cells:

Human bronchial epithelial cells (16HBE14o-) at low passage number were seeded into 24-well collagen coated plates (BD Biosciences®, San Diego, Calif.) and allowed to grow at 37° C. in 5% $CO_2$ to confluence in DMEM-F12 complete medium containing 10% fetal bovine serum. To prepare the cells for panning, the medium was removed and replaced with DMEM-F12 with no serum (F12i) and incubated at 37° C. for 1.5 hours. Then the F12i was removed and replaced with 500 μl/well of 1% BSA in DPBS and incubated at 37° C. for 60 minutes. Just before panning the DPBS was removed and the cells were rinsed with 500 μl of TBS. A 50 ul aliquot of the naïve T7Select® Trp cage library was combined with 160 μl of TBS and added to the cells followed by incubation at 4° C. for 60 minutes with gentle rocking. The unbound portion of the phage library was removed by 25 washes with 500 μl of TBS. Bound phage were eluted by adding 200 μl of a BLT5403 culture grown to $OD_{600}$=1.0 in M9LB followed by incubating at room temperature for 15 minutes. Eluted phage were added to 20 ml of the BLT5403 culture and amplified by incubation at 37° C. for two to three hours until cell lysis was observed. The amplified phage was concentrated with PEG/NaCl and resuspended in 200 μl DPBS. Subsequent rounds of panning were performed using 20 μl of concentrated phage from the previous round. In the second round unbound phage were removed by washing with TBS containing 0.1% Tween and in the third round TBS with 0.3% Tween was used. After three rounds of panning, well isolated plaques of eluted phage were selected for nucleotide sequencing.

Panning Against HUVEC and HepG2 Cells:

Cells were seeded onto 24-well plates and grown at 37° C. in 5% $CO_2$ to confluence before panning with the M13 libraries (PhD-7, PhD-12, PhD-C7C) and the T7Select® T-3 library. HUVEC cells were grown on collagen-coated plates using CS-C complete medium. HepG2 cells were grown on uncoated plates using DMEM medium. Each cell type was used to isolate peptides that bound specifically to that cell type (target cell type). In addition, each cell type functioned as a negative screen (subtraction step) for phage displaying peptides that bound to the other cell type (non-target cell type). This subtraction step removed phage that displayed peptides capable of binding to both cell types and allowed for greater selectivity in isolating cell specific binding peptides. To perform this subtraction step, the phage library was initially incubated with the non-target cell type where unbound phage were isolated and subsequently used in the panning process with the target cell type. The cells used for subtraction were rinsed with one ml of PBS and 10 μl of phage library was mixed with 200 μl of PBS and added to the non-target cells, then binding was permitted for 60 minutes at 4° C. with gentle rocking. After subtraction, the unbound portion of the phage library was recovered and transferred to wells containing rinsed cells to be used as the target for panning followed by incubation for 15 minutes at 4° C. with rocking. Unbound phage were removed from the target cells by ten washes with one ml of PBS-0.5% Tween-20 (PBS-T). Target cells were lysed by adding 200 µl water and pipetting repeatedly to recover bound and internalized phage, Phage in the lysate were amplified by transferring the entire volume to 20 ml of LB broth containing one ml of a fresh overnight culture of host bacteria (ER2738 for M13 and BLT5403 for T7) and incubating for 5 hours at 37° C. with vigorous shaking. The amplified phage were concentrated with PEG as described above and resuspended in 200 µl PBS. Subsequent rounds of subtraction and panning were performed using 20 µl of concentrated phage from the previous round.

Example 2

Expression Vector Selection

The present example demonstrates that the T7Select® vector 10-3b containing the Trp cage TC3b nucleotide sequence yields the lowest percentage of progeny phage that express a mutant form of the Trp cage TC3b fusion protein. Further, the 10-3b vector exhibits an average copy number of 5 to 15 capsid-fusion proteins displayed per phage. In light of these results, the T7Select® vector 10-3b was chosen for constructing the remaining phage libraries in the instant application.

Novagen's T7Select® system was designed to display peptides with a free C-terminus from the phage capsid protein (gp 10). In the present example, it was used to display Trp cage fusion proteins. Three T7Select® vectors were used that vary by the average number of number of capsid-fusion proteins displayed per phage; 415-1b (average copy number=415), 10-3b (average copy number=5-15) and 1-1b (average copy number=0.1-1). In order to determine if the Trp cage protein TC3b could be displayed on bacteriophage T7, oligos TC3b (+) and TC3b (−) were annealed and inserted into the three T7Select® vectors. DNA from phage selected from several well-isolated plaques was analyzed by nucleotide sequencing, which was used to deduce the amino acid sequence for each phage clone. The amino acid sequence from each clone generated from the three different T7Select® vectors was compared to the original (expected) TC3b deduced amino acid sequence. This comparison revealed a high percentage of TC3b fusion protein mutants for the phage carrying the TC3b nucleotide sequence in the 415-1b vector (⅞) and a low percentage of TC3b fusion protein mutants for the phage carrying the TC3b nucleotide sequence in both the in the 10-3b (1/10) and the 1-1b (⅕) vectors. The expected (TC3b) nucleotide sequence and deduced amino acid sequence and examples of the mutant nucleotide sequences originating from the TC3b sequence and deduced amino acid sequences derived from the three different T7Select®vectors (415-1b, 10-3b and 1-1b; see Table 1). Table 1 also shows the amino acid sequences for exendin-4 (scaffold protein used as a template sequence to generate the random Trp cage peptide library) and TC5b. As shown in the Table 1, the expected sequence and observed mutant sequences revealed single base changes in the mutant sequences that resulted in nonsense or missense mutations, which prevented expression of the Trp codon. For example, the 71-121-43 clone inserted in the 10-3b T7Select® vector, there is a deletion of a 't' at position 16 of the original TC3b nucleotide sequence and insertion of a 'c' between 'a' and 'g' located at positions 40 and 41 of the original TC3b nucleotide sequence. Also, the 71-121-5 clone inserted in the 1-1b T7Select® vector, there is a deletion of a 'c' at position 31 of the original TC3b nucleotide sequence.

Thus, the medium valency vector 10-3b was used for the remaining library work because it produces less number of mutants than the T7Select® 415-1b vector while producing a higher average copy number than the 1-1b vector.

TABLE 1

Exendin-4, TC5b, TC3b and Representative TC3b Sequences Derived
From the Three Different T7Select ® Expression Vectors

| Vector/Clone | Deduced Amino Acid Sequence and Nucleotide Sequence |
| --- | --- |
| Exendin-4 (residues 20-39) | R L F I E W L K N G G P S S G A P P P S (residues 20-39 of SEQ ID NO: 1) |
| TC5b Original Sequence | N L Y I Q W L K D G G P S S G R P P P S (SEQ ID NO: 530) <br><br> AAT TCG GCA GCT GCG AAT TTG TAT ATT CAG TGG CTT AAG GAT GGT GGT CCT TCG TCG GGG CGG CCT CCG CCA AGT TAA A (SEQ ID NO: 9) |
| TC3b Original Sequence | N L F I F W L K N C G P S S G A P P P S stop (SEQ ID NO: 14) <br><br> AAT TTA TTT ATC GAA TGG CTC AAA AAT GGT GGT CCT TCC AGT GGT GCT CCT CCC CCT TCC TAA (SEQ ID NO: 7) |
| 415-1b A1 Clone | N stop <br><br> AAT TGA TTT ATC GAA CGG CTC AAA AAT GGT GGT CCT TCC AGT GGT GCT GCT CCC CCT TCC TAA (SEQ ID NO: 15) |
| 415-1b A2 Clone | N L F I E stop (SEQ ID NO: 16) <br><br> AAT TTA TTT ATC GAA TAG CTC AAA AAG GGT GGT CCT TCC AGT GGT GCT CCT CCC CCT TCC TAA (SEQ ID NO: 17) |

TABLE 1-continued

Exendin-4, TC5b, TC3b and Representative TC3b Sequences Derived From the Three Different T7Select ® Expression Vectors

| Vector/Clone | Deduced Amino Acid Sequence and Nucleotide Sequence |
|---|---|
| 415-1b<br>Ai5 Clone | N L F I E S (SEQ ID NO: 18)<br><br>AAT TTA TTT ATC GAA TCG CT N TNT AAA G GGT GGT CCT TCC (SEQ ID NO: 19) |
| 10-3b<br>71-121-43<br>Clone | N L F I E G S K M V V L P R G A P P P S stop (SEQ ID NO: 20)<br><br>AAT TTA TTT ATC GAA GGC TCA AAA ATG GTG GTC CTT CCA CGT GGT GCT CCT CCC CCT TCC TAA (SEQ ID NO: 21) |
| 1-1b<br>71-121-5<br>Clone | N L F I E W L K N G G L P V V L L P L P (SEQ ID NO: 22)<br><br>AAT TTA TTT ATC GAA TGG CTC AAA AAT GGT GGT_CTT CCA GTG GTG CTC CTC CCC CTT CCT AA (SEQ ID NO: 23) |

Example 3

Trp Cage Fusion Protein is Displayed on the Phage Capsid

The present example demonstrates that phage constructed with the T7Select® vector 10-3b containing the TC5b nucleotide sequence display the Trp cage protein on their capsid (refer to Table 1 for the TC5b sequence).

To demonstrate that a Trp cage protein was actually displayed on the phage capsid, a pair of oligos designed to encode the Trp cage protein TC5b were annealed and cloned into the T7Select® vector 10-3b. Display of the Trp cage protein on the phage capsid was demonstrated by ELISA using antibody AB167 (rabbit IgG) which was raised against peptide PN0522 (refer to Example 1, "Production of Antibody AB167" for amino acid sequence of the peptide) and binds to the Trp cage protein. Two negative controls were used. One was the 10-3b vector with no insert and the other was the 10-3b vector containing the S-Tag. All phage were incubated with the AB167 antibody at 1×10⁶, 1×10⁷ and 1×10⁸ phage per well for the ELISA. The results from the ELISA are as follows: signal was detected from phage containing the TC5b insert (10-3b/TC5b) and, as expected no signal was detected from the negative control phage containing the 10-3b without an insert (10-3b/No peptide) or the negative control phage displaying a 15-mer linear peptide (10-3b/S-Tag). These data indicate that the Trp cage protein was displayed on the phage capsid.

In addition, to show that the Trp cage protein was displayed as a result of fusion to the phage capsid protein, proteins from phage lysate, representing phage generated with the 10-3b vector and the TC5b insert, the S-Tag® insert or no insert, were separated by SDS-PAGE electrophoresis and transferred to a membrane for Western blot analysis with the AB167 antibody.

For the Western blot analysis of Trp cage TC5b expressed with the 10-3b T7Select® vector, proteins in lysates from phage infected cells were separated by SDS-PAGE in Coomasie stained gel. The lysates were prepared from cells that were infected with T7 displaying either; no peptide (10-3b), Trp cage TC5b (TC5b), or the S•Tag® peptide (S-Tag). BLT5403 contained lysate from uninfected cells. The Western transfer showed that only the lysate from infection by phage displaying Trp cage TC5b contained a protein that bound the Trp cage specific antibody AB167. MagicMark® XP Western Protein Standards (Stds) were used.

The Western blot analysis showed that the AB167 antibody bound to a protein on the membrane that corresponded to the lane containing protein isolated from phage generated with the 10-3b vector having the TC5b insert. In contrast, the AB167 antibody did not bind to any protein isolated from phage generated with the 10-3b vector with no insert, the 10-3b vector having the S-Tag® (15-mer peptide) or in extracts of uninfected host bacteria (BLT5403). The molecular weight of the protein identified with the AB167 antibody is consistent with the predicted molecular weight of the Trp cage-phage capsid protein fusion, i.e., 39,640 daltons (376 amino acids). Western analysis using an antibody against the S-Tag® instead of the Trp cage, resulted in detection of a band only in the S-Tag® lane which was similar in size to the Trp cage—phage capsid protein fusion.

These data indicate that the TC5b Trp cage protein is displayed on the phage capsid and that this presentation by the phage was a result of the fusion of the TC5b Trp cage protein with the phage capsid protein.

Example 4

Display of the Trp Cage Protein by Phage Reduces Phage Progeny Production by 50%

The present example demonstrates that the average yield of progeny phage produced per infected cell is reduced by 50% when phage display the Trp cage protein. One-step growth experiments were conducted in E. coli BLT 5403 to determine if display of the Trp cage protein affected the production of progeny phage as measured by the average burst size. The affect on progeny size was measured for three different phage, all of which were generated with the T7Select® 10-3b vector. The phage labeled 10-3b displayed no peptide, the phage labeled 10-3b/S-Tag displayed the 15 amino acid S-Tag protein and the phage labeled 10-3b/TC5b displayed the Trp Cage protein TC5b. The one-step growth data is shown below in Table 2. The data from three independent one-step growth experiments indicated that while the average number of infected cells were similar for all phage tested, the burst size (a ratio of progeny phage to infected cells) of 10-3b/TC5b was 50% lower than that of the 10-3b phage (no peptide displayed). Further, phage displaying the linear 15 amino acid peptide S-Tag (10-3b/S-Tag) exhibited a burst size between that of the 10-3b/TC5b phage and the 10-3b phage.

TABLE 2

Average Burst Size Comparison

| Parameters | Phage Tested | | |
|---|---|---|---|
| | 10-3b | 10-3b/S-Tag | 10-3b/TC5b |
| Number of Infected Cells | $3.56 \times 10^8$ | $3.88 \times 10^8$ | $4.20 \times 10^8$ |
| Average Burst Size (n = 3) | 216.9 | 157.1 | 104.4 |
| STDEV | 20.2 | 23.3 | 11.1 |

These data indicate that displaying the Trp cage protein reduces the average yield of progeny phage produced per infected cell by 50%.

Example 5

Trp Cage Master Library (T-3) Construction

The present example illustrates the method used to construct a degenerate phage display library based on the Trp cage motif of the exendin-4 protein (Trp Cage Master Library or T-3 Master Library). The display library consists of phage containing the T7Select® 10-3b vector with the T-3 insert. The T-3 insert encodes for a modified Trp cage scaffold protein whereby 7 different amino acid positions of the protein are encoded by codons having 32-fold degeneracy. This level of degeneracy provided a library complexity approaching $1.28 \times 10^9$ based on a total of $1.6 \times 10^9$ packaged primary phage clones.

A phage library capable of displaying the modified Trp cage protein with 7 different randomized positions on bacteriophage T7Select® 10-3b was produced by the primer extension method. The primer T-3 (+) and template T-3 (−) oligonucleotides were designed to produce an insert in T7 such that the coding strand would include codons commonly utilized by E. coli and phage T7 for the invariable amino acids and the degenerate codon NNK at the seven randomized positions where N=G/A/T/C and K=G/T. Utilizing the NNK codon reduced the number of possible amino acid codons at the randomized positions from 64 to 32 to provide a more uniform distribution of amino acids and eliminate all the stop codons except TAG (amber). The T7Select® 10-3b vector is designed to display an average of 5 to 15 copies of a C-terminal protein fusion on the phage capsid protein (gp10B). The TC5b mutant of the Trp cage protein served as the scaffold for the library. Modifications to the Trp cage protein as follows: An aspartate (D) residue was substituted for $N_1$ as a helix capping residue. Three alanine (A) residues were added to the N-terminus to increase helical propensity and stabilize the protein. Lastly, the ochre stop codon TAA was placed after the last randomized amino acid resulting in the following 23 amino acid protein which was fused to the phage gp10B capsid protein. The amino acid sequence below represents the modified Trp cage protein whereby X represents the randomized position of an amino acid encoded by a degenerate codon.

(SEQ ID NO: 4)
A A A D X Y X Q W L X X X G P X S G R P P P X *

The reasons for selecting the positions occupied by the amino acids encoded by a degenerate codon are two-fold. First, the amino acids that occupy these positions are not required for protein folding and, secondly, the amino acids in these positions are exposed on the outside of the folded protein as determined by NMR structure and thus free to interact with potential binding targets. The NMR structure of Trp cage TC5b was NCBI accession number 1LY_A. Based on analysis of the Trp cage sequence that indicated which amino acids must be conserved for Trp cage folding, seven positions that were nonconserved and solvent exposed were chosen for randomization in the library.

A total of $1.6 \times 10^9$ packaged primary phage clones were obtained in order to provide library complexity approaching the number of possible combinations ($20^7 = 1.28 \times 10^9$). The primary clones were amplified once before purification by a CsCl step gradient. The recovered phage served as the Trp Cage Master Library designated T-3. The total volume of T-3 was 4.5 ml and contained $1.5 \times 10^{13}$ pfu, therefore the library contained about $9.4 \times 10^3$ copies of each primary phage clone.

To determine the expected proportion of the library that would express the Trp cage as designed, DNA from 100 primary phage clones was sequenced. Among the 100 clones, 64% contained the expected sequence (8% contained the stop codon TAG in one of the randomized positions) and 36% contained frameshift mutations.

Example 6

Mutant and Non-Mutant Phage Genotypes are Stable

The present example demonstrates that genotype of individual phage clones remains unchanged during the process of library amplification. Specifically, progeny phage maintain the same genotype as their corresponding parental phage.

To determine if amplification of the library would affect the phage subpopulations, the stability of non-mutant and mutant primary phage clones was examined by selecting one of each type and infecting BLT5403 cells with each phage separately or mixed in a 1:1 ratio. When progeny from the infections were examined by nucleotide sequencing, surprisingly, the mutant and non-mutant phage only produced progeny (10/10 for each) with exactly the same nucleotide sequence as the corresponding parental phage. When 20 progeny plaques were picked and sequenced from the mixed infection, there were 9 mutant sequences and 11 non-mutant sequences, indicating no apparent growth advantage to the mutant or non-mutant phage. In each case, the mutant and non-mutant sequences matched the sequences of the corresponding parental phage.

These data from the infections with a single parental phage, either mutant or non-mutant, suggest that the mutant and non-mutant genotypes are stable. Moreover, the mixed infection produced progeny in a ratio nearly equal to the ratio of the input parental phages, which suggests that neither the mutant nor the non-mutant phage have an apparent growth advantage.

Example 7

Characterization of the Trp Cage Master Library (T-3)

The present example characterizes representative display peptides isolated from the Trp Cage Master Library (T-3). This characterization includes determining the number of display peptides with either an expected or an unexpected deduced amino acid sequence, (an unexpected amino acid sequence is one that cannot be derived from the original T-3 nucleotide sequence without mutation), determining what amino acids occupy the 7 amino acid positions (randomized positions) within the peptide encoded by degenerate codons and the frequency of those amino acids at those positions and finally the amino acid diversity of those same 7 randomized positions.

After amplifying the library, the naïve T-3 Master Library was characterized by selecting 109 random individual clones for nucleotide sequencing to deduce the amino acid sequence of the display peptides. Based on the differences observed in the sequences among the 109 clones, the display peptides were categorized into three different groups, "non-mutants," "mutants" and "stops." The "non-mutant" category contained 50 clones (46%) with deduced amino acid sequences that contained the expected the Trp cage scaffold with the 7 different randomized positions, each one of those 7 position occupied by one of the predicted amino acids that could be derived from the inserted degenerate codon. The "stops" category contained 18 clones (16%) with the designed Trp cage scaffold, but the display peptides in this category had a stop codon in one of the 7 designated randomized positions. Lastly, the "mutant" category contained 41 (38%) clones with amino acid sequences that did not conform to the expected (designed) sequence.

All mutations observed were single base deletions or insertions that resulted in missense or nonsense mutants. The two most common types of mutations, Type I and Type II, are described below and illustrated in Table 3. The most common mutation observed (Type I) was the deletion of a guanine (g) at the beginning of the coding sequence of the fusion protein where the capsid protein ends and the Trp cage protein starts. An example of this type of mutant is shown below in Table 3 where the single base deletion, indicated by "_" changed the reading frame and resulted in a sequence encoding a truncated form of the Trp cage protein.

The second most common mutant type (Type II) was the insertion of a cytosine (c) located between the codons for the sixth and seventh degenerate positions. An example of this type of mutant is shown below in Table 3. This type of mutant usually altered the reading frame destroying the originally designed stop codon and resulted in the use of an alternate downstream stop codon. Consequently, the altered amino acid sequence of the protein prevented the formation of the Trp cage.

TABLE 3

Two Most Common Mutants Observed in the T-3 Master Library

| Sequence Description | Amino Acid Sequence and Nucleotide Sequence |
|---|---|
| T3 Designed (Expected) | N A A A D X Y X Q W L X X X G P X S G R P P P X (SEQ ID NO:): 531)<br><br>AAT TCG GCA GCA GCA GAT NNK TAC NNK CAG TGG TTA NNK NNK NNK GGT CCT NNK TCT GGT CGT CCT CCC CCC CCC TAA (SEQ ID NO: 24) |
| Mutant Type I | N S Q Q Q I R T C S G * (SEQ ID NO: 25)<br><br>AAT TCG _CA GCA GCA GAT CCC TAC TTG CAG TGG TTA A (SEQ ID NO: 26) |
| Mutant Type II | N S A A A D R Y H Q W L R L S G P P S G R P S P P V T S L R P H S S N * (SEQ ID NO: 27)<br><br>AAT TCG GCA GCA GCA GAT AGG TAC CAT CAG TGG TTA AGG CTT TCT GGT CCT CCG TCT GGT CGT CCC TCC CCC CCC GTA ACA AGC TTG CGG CCG CAC TCG ACT AAC TAG (SEQ ID NO: 28) |

The next analysis assessed the frequency of the amino acids derived from the 7 different degenerate codons within the Trp cage protein of 50 non-mutant clones. Table 4 below summarizes the amino acid frequency data. The numbers identifying the position of an amino acid encoded by a degenerate codon within Table 4 (column entitled "Randomized Position within Trp Cage Protein") corresponds to the following diagram of the Trp cage protein:

AAADX$_1$YX$_2$QWLX$_3$X$_4$X$_5$GPX$_6$SGRPPPX$_7$     (SEQ ID NO: 4)

whereby, $X_1$ represent the random amino acid found in position #1 (which is the fifth position from the left in SEQ ID NO: 4), $X_2$ represents the random amino acid found in position #2, so on and so forth.

Confidence interval bounds for the frequency of amino acids in each of the 7 randomized positions were determined using the Clopper-Pearson Method. This method was used to determine the exact confidence bounds for a binomially distributed random variable based on the use of a 32 codon genetic code. An adjustment was made to the usual 95% confidence level based on the simplest Bonferroni correction for the 7 positions [100×(1−0.05/7)=99.3%]. The resulting bounds are as follows: 0 to 7 for amino acids encoded by only one codon, 0 to 10 for amino acids encoded by two codons, and 1 to 13 for amino acids encoded by three codons. All amino acid frequencies fall within the expected bounds except the arginine (R) at position 5 which was zero, but was expected to be at least one with a confidence of 99.3%.

TABLE 4

Frequency of Amino Acids in the Trp Cage Protein at Positions Encoded by Degenerate Codons (based on 50 non-mutant clones)

| Type of Amino Acid | Amino Acid | Randomized Position within Trp Cage Protein | | | | | | | Total | Frequency (%) | M13 Ph.D.-C7C Frequency (%) | Codons available |
|---|---|---|---|---|---|---|---|---|---|---|---|---|
| | | 1 | 2 | 3 | 4* | 5 | 6 | 7 | | | | |
| Basic | H-his | 4 | 3 | 0 | 4 | 4 | 2 | 0 | 17 | 4.9 | 6.9 | 1 |
| | R-arg | 4 | 5 | 4 | 7 | 0 | 2 | 4 | 26 | 7.4 | 4.3 | 3 |
| | K-lys | 0 | 0 | 0 | 2 | 2 | 2 | 2 | 8 | 2.3 | 3.8 | 1 |
| Non-polar | I-ile | 0 | 4 | 1 | 1 | 0 | 2 | 0 | 8 | 2.3 | 2.1 | 1 |
| | F-phe | 0 | 2 | 0 | 0 | 0 | 1 | 2 | 5 | 1.4 | 2.1 | 1 |
| | L-leu | 8 | 8 | 4 | 5 | 4 | 5 | 7 | 41 | 11.7 | 9.6 | 3 |
| | W-trp | 1 | 2 | 0 | 0 | 3 | 0 | 1 | 7 | 2 | 1.9 | 1 |
| | A-ala | 7 | 2 | 4 | 4 | 4 | 2 | 4 | 27 | 7.7 | 6.5 | 2 |
| | M-met | 1 | 0 | 0 | 0 | 2 | 3 | 1 | 7 | 2 | 3.3 | 1 |
| | P-pro | 5 | 5 | 6 | 5 | 8 | 8 | 6 | 43 | 12.3 | 10.7 | 2 |
| | V-val | 4 | 0 | 3 | 3 | 2 | 2 | 0 | 14 | 4 | 1.9 | 2 |
| Polar | C-cys | 0 | 1 | 1 | 0 | 3 | 2 | 0 | 7 | 2 | 0 | 1 |
| | N-asn | 0 | 0 | 2 | 3 | 2 | 0 | 4 | 11 | 3.1 | 6.4 | 1 |
| | G-gly | 2 | 2 | 1 | 1 | 1 | 2 | 1 | 10 | 2.9 | 2.2 | 2 |
| | S-ser | 4 | 5 | 11 | 8 | 2 | 3 | 4 | 37 | 10.6 | 8.6 | 3 |
| | Q-gln | 3 | 1 | 1 | 2 | 2 | 1 | 5 | 15 | 4.3 | 7.1 | 1 |
| | Y-tyr | 3 | 2 | 2 | 2 | 0 | 0 | 5 | 14 | 4 | 2.4 | 1 |
| | T-thr | 3 | 6 | 7 | 2 | 7 | 9 | 2 | 36 | 10.3 | 13.1 | 2 |
| Acidic | D-asp | 1 | 1 | 3 | 1 | 2 | 3 | 2 | 13 | 3.7 | 4.1 | 1 |
| | E-glu | 0 | 1 | 0 | 0 | 2 | 1 | 0 | 4 | 1.1 | 3.1 | 1 |
| All | Basic | 8 | 8 | 4 | 13 | 6 | 6 | 6 | 51 | 14.6 | 15 | 5 |
| | Non-polar | 26 | 23 | 18 | 18 | 23 | 23 | 21 | 152 | 43.4 | 38.1 | 13 |
| | Polar | 15 | 17 | 25 | 18 | 17 | 17 | 21 | 130 | 37.1 | 39.8 | 14 |
| | Acidic | 1 | 2 | 3 | 1 | 4 | 4 | 2 | 17 | 4.9 | 7.2 | 2 |

Lastly, the amino acid sequences deduced from the 50 non-mutant clones were analyzed using the DIVAA program available at the RELIC Web site (http://relic.bio.anl.gov/) to determine the diversity of the amino acids by position in the library. The results of the DIVAA program show that the diversity of the randomized positions range from 0.55 to 0.75. For comparison, data available at the Web site was used to generate a plot of the diversity for the M13 Ph.D.-C7C library (a purchased constrained phage display library). The Trp cage library has diversity that is comparable to the constrained M13 Ph.D.-C7C library at all positions except for position #3, where the Trp cage library exhibited lower diversity. The average diversity for the Trp cage library was 0.67 compared to 0.70 for PhD-C7C.

These data derived from use of the DIVAA program shows that the Trp cage library exhibits an average diversity of 0.67, which is similar to the average diversity of 0.70 for the well characterized constrained M13 PhD-C7C library.

Example 8

Panning Against the Streptavidin Receptor with the Trp Cage Master Library (T-3) Resulted in the Excepted HPQ Motif The present example demonstrates that the Trp Cage Master Library (T-3) can be used to isolate a specific protein binding motif based on a selected target. The streptavidin receptor is commonly used as a model target system for phage display libraries. Screening a phage display library for peptides that specifically bind to the streptavidin receptor typically yields the known His-Pro-Gln (HPQ) motif. Therefore, the streptavidin receptor was used as a target to assess the naïve Trp cage library for display of the HPQ motif in a limited panning experiment using $1.2 \times 10^9$ pfu of the amplified library before final purification by CsCl. After panning the Trp cage library against streptavidin for three rounds, a small number of clones were selected for nucleotide sequencing. Multiple rounds of panning with the streptavidin receptor resulted in 10 clones, three of which were mutant. Two out of the seven non-mutant clones contained the expected HPQ motif, YLHPQHA (SEQ ID NO: 29) and SRHPQWA (SEQ ID NO: 30). The amino acid sequence of the remaining five clones are as follows: LRALCQT (SEQ ID NO: 536); HRLGLGC (SEQ ID NO: 537); KTSIAQQ (SEQ ID NO: 538); LNTHSRN (SEQ ID NO: 539) and AMRYHF (SEQ ID NO: 540).

These data show that a motif with high binding affinity to a specified target can quickly be obtained from panning with the Trp cage library.

Example 9

Suppression of the TAG Stop Codon in the Trp Cage Coding Sequence of T7Select® Phage The present example demonstrates that a TAG stop codon within the Trp cage coding region of T7Select® phage is suppressed by propagation in a bacterial TAG stop codon suppresser strain. Suppression of the TAG stop codon within the Trp cage coding sequence prevents formation of truncated forms of the Trp cage protein due to creation of a TAG stop codon from mutation.

Since phage display systems typically encode randomized amino acids using the reduced 32 codon genetic code which includes one stop codon, TAG, a suppressor host is used to prevent premature peptide termination resulting from incorporation of the stop codon. Because a suppressor host is not available for the T7Select® system, a host capable of suppressing the TAG stop codon while limiting the number of peptides displayed on the T7 phage capsid was obtained by transforming competent cells of the carbenicillin sensitive (Carb$^S$) strain C600 (which contains suppressor mutation supE44 that inserts a glutamine at TAG codons) with purified plasmid pAR5403 which encodes carbenicillin resistance (Carb$^R$) and provides excess 10A capsid protein to limit the number of displayed peptides. A clone of C600 transformed with pAR5403 was isolated as a Carb$^R$ colony and designated C600CR. Plasmid transformation was confirmed by agarose gel electrophoresis of purified plasmid DNA from cell lysates which showed that the pAR5403 plasmid donor strain BLT5403 contained a single plasmid estimated to be 3.0 Mdal by comparison to the relative mobility of reference plasmids obtained from *E. coli* V517. The parental recipient strain C600 contained no detectable plasmid DNA while the Carb$^R$ transformant C600CR contained a plasmid the same size as pAR5403. Presence of gene 10A in the transformed host was confirmed by PCR.

For this agarose gel electrophoresis, transformation of plasmid pAR5403 into the supE44 expressing host C600 was demonstrated by comparing plasmid DNA extracted from the following *E. coli* strains; (A) V517, a plasmid reference standard, (B) BLT5403, plasmid donor strain, (C) C600CR, transformant, and (D) C600, plasmid-free recipient.

Growth of phage containing the insert encoding Trp cage TC5b in the host BLT5403 which limits expression to 5 to 10 copies of the peptide, produced clones displaying the expected sequence NLYIQWLKDGGPSSGRPPPS (SEQ ID NO: 530) with a low frequency of mutations (one out of twelve sequenced clones). When the same phage clones were grown in the host BL21 which does not limit the expression of the peptide, mutants were obtained at high frequency (six out of six sequenced clones). Some of the mutant clones contained the TAG stop codon within the Trp cage sequence and were expected to result in the display of truncated peptides. Two nonsense mutants, E7 which contained a TAG stop codon at Tyr-3 of the Trp cage sequence NL*IQWLKDGGPSSGRPPPS (SEQ ID NOs: 588 and 534, respectively in order of appearance) and E12 which contained a TAG stop codon at Trp-6 of the Trp cage sequence NLYIQ*LKDGGPSSGRPPPS (SEQ ID NOs: 535 and 553, respectively in order of appearance), were chosen to test the effectiveness of the suppressor host C600CR by ELISA. Each mutant and phage clone B1, which displays TC5b without a stop codon, was grown in the nonsuppressor strain BLT5403 and the suppressor strain C600CR. T7Select® 10-3b which does not have a displayed peptide was grown in BLT5403. Phage displaying Trp cage TC5b were detected using rabbit IgG polyclonal antibody AB167 raised against TC5b and demonstrated to bind to phage displaying the TC5b peptide by Western (see above). Since AB167 is a polyclonal antibody, some binding to the truncated peptides of E7 and E12 was expected with possibly greater binding to E12 because it is three residues longer than E7.

Phage ELISA was performed for demonstration of TAG suppression. Binding of antibody AB167 to T7Select® 10-3b phage grown in the nonsuppressor host BLT5403 (B) was compared with binding to phage grown in the suppressor host C600CR. (C). The comparison included phage without a displayed peptide grown in the nonsuppressor host (T7/B) and phage displaying TC5b grown in both hosts (B1/B and B1/C). Binding of the antibody to phage mutants E7 and E12 displaying truncated Trp cages grown in B (E7/B and E12/B, respectively) was related to antibody binding to phage clone B1 displaying the full length Trp cage on a percentage basis. The phage mutants grown in C (E7/C and E12/C) were likewise related to B1 grown in C. Results represent the average of triplicate wells.

As shown in Table 5, the ELISA indicated that the antibody detected display of the TC5b peptide when B1 was grown in either host (B1/B and B1/C), and there was minimal binding of the antibody to phage T7Select® 10-3b (T7/B) that has no displayed peptide. The percentage of binding to E12 after growth in BLT5403 (E12/B) was numerically lower than when grown in C600CR (E12/C), but the difference was not significant (P>0.1). Antibody binding to mutant E12 was lower than the binding to B1 regardless of the host. Antibody binding to mutant E7 was significantly higher (P<0.01) when grown in the suppressor C600CR (E7/C) compared to growth in the nonsuppressor BLT5403 (E7/B) and both exhibited lower binding than B1. The results from E7 indicate that C600CR was able to suppress the codon TAG in the T7Select phage. Values lower than B1 were expected since suppression by supE44 is not 100% efficient.

TABLE 5

| Percent Antibody Binding | |
|---|---|
| Phage (10$^8$ pfu/ml) | Percent antibody binding |
| T7/B | 15 |
| B1/C | 100 |
| B1/B | 100 |
| E7/C | 65 |
| E7/B | 32 |
| E12/C | 62 |
| E12/B | 50 |

Example 10

Isolation of Select Display Peptides after Cell Specific Panning Against with the Trp Cage Master Library (T-3) and M13 Phage Libraries The present example demonstrates that panning against specific cell types with the Trp Cage Master Library (T-3) and the M13 phage display libraries (PHD-7; PHD-12 and PHD-C7C) results in the novel exemplary display peptides of the present invention. Of note, display peptides isolated from panning with the Trp cage Master Library (T-3) results in peptides approximately 23 amino acids in length. The display peptides isolated from panning with the M13 libraries results in peptides approximately 7 to 12 amino acids in length. The three different cell types used in this example to isolate peptides that exhibited cell specific binding properties are HepG2, HUVEC and 16HBE140-cells.

Three methods of panning with HepG2 and HUVEC cells were used to isolate peptides that exhibited cell specific binding properties to those cell types. Method I was designed to select for cell-uptake peptides that bind to a specific cell type and enter the cell via endocytosis. Briefly, Method I entails incubating phage for 15 minutes with a specific cell type, for example HepG2 or HUVEC cells, and then inactivating any phage remaining bound to the cell surface. Inactivation results in phage incapable of infecting bacteria and, therefore, phage displaying peptides that do not facilitate cell entry are not selected. Following inactivation, target cells are lysed and internalized phage are released. Phage clones are expanded and then analyzed by nucleotide sequencing. Both Method 2 and Method 3 were designed to select for cell surface specific binding peptides. However, Method 3 employs more stringent conditions in order to select display peptides that exhibit cell specific binding. Both methods incubate phage with the target cell. However, Method 3 adds a subtraction step whereby the phage are incubated first with non-target cells and then those phage that do not bind to the non-target cells are removed and incubated with the target cells. Phage that bind to the target cells are then collected and expanded and analyzed by nucleotide sequencing. An example of this methodology is when panning against HUVECs, the phage libraries are first subtracted against HepG2 cells and when panning against HepG2 cells the phage libraries are subtracted against HUVEC cells.

The naïve Trp cage library and three M13 libraries were panned against HUVEC or HepG2 (liver cells) cells using Method 1, Method 2 or Method 3 in order to obtain cell specific peptides. Table 5 illustrates the exemplary display peptides of the present invention isolated from the Trp Cage Master Library (T-3) or one of the M13 phage display libraries (PHD-7; PHD-12 and PHD-C7C) that were screened for HepG2 cell selective binding. Table 6 illustrates the exemplary display peptides of the present invention isolated from the Trp Cage Master Library (T-3) or one of the M13 phage display libraries (PHD-7; PHD-12 and PHD-C7C) that were screened for HUVEC cell selective binding. The amino acid sequences listed in the Tables 6 and 7 below were isolated after three to five rounds of panning against the targeted cell type (HUVEC or HepG2). The number followed by the letter 'X' in parentheses found after an amino acid sequence in the Tables below indicates the frequency at which that amino acid sequence was isolated during panning (i.e., the panning resulted in multiple peptides with the same amino acid sequence). The "*" in an amino acid sequence represents a stop codon.

TABLE 6

HepG2 Selected Peptides

| SEQ ID NO: | Display Peptide Amino Acid Sequence - HepG2 Selected Peptides |
|---:|---|
| 31 | SPPLSGT |
| 32 | NYLTSPL |
| 589 & 33 | F*MPLRH |
| 34 | AHTLPPW |
| 35 | TAVPLMS |
| 36 | YSTPYTS |
| 37 | SPPMAVP |
| 38 | NTLPSQT |
| 39 | VPNIPYS |
| 40 | GGAEIRPAHVMF |
| 41 | *IPHPGREVIQH |
| 42 | SDGSMAYKRSTL |
| 43 | TPYRTLTPAGIN |
| 44 | SHSKFDTHRPDL |
| 45 | KPLNVNTHQATR |
| 46 | AHPSSQMSSPSP |
| 47 | PPTTKQM |
| 48 | PVTTLKA |
| 49 | NSLNYHL |
| 50 | PPRQSLH |
| 51 | TTFPRQA |
| 52 | KNQHPML |
| 53 | PYPMTGT |
| 54 | GSHPLAT |
| 55 | NSSSSSQ |
| 56 | STMDPIL |
| 57 | TYKPSPL |
| 58 | TTVLTPK |
| 59 | HAIYPRH |
| 60 | DTGSSTI |
| 61 | NLQEFLF (18X) |
| 62 | TPATSPF |
| 63 | KYSTALT |
| 64 | MSPNKQL |
| 65 | FSKNSPA |
| 66 | SSKEPKA |
| 67 | TGTMIIPHM |
| 68 | SPHYRAY |
| 69 | STRMHPD |
| 70 | RPTPFHH |
| 71 | SAPNLNALSAAS |
| 72 | LLADTTHHRPWT |
| 73 | VLPxKPMRQPVA |
| 74 | GVMTYPYSRAYH (2X) |
| 75 | AHHNSWKAKHHS |
| 76 | HYLSPAPASLRP |
| 77 | SSAQNYAWLAPR |
| 78 | AHHYTATPTIQS |
| 79 | NVSSAWL |
| 80 | YQTMARL |
| 81 | QKHNDAA |
| 82 | DTNSQKM |
| 83 | HNPPMTS |

TABLE 6-continued

HepG2 Selected Peptides

| SEQ ID NO: | Display Peptide Amino Acid Sequence - HepG2 Selected Peptides |
|---|---|
| 84 | QNIIMSP |
| 85 | HARLPSA |
| 86 | AxYMxxK |
| 87 | STMDPIL |
| 88 | EPLQLKM |
| 89 | HAIYPRH |
| 90 | GETRAPL (8X) |
| 91 | AHHW4SWKAKHHS (11X) |
| 92 | SVSxRxKPSPRP |
| 93 | SVSVGMKPSPRP (14X) |
| 94 | TISRLEPPLKTA |
| 95 | TPHNTVS |
| 96 | VETRSAQPPSAG |
| 97 | RALSHHP |
| 98 | ASQSYFF |
| 99 | SPLPPMY |
| 100 | HYAQGDS |
| 101 | STQPSWH |
| 102 | STWPANQ |
| 103 | STMDPIL |
| 104 | TPAMMTR |
| 105 | RIVTPFI |
| 106 | TSSAKSM |
| 107 | NTTTHKL |
| 108 | EPRHSFS |
| 109 | MTKTAAE |
| 110 | SQNGLNS |
| 111 | TTQPAPAPPHIP |
| 112 | TSADNRWSPTTL (2X) |
| 113 | MPNVYMPGSPPH |
| 114 | TSPTLKLNPKYN |
| 115 | HNYQRHMLASVN |
| 116 | MPTNSNRVDPIP |
| 117 | HSVSNIRPMFPS |
| 118 | HSTSYQSLRWGA |
| 119 | SIASVESVRPPS |
| 120 | VRPLTLT |
| 121 | NLPYGSR |
| 122 | GOHAYTS |
| 123 | HPHLVQL |
| 124 | TMSTSRV |
| 125 | GTPFLSQ |
| 126 | YAPTPQF |
| 127 | GGAKLVP |
| 128 | DAPHHRS |
| 129 | RPYTNHA |
| 130 | FLSKNYN |
| 131 | APPAROT |
| 132 | DPQLSHL |
| 133 | LWPITTK |
| 134 | LLSSPRT |
| 135 | LAPAMPY |
| 136 | NTILMAT |
| 137 | IPxPTWRNEAPP |
| 138 | ALLPSFPTPPQP |
| 139 | SEQTNNLHHLST |
| 140 | AAxQPVPLPVGH |
| 141 | TNIGSYQMMYSR |
| 142 | LPSTSPLDRPRG |
| 143 | LNLHVIRDMPMR |
| 144 | LPYGHFLVQQPR |
| 145 | RLHQPAWTHSQH |
| 146 | SSMSAGYIHLDL |
| 147 | SLTPLTSASTPR |
| 148 | QFPLTTSVPTLM |
| 149 | KSTTESLNILFN |
| 150 | NKLPISVPFSAP |
| 151 | TDGYSRWMLPQS |
| 152 | HSQLNLPLFKQN |
| 153 | VAGQSNASPYGY |
| 154 | SPPVAQH |
| 155 | NHSTARW |
| 156 | QSFLHPT |
| 157 | SSMPPSL |
| 158 | SDILLST |

TABLE 6-continued

HepG2 Selected Peptides

| SEQ ID NO: | Display Peptide Amino Acid Sequence - HepG2 Selected Peptides |
|---|---|
| 159 | THVPPDW |
| 160 | SPQAHPQ |
| 161 | STFTHPR |
| 162 | SLPQRQQ |
| 163 | WTSAAPL |
| 164 | TTKIPPS |
| 165 | MGSGSSN |
| 166 | KTSAVLP |
| 167 | HIPPGSP |
| 168 | IPTLPSS (3X) |
| 169 | TAQLMFQ |
| 170 | NTHLQRE |
| 171 | LVGNYTP |
| 172 | HINFLHG |
| 173 | HHHHKPT |
| 174 | YKSAPPY |
| 175 | LPGQQFQ |
| 176 | YDNRHAL |
| 177 | HGPKFER |
| 178 | SLTPMGA |
| 179 | PKSTMYS |
| 180 | KPTWPLK |
| 181 | KPHPQHI |
| 182 | SASPLMH |
| 183 | TPTTLNQ |
| 184 | SPNKTQQ |
| 185 | DRQHLKH |
| 186 | NKPWPFN |
| 187 | HQTKSHH |
| 188 | SLMRLQPGYNTT |
| 190 | YMPHTRLDEPRK |
| 191 | S1PSHSRHSAKA |
| 192 | NTPAHANADFFD |
| 193 | IDTKQTFVSGFR |
| 194 | YPHYSLPGSSTL (2X) |
| 195 & 590 | HFPSTTLR*VTT |
| 196 | NYQPPRGWILAP |
| 197 & 554 | KLDNH*MLTHSP |
| 198 | SPPSFDPHRTTR |
| 199 | SHPWNAQRELSV |
| 200 | STQNASLLSLTG |
| 201 | NSAAADCYPQWLALRQPASGRPPPH* |
| 202 | NSAAADVYEQWLRGTGPRSGRPPPS* |
| 203 | NSAAADVYYQWLAYTGPPSGRPPPI* |
| 204 | NSQQQMFTRSGYRRRVLFLVVLPPL |
| 205 | NSAAADSYRQWLVAVGPNSGRPPPP* |
| 206 | NSAAADVYTQWLKNRGPISGRPPPL* |
| 207 | NSAAADTYSQWLAVEGPDSGRPPPA* |
| 208 & 555 | NSQQQILTLSG*VFMVLGLVVLPPL |
| 209 & 556 | NSAAADFY*QWLLSCGPKSGRPPPN* |
| 210 | NSAAADTYRQWLSPSGPWSGRPPPS* |
| 211 & 557 | NSQQQIITISG*GLGVLCLVVLPPL |
| 212 | NSAAADSYNQWLLYHGPSSGRPPP** |
| 213 | NSAAADTYSQWLRLLGPPSGRPPPR* |
| 214 | NSAAADPYSQWLPLKGPSGRPPPP* |
| 215 | NSAAADAYRQWLPTQGPPSGRPPPG* |
| 216 & 558 | NSQQQICTGSG*RLMVLPSGRPPPS* |
| 217 | NSAAADMYPQWLNFAGPMSGRPPPL* |
| 218 | NSAAADTYLQWLTNTGPFSGRPPPR* |
| 219 | NSAAADCYPQWLKLWGPCSGRPPPK* |
| 220 | NxAAADKYPQWLHTLxPNSWSVLPPQ* |
| 221 | NSAAADTYRQWLHVPGPPSGRPPPPL |
| 222 | NSQQQMRTCSGYRIMVLVLVVLPPF |
| 223 | NSAAADSYPQWLRSKGPPSGPSSPPV |
| 224 | NSAAADMYSQWLTNSGPFSGRPPPPL |
| 235 & 559 | NSAAADPYWQWLDS*GPASGRPPPHV |
| 236 | NSAAADPYTQWLNGAGPTSGRPPPP* |
| 237 | NSAAADKYNQWLSQSGPLSGRPPPN* |
| 238 | NSAAADRYLQWLPPSGPISGRPPPC* |
| 239 | NSAAADPYAQWLHPYGPRSGRPPPQ* |
| 240 | NSAAADFYPQWLNMNGPPSGRPPPI* |
| 241, 591 & 560 | NSAAADVYPQWLSC*WS*VWSSSPPL |
| 242 | NSAAADxYTQWLxNRGPTSGRPPPx* |
| 243 | NSAAADYYHQWLASRGPLSGRPPPHL |

TABLE 6-continued

HepG2 Selected Peptides

| SEQ ID NO: | Display Peptide Amino Acid Sequence - HepG2 Selected Peptides |
|---|---|
| 244 & 561 | NSQQQIGTVSG*WCMVLILVVLPPIN |
| 245 | NSAAADLYRQWLASLGPVSGRPPPR* |
| 246 | NSAAADDYPQWLLETGPCSGRPPPS* |
| 247 | NSAAADTYRQWLQPLGPPSGRPPPQ* |
| 248 | NSAAADLYRQWLLALGPESGRPPPL* |
| 249 & 562 | NSQQQISTRSG*CCRVLFLVVLPPGN |
| 250 | NSAAADAYAQWLLGEGPSSGRPPPN* |
| 251 | NSAAADSYPQWLLRLGPASGRPPPL* |
| 252 | NSAAADTYLQWLPQRGPPSGRPPPHV |
| 253 | NSAAADDYGQWLAQLGPLSGRPPPH* |
| 254 | NSAAADLYPQWLCLHGPRSGRPPPW* |
| 255 | NSAAADAYIQWLYVAGPASGRPPPR* |
| 256 | NSAAADSYTQWLPGHGPASGRPPPLV |
| 257 | NSAAADWYYQWLSASGPFVWSSLPPR* |
| 258 | NSAAADQYPQWLGLRGPTSGRPPPA* |
| 259 | NSAAADAYWQWLTIYGPVSGRPPPQ* |
| 260 | NSAAADVYMQLVIVYGPTSGRPPPI* |
| 261 | NSAAADPYFQWLkIPGPPSGRPPPR* |
| 262 | NSAAADTYLQWLDHTGPYSGRPPPY* |
| 263 | NSAAADAYGQWLPSTGPKSGRPPPLN |
| 264 | NSAAADCYTQWLASPGPKSGRPPPHV |
| 265 & 563 | NSQQQIRTVSG*WGLVLRLVVLPPLN |
| 266 | NSAAADFYVQWLFTSGPPSGRPPPD* |
| 267 | NSAAADLYYQWLATYGPASGRPPPM* |
| 268 | NSAAADHYGQWLSVPGPNSGRPPPI* |
| 269 | NSAAADVYIQWLFVTGPFSGRPPPH* |
| 270 | NSAAADLYAQWLARLGPPSGRPPPP* |
| 271 | NSAAADSYTQWLPGHGPASGRPPPLV |
| 272 | NSAAADWYYQWLSASGPFVWSSLPPR* |
| 273 | NSAAADWYAQWLLTRGPASGRPPPS* |
| 274 | NSAAADPYEQWLNVPOPPSGPSSPPRN |
| 275 | NSAAADAYWQWLTIYGPVSGRPPPQ* |
| 276 | NSAAADTYYQWLTQTGPLSGRPPPP* |
| 277 | NSAAADPYFQWLKIPGPPSGRPPPR* |
| 278 | NSAAADTYLxWxDHTGPYSGRPPPYx |
| 279 | NSAAADMYLQWLASSGPRSGRPPPY* |
| 280 | NSAAADQYSQWLVVGGPSSGRPSPPVT |
| 281 | NSAAADWYTSVVxxxGSxFWSSSPxV |
| 282 | NSAAADSYKQWLPALGPSSGRPPPS* |
| 283 | NSAAADAYRSVVRSYWSYFWSSSPPL |
| 284 | NSAAADYYRQWLAISGPLSGRPPPR* |
| 285 | NSAAADNYPQWLPPAGPTSGRPPPQ* |
| 286 | NSAAADRYHQWLRQKGPGSGRPPPA* (2X) |
| 287 & 564 | NSAAADLYSQWLF**GPLSGRPPPR* |
| 288 & 565 | NSAAADKY*QWLRAIGPGSGxPPPQ* |
| 289 & 566 | NSAAADHY*QWLESQGPLSGRPPPK* |
| 290 & 567 | NSAAAD*YTQWLWSRGPASGRxPxG* |
| 291 | NSAAADGYGQWLHKWGPSSGRPPPR* |
| 292 | NSAAADIYVQWLHELGPTSGLPxRK* |
| 293 & 568 | NSQQQIRTRSG*LLLVLLLVxPQxIN |
| 294 | NSAAADIYLQWLQMMGPLSGXPPPT* |
| 295 | NSAAADTYYQWLNPQGPFSGRPPPS* |
| 296 | NSAAADVYTQWLGKSGPLSGRPPPAY |
| 297 | NSAAADEYPQWLNTEGPHSGXPxxx* |
| 298 | NSAAADVYYQWLNSRGPPSGRPPPL* |
| 299 | NSAAADPYRQWLRTPGPRSGRPPPHL |
| 300 | NSAAADQYTQWLYTKGPFSGRPPPH |
| 301 | NSAAADQYRQWLWPTGPQSGLPxxG* (2X) |
| 302 | NSAAADVYRQWLRPVGPTSGRPPPR* |
| 303 | NSAAADQYLQWLLPPGPSSGRPPPK* |
| 304 | NSAAADPYPQWLMLRGPTSGRPSPHLN |
| 305 & 569 | NSAAAD*YLQWLSSTGPTSGRPPPT* |
| 306 & 570 | NSAAADPYWQWLLLTGP*SGLPPPE* |
| 307 | NSAATDRYAQWLAAYGPRSGRPPPP* |
| 308 | NSAAADSYKQWLGELGPPSGLxSPPL |
| 309 & 571 | NSAAADLYQQWLS*AGPLSGRPPPH* |
| 310 | NSAAADSYSQWLPGPGPNSGxPQxHV |
| 311 | NSAAADWYCQWLTRMGPPSGRPPPT* |
| 312 | NSAAADDYAQWLGVEGPRSGPPPT* |
| 313 | NSAAADQYLQWLRMTGPMSGRPPP** |
| 314 & 572 | NSQQQIITGSG*ILLVLSLVVLPPLN |
| 315 & 573 | NSQQQIFTSSG*IRMVLILVxxxxSN |
| 316 | NSAAADFYGQWLVKRGPNSGRPPPN* |
| 317 | NSAAADEYVQWLHPCGPDSGRPPPK* |
| 318 | NSAAADTYLQWLLQLGPHSGLxPGY* |

TABLE 6-continued

HepG2 Selected Peptides

| SEQ ID NO: | Display Peptide Amino Acid Sequence - HepG2 Selected Peptides |
|---|---|
| 319 & 574 | NSAAADPYWQWLLLTGP*SGRPPPE* |
| 320 | NSAATDRYAQWLAAYGPRSGRPPPP* |
| 321 | NSAAADSYKQWLGELGPPSGRSSPPL |
| 322 | NSAAADAYLQWLSQVGPHSGRPPPAV |
| 323 | NSAAADSYSQWLPGPGPNSGRPPPM* |
| 324 | NSAAADWYCQWLTRMGPPSGRPPPHL |
| 325 | NSAAADDYAQWLGVEGPRSGRPPPT* |
| 326 | NSAAADQYLQWLRMTGPMSGRPPP** |
| 327 & 575 | NSQQQIITGSG*ILLVLSLVVLPPLN |
| 328 & 576 | NSQQQIFTSSG*IRMVLILVVLPPSN |
| 329 | NSAAADFYGQWLVKRGPNSGRPPPN* |
| 330 | NSAAADEYVQWLHPCGPDSGRPPPK* |
| 331 | NSAAADQYQQWLKLLGPRSGRPPPV* |
| 332 | NSAAADIYKQWLHDDGPMSGRPPPR* |
| 333 | NSQQQIVTLSGYRRMVLVLVVLPPCN |
| 334 | NSAAADTYLQWLLQLGPHSGRPPPY* |
| 335 & 577 | NSAAAD*YLQWLSSTGPTSGRPPPT* |
| 336 & 578 | NSAAADPYWQWLLLTGP*SGRPPPE* |
| 337 | NSAATDRYAQWLAAYGPRSGRPPPP* |
| 338 | NSAAADSYKQWLGELGPPSGRSSPPL |
| 339 & 579 | NSAAADLYQQWLS*AGPLSGRPPPH* |
| 340 | NSAAADAYLQWLSQVGPHSGRPPPAV |
| 341 | NSAAADWYCQWLTRMGPPSGRPPPHL |
| 342 | NSAAADDYAQWLGVEGPRSGRPPPT* |
| 343 | NSAAADQYLQWLRMTGPMSGRPPP** |
| 344 & 580 | NSAAADPYWQWLLLTGP*SGRPPPE* |
| 345 | NSAATDRYAQWLAAYGPRSGRPPPP* |
| 346 | NSAAADQYLQWLRMTGPMSGRPPP** |
| 347 | NSAAADKYAQWLLAAGPTSGRPPPP* |
| 348 | NSAAADAYEQWLPRPGPDSGRPPPRV |
| 349 | NSAAADQYPQWLTMDGPPSGRPPPG* |
| 350 & 581 | NSAAADAYMQWLTLMGPTSGRPPPL*QACRRAPGISLQENS AAADVYEQWLQAPGPRSGRPPPV* |
| 351 & 582 | NSQQQILTRSG*SRLVLGLVVLPPIN |
| 352 | NSAAADIYIQWLTRTGPTSGRPPPF* |
| 353 | NSAAADAYDQWLPLPGPKSGRPPPA* |
| 354 | NSAAADPYPQWLSSRGPLVWSSSPHV |
| 355 | NSAAADPYLQWLVLRGPHSGRPPPW* |
| 356 | NSAAADDYTQxVSDSGSSVWSSSPPV |
| 357 | NSAAADRYLQWLSTIGPKSGRPPPM* |
| 358 | NSAAADIYPQWLLNSGPSSGRPPPT* |
| 359 | NSAAADSYSQWLPVLGPVSGRPPPR* |
| 360 | NSAAADPYRQWLVTMGPPSGRPPPP* |
| 361 | NSAAADSYHQWLSTYGPDSGRPPPQ* |
| 362 | NSQQQIWQWLHTQGPRSGRPPPN* |
| 363 & 583 | NSQQQIRTFSG*RIWVLGLVVLPPL* |
| 364 | NSAAADKYAQWLLAAGPTSGRPPPP* |
| 365 | NSAAADAYEQWLPRPGPDSGRPPPRV |
| 366 | NSAAADKYAQWLLAAGPTSGRPPPP* |
| 367 | NSAAADAYEQWLPRPGPDSGRPPPRV |
| 368, 584 & 585 | NSAAADPYIQWLHKHGPISGRxExPSRTLLH*PLPVPICCCRIR QQQIITLSG*LLLVLLLVVLPPRN |

TABLE 7

HUVEC Selected Peptides

| SEQ ID NO: | Display Peptide Amino Acid Sequence - HUVEC Selected Peptides |
|---|---|
| 369 | GKHSINL (9X) |
| 370 | GNPLWGT (15X) |
| 371 | SARQQAF |
| 372 | KPYTYLT (9X) |
| 373 | SPQTHQA |
| 374 | PLFSTRM |
| 375 | HNLQPGH |
| 376 | WSVFPYS |
| 377 | RPTAQYD |
| 378 | GLSHTAP |
| 380 | TTLHHTN |
| 381 | QHPPWRV |
| 383 | HHSLTVT (2X) |
| 384 | AATDLRT |
| 385 | SPLPQSQ (3X) |
| 386 | SPNKPLH |
| 387 | GMPRPAS (2X) |
| 388 | SPSSATA (2X) |
| 389 | GPFSTRD |

TABLE 7-continued

HUVEC Selected Peptides

| SEQ ID NO: | Display Peptide Amino Acid Sequence - HUVEC Selected Peptides |
|---|---|
| 592 & 593 | WPT*DSF |
| 391 | VRPHQEF |
| 392 | TPPTMDH |
| 393 | SIERSAN |
| 394 | FQGDKTF |
| 395 | STTPLGH |
| 396 | LPDNQHS |
| 397 | QTK1TMS |
| 398 | TVNKPVL |
| 399 | RLQDTAQ |
| 400 | VHTQGKA |
| 401 | HPTQHKN |
| 402 | QAKWHKS |
| 403 | RLPAPPH |
| 404 | YPQERTP (3X) |
| 405 | MPSREPI (3X) |
| 406 | FSNHSPW |
| 407 | NATLTRL |
| 408 | APWMRPD (2X) |
| 409 | HPHHRWA |
| 410 | IVATQIY |
| 411 | TNSNAHH |
| 412 | SVALSSR |
| 413 | SILPRPF |
| 414 | SSNSSHH |
| 415 | SHVNMKN |
| 416 | LDLRFP |
| 417 | PPNKALH (3X) |
| 418 | SPWGLAQ |
| 419 | SVMKQKM |
| 420 | QSVWQTN |
| 421 | QPALSPR |
| 422 | LDPTGRH |
| 423 | xxPxSxx |
| 424 | SQHWAPSGSPWK (18X) |
| 425 & 390 | LPIPER*ASPLT |
| 426 | FDNFKTISSSSH |
| 427 | STTLNNTTWRLY |
| 428 | QEALSRSPYDAR |
| 594 & 429 | SVP*TWNIPDVD (2X) |
| 430 | GLEFKSPLPASS |
| 431 | VSSQYSVTPARV |
| 432 | DIHARSA |
| 433 | TSKGPTQ |
| 434 | TNTSVKV |
| 435 | VPSTLPR |
| 436 | SNSTLHK |
| 437 | QSVWQTN |
| 438 | QFSTNPR |
| 439 | HYPSITH |
| 440 | DPLLPPM |
| 441 | GAIPHFR |
| 442 | SHVNMKN |
| 443 | QPTKVPG |
| 445 | FNTLRTA |
| 446 | LDLRFPQ |
| 447 | NSQQQIITRSGYRMRVLRSGRPPPR* (3X) |
| 448 | NSAAADSYNQWLHTTGPSSGxPxxPL |
| 449 | NSAAADNYKQWLNYIGPASGRPxxQ* |
| 450 & 587 | NSQQQIRTLSG*RLRVLFLVVLPPSN |
| 451 | NSAAADFYQWLPAHOPTSGRPPPP |
| 452 | NSAAADRYEQWLRTCGPLSGRPPPS* |
| 453 | NSAAADPYPQWLRRRGPRSGRPPPR* |
| 454 | NSAAADPYIQWLRHHGPLSGxxxxY* |
| 455 | NSAAADRYHQWLPRRGPASGxPPPR* |
| 456 | NSAAADPYNQWLLMHGPRSGRPSPPRN |
| 457 & 382 | NSQQQIRTFSG*CRLVLGLVVLPPSN |
| 458 & 444 | NSQQQMRTGSG*LCRVLVLVVLPPIN |
| 459 | NSAAADPYLQWLHRVGPxSGRPPPx* |
| 460 | NSAAADPYRQWLRRPGPRSGRPPPR* |
| 461 | NSAAADLYLQWLSLYGPDSGRPPPT* |
| 462 | NSAAADTYAQWLRAWGPSSGRPPPF* |
| 463 & 379 | NSQQQIVTVSG*LLLVLVLVVLPxCN |
| 464 | NSAAAxSYSQWLRRGGPASGRPPPR* |
| 465 | NSAAADPYFQWLLPLGPJSGRXPRX |
| 466 | NSAAADKYDQWLCYAGPRSGLxxxW* |
| 467 | NSAAADLYFQWLIKVGPFSGLPQxGL |
| 468 | NSQQQIRTRRLKRPGPSSGRXPQx* |
| 469 | NSAAADRYHQWLRRRGPRSGRPPPR* |
| 470 & 225 | NSQQQHTSSG*SVRVLLLVVLPPR* |
| 471 | NSAAADPYKQWLKRRGPRSGRPPPP* |
| 472 & 226 | NSQQQMGTVSG*RSLVLFLVVLPPV |
| 473 | NSAAADHYLQWLNNLGPESGRPPPK* |
| 474 | NSAAADWYSQWLESKGPASGRPPPN* |
| 475 | NSAAADDYPQWLTRTGPSSGRPPPT* |
| 476 | NSAAADFYTQWLSGPGPTSGRPPPS* |
| 477 | NSAAADKYDQWLCYAGPRSGRPPPW* |
| 478 | NSAAADLYFQWLIKVGPFSGRPPPV* |
| 479 | NSQQQIRTRRFKEAGSFVWSSSPPL |
| 480 | NSAAADRYHQWLRRRGPRSGRPPPR* |
| 481 | NSAAADRYWQWLKPTGPRSGRPPPR* |
| 482 & 227 | NSQQQIITSSG*SVRVLLLVVPPPR* |
| 483 | NSAAADGYSQWLSTQGPWSGRPPPD* |
| 484 | NSAAADPYKQWLKRRGPRSGRPPPR* |
| 485 & 228 | NSQQQMGTVSG*RSLVLFLVVLPPV |
| 486 | NSAAADHYLQWLNNLGPESORPPPK* |
| 487 | NSAAADWYSQWLESKGPASGRPPPD* |
| 488 | NSAAADDYPQWLTRTGPSSGRPPPT* |
| 489 | NSAAADPYAQWLRATGPRSGxPPPR* |
| 490, 595 & 229 | NSAAADGLRSVVT*EWSWXxSxPPL |
| 491 | NSAAADFYTQWLSGPGPTSGRPPPS* |
| 492 | NSAAADRYAQWLLTVG PISGRPSPPV |
| 493 | NSAAADPYRQWLPARGPRSGRPPPR~ |
| 494 | NSAAADYYHQWLKAAGPSSGRPPPR* |
| 495 | NSAAADKYDQWLCYAGPRSGRPPPW* |
| 496 | NSAAADLYFQWLIKVGPFSGRPPPV* |
| 497 | NSQQQIRTRRFKEAGSFVWSSSPPL |
| 498 | NSAAADRYHQWLRRRGPRSGRPPPR* |
| 499 | NSGAADRYWQWLKPTGPRSGRPPPR* |
| 500 & 230 | NSQQQIITSSG*SVRVLLLVVPPPR* |
| 501 | NSAAADGYSQWLSTQGPWSGRPPPD* |
| 502 | NSAAADPYKQWLKRRGPRSGRPPPR* |
| 503 & 231 | NSQQQMGTVSG*RSLVLFLVVLPPV |
| 504 | NSAAADHYLQWLNNLGPESGRPPPK* |
| 505 | NSAAADWYSQWLESKGPASGRPPPD* |
| 506 | NSAAADDYPQWLTRTGPSSGRPPPT* |
| 507 | NSAAADPYAQWLRATGPRSGxPPPR* |
| 508, 595 & 232 | NSAAADGLRSVVT*EWS*VxxSxPPL |
| 509 | NSAAADFYTQWLSGPGPTSGRPPPS* |
| 510 | NSAAADRYAQWLLTVGPISGRPSPPV |
| 511 | NSAAADPYRQWLPARGPRSGRPPPR* |
| 512 | NSAAADYYHQWLKAAGPSSGRPPPR* |
| 513 | NSAAADRYHQWLPRRGPASxRPPPR* |
| 514 | NSAAADWYSQWLLRTGPRSGRPPPPV |
| 515 | NSAAADQYAQWLSRLGPLSGRPPPT* |
| 516 | NSAAADRYIQWLATSGPLSGRPPPR* |
| 517 | NSAAADQYPQWLPLAGPHSGRPPPK* |
| 518 & 233 | NSQQQILTVSG*LCLVLSLVVLLPCN |
| 519 | NSAAADRYHQWLPRRGPASGRPPPR* |
| 520 | NSAAADPYSQWLQTPGPTSGRPPPQV |
| 521 | NSAAADSYPQWLSTVGPRSGRPPPV* |
| 522 | NSAAADLYWQWLSMPGPLSGRPPPI* |
| 523 & 234 | NSQQQIFTLSG*RRRVLLLVVLPPRN |
| 524 | NSQQQIRTRSGYRRMGRPSGRPPPR* |
| 525 | NSAAADLYMQWLAVMGPDSG RPPPL* |
| 526 | NSAAADGYRQWLPPAGPKSGRPPPY* QACRRAPGISLQENSAAADRYYQWLL VVGPVSGRPPPI* |
| 527 | NSAAADPYHQWLRTFGPYSGRPPPR* |
| 528 | NSAAADSYRQWLNKTGPISGRPPPL* |
| 529 | NSGAADRYWQWLKPTGPRSGRPPPR* |

In general, the display peptides isolated after panning against HepG2 and/or HUVEC cell types with the Trp cage library showed a strong propensity toward the selection of Arg (R) residues at the randomized positions especially in sequences derived from panning against HUVEC. This propensity was not as strong in sequences from the M13 libraries.

The third cell types the Trp cage libraries were panned against was the human bronchial epithelial cell line 16HBE140-. After three rounds of panning the amino acid sequences displayed by 18 randomly selected clones were deduced from the nucleotide sequence of the selected clones. As shown in Table 8, there were four full length Trp cage sequences including five instances (identified by '5x' after the amino acid sequence of the isolated Trp cage peptide) of the same sequence represented by clone number 624-55-21. There were also five instances of the truncated peptide represented by clone number 624-55-26.

TABLE 8

Peptides Obtained from Panning Against 16HBE140-Cells

| | Clone Number | Amino Acid Sequence of Peptide (variable positions underlined) | SEQ ID NO |
|---|---|---|---|
| Full-length Trp Cage | 624-55-20 | DRYPQWLNGMGPSSGRPPPN* | 541 |
| | 624-55-21 | DAYPQWLFTPGPTSGRPPPL* (5x) | 542 |
| | 624-55-29 | DPYAQWLQSMGPHSGRPPPR* | 543 |
| | 624-55-36 | DMYAQWLDNMGPHSGRPPPY* | 544 |
| Mutant Trp Cage | 624-55-24 | DAYSQWLLQTGPYSGRPSPRV | 545 |
| | 624-55-32 | DTYIQWLKINGPRLVVLPPRN | 546 |
| | 624-55-33 | DAYGQWLRTSGPLSGRSLPPR | 547 |
| | 624-55-37 | DWYQQWLPPGGPGSGRPPPHL | 548 |
| Truncated Trp Cage | 624-55-22 | DLYLQWLD*PGPSSGRPPPLL | 549 & 586 |
| | 624-55-26 | D*YTQWLYLQGPNSGRPPPY* (5x) | 596 & 550 |

Binding of the displayed peptides to 16HBE140-cells was evaluated by phage ELISA using unfixed cells. Binding of phage T7Select® 10-3b displaying Trp cage TC5b (Trp cage) was compared to binding of three phage clones selected from the nave Trp cage library after 3 rounds of panning against the human bronchial epithelial cell line 16HBE14o-. Results represent the average of triplicate wells.

As shown in Table 9, binding to 16HBE140-cells was low for the negative control phage displaying the TC5b version of the Trp cage NLYIQWLKDGGPSSGRPPPS (SEQ ID NO: 530), and for two of the phage clones selected at random after panning against the 16HBE140-cells. Phage clone 624-55-29 displaying the peptide AAADPYAQWLQSMGPHSGRPPP R (SEQ ID NO: 551) (amino acids in the variable positions are underlined) demonstrated binding to 16HBE140-cells. This result indicated that the Trp cage library can be used to select peptides with cell binding capability.

TABLE 9

Binding to 16HBE140- Cells

| Phage clones ($10^{10}$ pfu/ml) | OD 450 nm |
|---|---|
| Trp cage | 0.22 |
| 624-55-20 | 0.22 |
| 624-55-21 | 0.15 |
| 624-55-29 | 0.39 |

Example 11

The M13 Phage Display Peptide Having the Amino Acid Sequence NLQEFLF Binds Preferentially to Liver Cells The present example demonstrates that the exemplary peptide (NLQEFLF; SEQ ID NO: 61) of the present invention isolated from multiple rounds of panning with the M13 phage display library binds preferentially to liver cells (HepG2 cells). Representative display peptides isolated from panning against either HepG2 or HUVEC cells with the Trp cage and M13 libraries were tested for cell-specific binding. The peptide having the amino acids sequence SIGYLPL (SEQ ID NO: 532) and the peptide having the amino acid sequence LTAELTP (SEQ ID NO: 533) served as positive HepG2 binding controls. The 7-mer display peptide represented by the amino acid sequence HPQ served as a negative binding control.

Cell-based ELISA of 12 clones isolated from panning against HepG2 cells with the MB PHD-7 phage display library resulted in the discovery of the HepG2 specific binding display peptide having the amino acid sequence NLQEFLP (SEQ ID NO: 61). Based on the ELISA data, this peptide did not bind to HUVEC cells. The remaining 11 clones did not show any preferential binding to HepG2 cells. Further, fluorescence microscopy with FITC-labeled phage indicated that PhD-7 phage displaying the NLQEFLF (SEQ ID NO: 61) amino acid sequence bound to methanol-fixed HepG2 cells. Staining by the positive controls was less intense than NLQEFLF (SEQ ID NO: 61). The negative controls included phage with no displayed peptide (KE) and phage displaying an unrelated 7-mer peptide (HPQ). These results are consistent with the ELISA results.

These data show that panning with a phage display library against a cell-specific target, for example HepG2 cells, results in the isolation of a peptide that preferentially binds HepG2 (liver) cells. This peptide is an ideal candidate for liver cell based delivery of pharmaceutical agents. Further, in general, these data indicate that phage display libraries are useful for isolating target specific peptides, example targets being a cell type or tissue type, cell surface protein and/or intracellular targets for use in the delivery of pharmaceutical agents to specific targets.

What is claimed is:

1. A method for delivering a drug, compound or biologically active agent to a liver tissue of a subject, the method comprising: complexing or conjugating the drug, compound or biologically active agent with a polypeptide comprising the amino acid sequence of SEQ ID NO:61 thereby forming a complex or conjugate, and administering the complex or conjugate to the liver tissue of the subject.

2. The method of claim 1, wherein the drug, compound or biologically active agent is an siRNA molecule.

3. The method of claim 1, wherein the polypeptide binds liver tissue.

4. The method of claim 1, wherein the polypeptide binds a human hepatocyte.

5. The method of claim 1, wherein the complex or conjugate is administered intravenously.

6. The method of claim 1, wherein the complex or conjugate is administered by injection.

7. A method for delivering a biologically active agent to a liver cell, the method comprising: complexing or conjugating the biologically active agent with a polypeptide comprising the amino acid sequence of SEQ ID NO:61, thereby forming a complex or conjugate, and administering the complex or conjugate to the liver cell.

8. The method of claim 7, wherein the biologically active agent is an siRNA molecule.

9. The method of claim 7, wherein the polypeptide binds the liver cell.

10. The method of claim 7, wherein the polypeptide binds a hepatocyte.

11. The method of claim 7, wherein the complex or conjugate is administered intravenously or by injection.

12. A method for preparing an RNAi agent for targeting to a liver tissue, the method comprising:

providing an RNAi agent; and contacting the RNAi agent with a polypeptide comprising the amino acid sequence of SEQ ID NO:61, thereby forming a complex or conjugate of the RNAi agent.

13. The method of claim 12, wherein the RNAi agent is an siRNA molecule.

14. The method of claim 12, wherein the polypeptide binds the liver tissue.

15. The method of claim 12, wherein the polypeptide binds a hepatocyte.

* * * * *

SEQUENCE LISTING

<160> NUMBER OF SEQ ID NOS: 596

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 103
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MOD_RES
<222> LOCATION: (30)..(31)
<223> OTHER INFORMATION: a, c, g, t, unknown or other
<220> FEATURE:
<221> NAME/KEY: MOD_RES
<222> LOCATION: (36)..(37)
<223> OTHER INFORMATION: a, c, g, t, unknown or other
<220> FEATURE:
<221> NAME/KEY: MOD_RES
<222> LOCATION: (48)..(49)
<223> OTHER INFORMATION: a, c, g, t, unknown or other
<220> FEATURE:
<221> NAME/KEY: MOD_RES
<222> LOCATION: (51)..(52)
<223> OTHER INFORMATION: a, c, g, t, unknown or other
<220> FEATURE:
<221> NAME/KEY: MOD_RES
<222> LOCATION: (54)..(55)
<223> OTHER INFORMATION: a, c, g, t, unknown or other
<220> FEATURE:
<221> NAME/KEY: MOD_RES
<222> LOCATION: (63)..(64)
<223> OTHER INFORMATION: a, c, g, t, unknown or other
<220> FEATURE:
<221> NAME/KEY: MOD_RES
<222> LOCATION: (84)..(85)
<223> OTHER INFORMATION: a, c, g, t, unknown or other

<400> SEQUENCE: 2
cacatgcccc gaattcggca gcagcagatn nktacnnkca gtggttannk nnknnkggtc      60
ctnnktctgg tcgtcctccc cccnnktaac aagcttgaac atg                      103

<210> SEQ ID NO 3
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MOD_RES
<222> LOCATION: (13)..(14)
<223> OTHER INFORMATION: a, c, g, t, unknown or other

```
<220> FEATURE:
<221> NAME/KEY: MOD_RES
<222> LOCATION: (19)..(20)
<223> OTHER INFORMATION: a, c, g, t, unknown or other
<220> FEATURE:
<221> NAME/KEY: MOD_RES
<222> LOCATION: (31)..(32)
<223> OTHER INFORMATION: a, c, g, t, unknown or other
<220> FEATURE:
<221> NAME/KEY: MOD_RES
<222> LOCATION: (34)..(35)
<223> OTHER INFORMATION: a, c, g, t, unknown or other
<220> FEATURE:
<221> NAME/KEY: MOD_RES
<222> LOCATION: (37)..(38)
<223> OTHER INFORMATION: a, c, g, t, unknown or other
<220> FEATURE:
<221> NAME/KEY: MOD_RES
<222> LOCATION: (46)..(47)
<223> OTHER INFORMATION: a, c, g, t, unknown or other
<220> FEATURE:
<221> NAME/KEY: MOD_RES
<222> LOCATION: (67)..(68)
<223> OTHER INFORMATION: a, c, g, t, unknown or other

<400> SEQUENCE: 3
gcagcagcag atnnktacnn kcagtggtta nnknnknnkg gtcctnnktc tggtcgtcct       60 cccccnnk                                                               69

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (11)..(13)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid
<220> FEATURE:
<221> NAME/KEY: MOD_RES
<222> LOCATION: (23)..(23)
<223> OTHER INFORMATION: Variable amino acid

<400> SEQUENCE: 4

Ala Ala Ala Asp Xaa Tyr Xaa Gln Trp Leu Xaa Xaa Xaa Gly Pro Xaa
1               5                   10                  15

Ser Gly Arg Pro Pro Pro Xaa
            20

<210> SEQ ID NO 5
<211> LENGTH: 73
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asn Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
tgcgtgactt ggctctggag                                            20

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
aatttattta tcgaatggct caaaaatggt ggtccttcca gtggtgctcc tcccccttcc    60
taa                                                                 63

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
agctttagga aggggagga gcaccactgg aaggaccacc attttgagc cattcgataa     60 ata                                                                63

<210> SEQ ID NO 9
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
aattcggcag ctgcgaattt gtatattcag tggcttaagg atggtggtcc ttcgtcgggg    60
cggcctccgc caagttaaa                                                79

<210> SEQ ID NO 10
<211> LENGTH: 78
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 10
agcttttaac ttggcggagg ccgccccgac gaaggaccac catccttaag ccactgaata    60
tacaaattcg cagctgcc                                                  78

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cacatgcccc gaattcggca                                                20

<210> SEQ ID NO 12
<211> LENGTH: 103
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MOD_RES
<222> LOCATION: (19)..(20)
<223> OTHER INFORMATION: a, c, g, t, unknown or other
<220> FEATURE:
<221> NAME/KEY: MOD_RES
<222> LOCATION: (40)..(41)
<223> OTHER INFORMATION: a, c, g, t, unknown or other
<220> FEATURE:
<221> NAME/KEY: MOD_RES
<222> LOCATION: (49)..(50)
<223> OTHER INFORMATION: a, c, g, t, unknown or other
<220> FEATURE:
<221> NAME/KEY: MOD_RES
<222> LOCATION: (52)..(53)
<223> OTHER INFORMATION: a, c, g, t, unknown or other
<220> FEATURE:
<221> NAME/KEY: MOD_RES
<222> LOCATION: (55)..(56)
<223> OTHER INFORMATION: a, c, g, t, unknown or other
<220> FEATURE:
<221> NAME/KEY: MOD_RES
<222> LOCATION: (67)..(68)
<223> OTHER INFORMATION: a, c, g, t, unknown or other
<220> FEATURE:
<221> NAME/KEY: MOD_RES
<222> LOCATION: (73)..(74)
<223> OTHER INFORMATION: a, c, g, t, unknown or other

<400> SEQUENCE: 12
catgttcaag cttgttamnn gggggagga cgaccagamn naggaccmnn mnnmnntaac     60
cactgmnngt amnnatctgc tgctgccgaa ttcgggcat gtg                       103

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Asn Leu Tyr Ile Gln Trp Leu Lys Asp Gly Gly Pro Ser Ser Gly
1               5                   10                  15

```
Arg Pro Pro Pro Ser
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Leu Phe Ile Glu Trp Leu Lys Asn Gly Gly Pro Ser Ser Gly Ala
1               5                   10                  15

Pro Pro Pro Ser
            20

<210> SEQ ID NO 15
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aattgattta tcgaacggct caaaaatggt ggtccttcca gtggtgctcc tccccttcc      60 taa                                                                  63

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Leu Phe Ile Glu
1               5

<210> SEQ ID NO 17
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aatttattta tcgaatagct caaaagggt ggtccttcca gtggtgctcc tccccttcc       60 taa                                                                  63

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Leu Phe Ile Glu Ser
1               5
```

```
<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MOD_RES
<222> LOCATION: (21)..(21)
<223> OTHER INFORMATION: a, c, g, t, unknown or other
<220> FEATURE:
<221> NAME/KEY: MOD_RES
<222> LOCATION: (23)..(23)
<223> OTHER INFORMATION: a, c, g, t, unknown or other

<400> SEQUENCE: 19
aatttattta tcgaatcgct ntntaaaggg tggtccttcc                            40

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Leu Phe Ile Glu Gly Ser Lys Met Val Val Leu Pro Arg Gly Ala
1               5                   10                  15

Pro Pro Pro Ser
            20

<210> SEQ ID NO 21
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aatttattta tcgaaggctc aaaaatggtg gtccttccac gtggtgctcc tcccccttcc     60
taa                                                                   63

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Leu Phe Ile Glu Trp Leu Lys Asn Gly Gly Leu Pro Val Val Leu
1               5                   10                  15

Leu Pro Leu Pro
            20

<210> SEQ ID NO 23
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
```

-continued

```
aatttattta tcgaatggct caaaaatggt ggtcttccag tggtgctcct ccccttcct       60 aa                                                                     62
```

<210> SEQ ID NO 24
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MOD_RES
<222> LOCATION: (19)..(20)
<223> OTHER INFORMATION: a, c, g, t, unknown or other
<220> FEATURE:
<221> NAME/KEY: MOD_RES
<222> LOCATION: (25)..(26)
<223> OTHER INFORMATION: a, c, g, t, unknown or other
<220> FEATURE:
<221> NAME/KEY: MOD_RES
<222> LOCATION: (37)..(38)
<223> OTHER INFORMATION: a, c, g, t, unknown or other
<220> FEATURE:
<221> NAME/KEY: MOD_RES
<222> LOCATION: (40)..(41)
<223> OTHER INFORMATION: a, c, g, t, unknown or other
<220> FEATURE:
<221> NAME/KEY: MOD_RES
<222> LOCATION: (43)..(44)
<223> OTHER INFORMATION: a, c, g, t, unknown or other
<220> FEATURE:
<221> NAME/KEY: MOD_RES
<222> LOCATION: (52)..(53)
<223> OTHER INFORMATION: a, c, g, t, unknown or other

<400> SEQUENCE: 24

```
aattcggcag cagcagatnn ktacnnkcag tggttannkn nknnkggtcc tnnktctggt       60
cgtcctcccc ccccctaa                                                    78
```

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Asn Ser Gln Gln Gln Ile Arg Thr Cys Ser Gly
1               5                   10
```

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
aattcgcagc agcagatccg tacttgcagt ggttaa                                36
```

<210> SEQ ID NO 27
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Ser Ala Ala Ala Asp Arg Tyr His Gln Trp Leu Arg Leu Ser Gly
1               5                   10                  15

Pro Pro Ser Gly Arg Pro Ser Pro Pro Val Thr Ser Leu Arg Pro His
            20                  25                  30

Ser Ser Asn
        35

<210> SEQ ID NO 28
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aattcggcag cagcagatag gtaccatcag tggttaaggc tttctggtcc tccgtctggt      60
cgtccctccc ccccggtaac aagcttgcgg ccgcactcga gtaactag                  108

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Leu His Pro Gln His Ala
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Arg His Pro Gln Trp Ala
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Pro Pro Leu Ser Gly Thr
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Asn Tyr Leu Thr Ser Pro Leu
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Pro Leu Arg His
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala His Thr Leu Pro Pro Trp
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Ala Val Pro Leu Met Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ser Thr Pro Tyr Thr Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Pro Pro Met Ala Val Pro
1               5

<210> SEQ ID NO 38
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 38

Asn Thr Leu Pro Ser Gln Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Pro Asn Ile Pro Tyr Ser
1               5

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Ala Glu Ile Arg Pro Ala His Val Met Phe
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Pro His Pro Gly Arg Glu Val Ile Gln His
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Asp Gly Ser Met Ala Tyr Lys Arg Ser Thr Leu
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Pro Tyr Arg Thr Leu Thr Pro Ala Gly Ile Asn
1               5                   10
```

```
<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser His Ser Lys Phe Asp Thr His Arg Pro Asp Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Pro Leu Asn Val Asn Thr His Gln Ala Thr Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala His Pro Ser Ser Gln Met Ser Ser Pro Ser Pro
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Pro Thr Thr Lys Gln Met
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Val Thr Thr Leu Lys Ala
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 49

Asn Ser Leu Asn Tyr His Leu
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Pro Arg Gln Ser Leu His
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Thr Phe Pro Arg Gln Ala
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Asn Gln His Pro Met Leu
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Tyr Pro Met Thr Gly Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser His Pro Leu Ala Thr
1               5

<210> SEQ ID NO 55
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 55

Asn Ser Ser Ser Ser Ser Gln
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Thr Met Asp Pro Ile Leu
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Tyr Lys Pro Ser Pro Leu
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Thr Val Leu Thr Pro Lys
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Ala Ile Tyr Pro Arg His
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Thr Gly Ser Ser Thr Ile
1               5
```

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Leu Gln Glu Phe Leu Phe
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Pro Ala Thr Ser Pro Phe
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Tyr Ser Thr Ala Leu Thr
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Ser Pro Asn Lys Gln Leu
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Ser Lys Asn Ser Pro Ala
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 66

Ser Ser Lys Glu Pro Lys Ala
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Thr Met His Pro His Met
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Pro His Tyr Arg Ala Tyr
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Thr Arg Met His Pro Asp
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Pro Thr Pro Phe His His
1               5

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Ala Pro Asn Leu Asn Ala Leu Ser Ala Ala Ser
1               5                   10

<210> SEQ ID NO 72
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Leu Ala Asp Thr Thr His His Arg Pro Trp Thr
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Variable amino acid

<400> SEQUENCE: 73

Val Leu Pro Xaa Lys Pro Met Arg Gln Pro Val Ala
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Val Met Thr Tyr Pro Tyr Ser Arg Ala Tyr His
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala His His Asn Ser Trp Lys Ala Lys His His Ser
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

His Tyr Leu Ser Pro Ala Pro Ala Ser Leu Arg Pro
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 77

Ser Ser Ala Gln Asn Tyr Ala Trp Leu Ala Pro Arg
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala His His Tyr Thr Ala Thr Pro Thr Ile Gln Ser
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asn Val Ser Ser Ala Trp Leu
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Gln Thr Met Ala Arg Leu
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Lys His Asn Asp Ala Ala
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Thr Asn Ser Gln Lys Met
1               5

<210> SEQ ID NO 83
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Asn Pro Pro Met Thr Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Asn Ile Ile Met Ser Pro
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

His Ala Arg Leu Pro Ser Ala
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid

<400> SEQUENCE: 86

Ala Xaa Tyr Met Xaa Xaa Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Thr Met Asp Pro Ile Leu
1               5

<210> SEQ ID NO 88
<211> LENGTH: 7
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 88

Glu Pro Leu Gln Leu Lys Met
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

His Ala Ile Tyr Pro Arg His
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Gly Glu Thr Arg Ala Pro Leu
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Ala His His Asn Ser Trp Lys Ala Lys His His Ser
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid

<400> SEQUENCE: 92

Ser Val Ser Xaa Arg Xaa Lys Pro Ser Pro Arg Pro
1               5                   10

<210> SEQ ID NO 93
<211> LENGTH: 12
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 93

Ser Val Ser Val Gly Met Lys Pro Ser Pro Arg Pro
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Ile Ser Arg Leu Glu Pro Pro Leu Lys Thr Ala
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Thr Pro His Asn Thr Val Ser
1               5

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Val Glu Thr Arg Ser Ala Gln Pro Pro Ser Ala Gly
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ala Leu Ser His His Pro
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Ser Gln Ser Tyr Phe Phe
1               5
```

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Pro Leu Pro Pro Met Tyr
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

His Tyr Ala Gln Gly Asp Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Thr Gln Pro Ser Trp His
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Thr Trp Pro Ala Asn Gln
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Thr Met Asp Pro Ile Leu
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 104

Thr Pro Ala Met Met Thr Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ile Val Thr Pro Phe Ile
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Ser Ser Ala Lys Ser Met
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asn Thr Thr Thr His Lys Leu
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Pro Arg His Ser Phe Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Met Thr Lys Thr Ala Ala Glu
1               5

<210> SEQ ID NO 110
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 110

Ser Gln Asn Gly Leu Asn Ser
1               5

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Thr Gln Pro Ala Pro Ala Pro Pro His Ile Pro
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Ser Ala Asp Asn Arg Trp Ser Pro Thr Thr Leu
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Met Pro Asn Val Tyr Met Pro Gly Ser Pro Pro His
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Ser Pro Thr Leu Lys Leu Asn Pro Lys Tyr Asn
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

His Asn Tyr Gln Arg His Met Leu Ala Ser Val Asn
1               5                   10
```

```
<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Met Pro Thr Asn Ser Asn Arg Val Asp Pro Ile Pro
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

His Ser Val Ser Asn Ile Arg Pro Met Phe Pro Ser
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

His Ser Thr Ser Tyr Gln Ser Leu Arg Trp Gly Ala
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Ile Ala Ser Val Glu Ser Val Arg Pro Pro Ser
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Val Arg Pro Leu Thr Leu Thr
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 121

Asn Leu Pro Tyr Gly Ser Arg
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Gly His Ala Tyr Thr Ser
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

His Pro His Leu Val Gln Leu
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Met Ser Thr Ser Arg Val
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Thr Pro Phe Leu Ser Gln
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Tyr Ala Pro Thr Pro Gln Phe
1               5

<210> SEQ ID NO 127
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Gly Ala Lys Leu Val Pro
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asp Ala Pro His His Arg Ser
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Arg Pro Tyr Thr Asn His Ala
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Phe Leu Ser Lys Asn Tyr Asn
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Pro Pro Ala Arg Gly Thr
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Pro Gln Leu Ser His Leu
```

-continued

```
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Leu Trp Pro Ile Thr Thr Lys
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Leu Leu Ser Ser Pro Arg Thr
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Ala Pro Ala Met Pro Tyr
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asn Thr Ile Leu Met Ala Thr
1               5

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid

<400> SEQUENCE: 137

Ile Pro Xaa Pro Thr Trp Arg Asn Glu Ala Pro Pro
1               5                   10

<210> SEQ ID NO 138
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Leu Leu Pro Ser Phe Pro Thr Pro Pro Gln Pro
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Glu Gln Thr Asn Asn Leu His His Leu Ser Thr
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid

<400> SEQUENCE: 140

Ala Ala Xaa Gln Pro Val Pro Leu Pro Val Gly His
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Asn Ile Gly Ser Tyr Gln Met Met Tyr Ser Arg
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Pro Ser Thr Ser Pro Leu Asp Arg Pro Arg Gly
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 143

Leu Asn Leu His Val Ile Arg Asp Met Pro Met Arg
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Leu Pro Tyr Gly His Phe Leu Val Gln Gln Pro Arg
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Arg Leu His Gln Pro Ala Trp Thr His Ser Gln His
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Ser Met Ser Ala Gly Tyr Ile His Leu Asp Leu
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Leu Thr Pro Leu Thr Ser Ala Ser Thr Pro Arg
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Phe Pro Leu Thr Thr Ser Val Pro Thr Leu Met
1               5                   10

<210> SEQ ID NO 149
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Lys Ser Thr Thr Glu Ser Leu Asn Ile Leu Phe Asn
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Lys Leu Pro Ile Ser Val Pro Phe Ser Ala Pro
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Thr Asp Gly Tyr Ser Arg Trp Met Leu Pro Gln Ser
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

His Ser Gln Leu Asn Leu Pro Leu Phe Lys Gln Asn
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Val Ala Gly Gln Ser Asn Ala Ser Pro Tyr Gly Tyr
1               5                   10

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Pro Pro Val Ala Gln His
```

```
<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asn His Ser Thr Ala Arg Trp
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Ser Phe Leu His Pro Thr
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Ser Met Pro Pro Ser Leu
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Asp Ile Leu Leu Ser Thr
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr His Val Pro Pro Asp Trp
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 160

Ser Pro Gln Ala His Pro Gln
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Thr Phe Thr His Pro Arg
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Leu Pro Gln Arg Gln Gln
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Trp Thr Ser Ala Ala Pro Leu
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Thr Thr Lys Ile Pro Pro Ser
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Met Gly Ser Gly Ser Ser Asn
1               5

<210> SEQ ID NO 166
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Lys Thr Ser Ala Val Leu Pro
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

His Ile Pro Pro Gly Ser Pro
1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ile Pro Thr Leu Pro Ser Ser
1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Ala Gln Leu Met Phe Gln
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asn Thr His Leu Gln Arg Glu
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171
```

```
Leu Val Gly Asn Tyr Thr Pro
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

His Ile Asn Phe Leu His Gly
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

His His His His Lys Pro Thr
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Tyr Lys Ser Ala Pro Pro Tyr
1               5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Leu Pro Gly Gln Gln Phe Gln
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Tyr Asp Asn Arg His Ala Leu
1               5

<210> SEQ ID NO 177
<211> LENGTH: 7
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 177

His Gly Pro Lys Phe Glu Arg
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Leu Thr Pro Met Gly Ala
1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Pro Lys Ser Thr Met Tyr Ser
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Lys Pro Thr Trp Pro Leu Lys
1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Lys Pro His Pro Gln His Ile
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Ala Ser Pro Leu Met His
1               5

```
<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Thr Pro Thr Thr Leu Asn Gln
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Pro Asn Lys Thr Gln Gln
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asp Arg Gln His Leu Lys His
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asn Lys Pro Trp Pro Phe Asn
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

His Gln Thr Lys Ser His His
1               5

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188
```

-continued

Ser Leu Met Arg Leu Gln Pro Gly Tyr Asn Thr Thr
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Ile Gln Leu Ala Asn Pro Pro Arg Leu Tyr Gly
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Tyr Met Pro His Thr Arg Leu Asp Glu Pro Arg Lys
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Ile Pro Ser His Ser Ile His Ser Ala Lys Ala
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asn Thr Pro Ala His Ala Asn Ala Asp Phe Phe Asp
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ile Asp Thr Lys Gln Thr Phe Val Ser Gly Phe Arg
1               5                   10

<210> SEQ ID NO 194
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 194

Tyr Pro His Tyr Ser Leu Pro Gly Ser Ser Thr Leu
1               5                   10

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

His Phe Pro Ser Thr Thr Leu Arg
1               5

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asn Tyr Gln Pro Pro Arg Gly Trp Ile Leu Ala Pro
1               5                   10

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Lys Leu Asp Asn His
1               5

<210> SEQ ID NO 198
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Pro Pro Ser Phe Asp Pro His Arg Thr Thr Arg
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser His Pro Trp Asn Ala Gln Arg Glu Leu Ser Val
1               5                   10
```

```
<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ser Thr Gln Asn Ala Ser Leu Leu Ser Leu Thr Gly
1               5                   10

<210> SEQ ID NO 201
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Asn Ser Ala Ala Ala Asp Cys Tyr Pro Gln Trp Leu Ala Leu Arg Gly
1               5                   10                  15

Pro Ala Ser Gly Arg Pro Pro Pro His
            20                  25

<210> SEQ ID NO 202
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asn Ser Ala Ala Ala Asp Val Tyr Glu Gln Trp Leu Arg Gly Thr Gly
1               5                   10                  15

Pro Arg Ser Gly Arg Pro Pro Pro Ser
            20                  25

<210> SEQ ID NO 203
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Ser Ala Ala Ala Asp Val Tyr Tyr Gln Trp Leu Ala Tyr Thr Gly
1               5                   10                  15

Pro Pro Ser Gly Arg Pro Pro Pro Ile
            20                  25

<210> SEQ ID NO 204
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asn Ser Gln Gln Gln Met Phe Thr Arg Ser Gly Tyr Arg Arg Arg Val
1               5                   10                  15
```

```
Leu Phe Leu Val Val Leu Pro Pro Leu
            20                  25

<210> SEQ ID NO 205
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Asn Ser Ala Ala Ala Asp Ser Tyr Arg Gln Trp Leu Val Ala Val Gly
1               5                   10                  15

Pro Asn Ser Gly Arg Pro Pro Pro Pro
            20                  25

<210> SEQ ID NO 206
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asn Ser Ala Ala Ala Asp Val Tyr Thr Gln Trp Leu Lys Asn Arg Gly
1               5                   10                  15

Pro Ile Ser Gly Arg Pro Pro Pro Leu
            20                  25

<210> SEQ ID NO 207
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asn Ser Ala Ala Ala Asp Thr Tyr Ser Gln Trp Leu Ala Val Glu Gly
1               5                   10                  15

Pro Asp Ser Gly Arg Pro Pro Pro Ala
            20                  25

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asn Ser Gln Gln Gln Ile Leu Thr Leu Ser Gly
1               5                   10

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209
```

```
Asn Ser Ala Ala Ala Asp Phe Tyr
1               5
```

<210> SEQ ID NO 210
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

```
Asn Ser Ala Ala Ala Asp Thr Tyr Arg Gln Trp Leu Ser Pro Ser Gly
1               5                  10                  15

Pro Trp Ser Gly Arg Pro Pro Pro Ser
            20                  25
```

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

```
Asn Ser Gln Gln Gln Ile Ile Thr Ile Ser Gly
1               5                  10
```

<210> SEQ ID NO 212
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

```
Asn Ser Ala Ala Ala Asp Ser Tyr Asn Gln Trp Leu Leu Tyr His Gly
1               5                  10                  15

Pro Ser Ser Gly Arg Pro Pro Pro
            20
```

<210> SEQ ID NO 213
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

```
Asn Ser Ala Ala Ala Asp Thr Tyr Ser Gln Trp Leu Arg Leu Leu Gly
1               5                  10                  15

Pro Pro Ser Gly Arg Pro Pro Pro Arg
            20                  25
```

<210> SEQ ID NO 214
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Asn Ser Ala Ala Ala Asp Pro Tyr Ser Gln Trp Leu Pro Leu Lys Gly
1               5                   10                  15

Pro Pro Ser Gly Arg Pro Pro Pro
            20                  25
```

<210> SEQ ID NO 215
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Asn Ser Ala Ala Ala Asp Ala Tyr Arg Gln Trp Leu Pro Thr Gln Gly
1               5                   10                  15

Pro Pro Ser Gly Arg Pro Pro Pro Gly
            20                  25
```

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Asn Ser Gln Gln Gln Ile Cys Thr Gly Ser Gly
1               5                   10
```

<210> SEQ ID NO 217
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Asn Ser Ala Ala Ala Asp Met Tyr Pro Gln Trp Leu Asn Phe Ala Gly
1               5                   10                  15

Pro Met Ser Gly Arg Pro Pro Pro Leu
            20                  25
```

<210> SEQ ID NO 218
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Asn Ser Ala Ala Ala Asp Thr Tyr Leu Gln Trp Leu Thr Asn Thr Gly
1               5                   10                  15

Pro Phe Ser Gly Arg Pro Pro Pro Arg
            20                  25
```

<210> SEQ ID NO 219
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Asn Ser Ala Ala Ala Asp Cys Tyr Pro Gln Trp Leu Lys Leu Trp Gly
1               5                   10                  15

Pro Cys Ser Gly Arg Pro Pro Lys
            20                  25

<210> SEQ ID NO 220
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid

<400> SEQUENCE: 220

Asn Xaa Ala Ala Ala Asp Lys Tyr Pro Gln Trp Leu His Thr Leu Xaa
1               5                   10                  15

Pro Asn Ser Trp Ser Val Leu Pro Pro Gln
            20                  25

<210> SEQ ID NO 221
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asn Ser Ala Ala Ala Asp Thr Tyr Arg Gln Trp Leu His Val Pro Gly
1               5                   10                  15

Pro Pro Ser Gly Arg Pro Pro Pro Leu
            20                  25

<210> SEQ ID NO 222
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Asn Ser Gln Gln Gln Met Arg Thr Cys Ser Gly Tyr Arg Ile Met Val
1               5                   10                  15

Leu Val Leu Val Val Leu Pro Pro Phe
            20                  25

<210> SEQ ID NO 223
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

```
Asn Ser Ala Ala Ala Asp Ser Tyr Pro Gln Trp Leu Arg Ser Lys Gly
1               5                   10                  15

Pro Pro Ser Gly Pro Ser Ser Pro Pro Val
            20                  25

<210> SEQ ID NO 224
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asn Ser Ala Ala Ala Asp Met Tyr Ser Gln Trp Leu Thr Asn Ser Gly
1               5                   10                  15

Pro Phe Ser Gly Arg Pro Pro Pro Leu
            20                  25

<210> SEQ ID NO 225
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Val Arg Val Leu Leu Leu Val Val Leu Pro Pro Arg
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Arg Ser Leu Val Leu Phe Leu Val Val Leu Pro Pro Val
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ser Val Arg Val Leu Leu Leu Val Val Pro Pro Pro Arg
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Arg Ser Leu Val Leu Phe Leu Val Val Leu Pro Pro Val
1               5                   10
```

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(5)
<223> OTHER INFORMATION: Variable amino acid

<400> SEQUENCE: 229

Val Xaa Xaa Ser Xaa Pro Pro Leu
1               5

<210> SEQ ID NO 230
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ser Val Arg Val Leu Leu Leu Val Val Pro Pro Pro Arg
1               5                   10

<210> SEQ ID NO 231
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Arg Ser Leu Val Leu Phe Leu Val Val Leu Pro Pro Val
1               5                   10

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(5)
<223> OTHER INFORMATION: Variable amino acid

<400> SEQUENCE: 232

Val Xaa Xaa Ser Xaa Pro Pro Leu
1               5

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic

```
peptide

<400> SEQUENCE: 233

Leu Cys Leu Val Leu Ser Leu Val Val Leu Leu Pro Cys Asn
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Arg Arg Arg Val Leu Leu Leu Val Val Leu Pro Pro Arg Asn
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Asn Ser Ala Ala Ala Asp Pro Tyr Trp Gln Trp Leu Asp Ser
1               5                   10

<210> SEQ ID NO 236
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Asn Ser Ala Ala Ala Asp Pro Tyr Thr Gln Trp Leu Asn Cys Ala Gly
1               5                   10                  15

Pro Thr Ser Gly Arg Pro Pro Pro Pro
            20                  25

<210> SEQ ID NO 237
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Asn Ser Ala Ala Ala Asp Lys Tyr Asn Gln Trp Leu Ser Gln Ser Gly
1               5                   10                  15

Pro Leu Ser Gly Arg Pro Pro Pro Asn
            20                  25

<210> SEQ ID NO 238
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238
```

Asn Ser Ala Ala Ala Asp Arg Tyr Leu Gln Trp Leu Pro Pro Ser Gly
1               5                   10                  15

Pro Ile Ser Gly Arg Pro Pro Pro Cys
            20                  25

<210> SEQ ID NO 239
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Asn Ser Ala Ala Ala Asp Pro Tyr Ala Gln Trp Leu His Pro Tyr Gly
1               5                   10                  15

Pro Arg Ser Gly Arg Pro Pro Pro Gln
            20                  25

<210> SEQ ID NO 240
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asn Ser Ala Ala Ala Asp Phe Tyr Pro Gln Trp Leu Asn Met Asn Gly
1               5                   10                  15

Pro Pro Ser Gly Arg Pro Pro Pro Ile
            20                  25

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asn Ser Ala Ala Ala Asp Val Tyr Pro Gln Trp Leu Ser Cys
1               5                   10

<210> SEQ ID NO 242
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (13)..(13)
<223> OTHER INFORMATION: Variable amino acid
<220> FEATURE:
<221> NAME/KEY: MOD_RES
<222> LOCATION: (25)..(25)
<223> OTHER INFORMATION: Variable amino acid

<400> SEQUENCE: 242

Asn Ser Ala Ala Ala Asp Xaa Tyr Thr Gln Trp Leu Xaa Asn Arg Gly

```
                  1               5                  10                  15
Pro Thr Ser Gly Arg Pro Pro Pro Xaa
            20                  25

<210> SEQ ID NO 243
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asn Ser Ala Ala Ala Asp Tyr Tyr His Gln Trp Leu Ala Ser Arg Gly
1               5                  10                  15

Pro Leu Ser Gly Arg Pro Pro Pro His Leu
            20                  25

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asn Ser Gln Gln Gln Ile Gly Thr Val Ser Gly
1               5                  10

<210> SEQ ID NO 245
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asn Ser Ala Ala Ala Asp Leu Tyr Arg Gln Trp Leu Ala Ser Leu Gly
1               5                  10                  15

Pro Val Ser Gly Arg Pro Pro Pro Arg
            20                  25

<210> SEQ ID NO 246
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asn Ser Ala Ala Ala Asp Asp Tyr Pro Gln Trp Leu Leu Glu Thr Gly
1               5                  10                  15

Pro Cys Ser Gly Arg Pro Pro Pro Ser
            20                  25

<210> SEQ ID NO 247
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 247

Asn Ser Ala Ala Ala Asp Thr Tyr Arg Gln Trp Leu Gln Pro Leu Gly
1               5                   10                  15

Pro Pro Ser Gly Arg Pro Pro Gln
            20                  25

<210> SEQ ID NO 248
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asn Ser Ala Ala Ala Asp Leu Tyr Arg Gln Trp Leu Leu Ala Leu Gly
1               5                   10                  15

Pro Glu Ser Gly Arg Pro Pro Pro Leu
            20                  25

<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asn Ser Gln Gln Gln Ile Ser Thr Arg Ser Gly
1               5                   10

<210> SEQ ID NO 250
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Asn Ser Ala Ala Ala Asp Ala Tyr Ala Gln Trp Leu Leu Gly Glu Gly
1               5                   10                  15

Pro Ser Ser Gly Arg Pro Pro Pro Asn
            20                  25

<210> SEQ ID NO 251
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asn Ser Ala Ala Ala Asp Ser Tyr Pro Gln Trp Leu Leu Arg Leu Gly
1               5                   10                  15

Pro Ala Ser Gly Arg Pro Pro Pro Leu
            20                  25

<210> SEQ ID NO 252
<211> LENGTH: 26
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 252

Asn Ser Ala Ala Ala Asp Thr Tyr Leu Gln Trp Leu Pro Gln Arg Gly
1               5                   10                  15

Pro Pro Ser Gly Arg Pro Pro His Val
            20                  25

<210> SEQ ID NO 253
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Asn Ser Ala Ala Ala Asp Asp Tyr Gly Gln Trp Leu Ala Gln Leu Gly
1               5                   10                  15

Pro Leu Ser Gly Arg Pro Pro His
            20                  25

<210> SEQ ID NO 254
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asn Ser Ala Ala Ala Asp Leu Tyr Pro Gln Trp Leu Cys Leu His Gly
1               5                   10                  15

Pro Arg Ser Gly Arg Pro Pro Trp
            20                  25

<210> SEQ ID NO 255
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Asn Ser Ala Ala Ala Asp Ala Tyr Ile Gln Trp Leu Tyr Val Ala Gly
1               5                   10                  15

Pro Ala Ser Gly Arg Pro Pro Arg
            20                  25

<210> SEQ ID NO 256
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asn Ser Ala Ala Ala Asp Ser Tyr Thr Gln Trp Leu Pro Gly His Gly
1               5                   10                  15

Pro Ala Ser Gly Arg Pro Pro Leu Val
            20                  25
```

```
<210> SEQ ID NO 257
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Asn Ser Ala Ala Ala Asp Trp Tyr Tyr Gln Trp Leu Ser Ala Ser Gly
1               5                   10                  15

Pro Phe Val Trp Ser Ser Leu Pro Pro Arg
            20                  25

<210> SEQ ID NO 258
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asn Ser Ala Ala Ala Asp Gln Tyr Pro Gln Trp Leu Gly Leu Arg Gly
1               5                   10                  15

Pro Thr Ser Gly Arg Pro Pro Ala
            20                  25

<210> SEQ ID NO 259
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Asn Ser Ala Ala Ala Asp Ala Tyr Trp Gln Trp Leu Thr Ile Tyr Gly
1               5                   10                  15

Pro Val Ser Gly Arg Pro Pro Gln
            20                  25

<210> SEQ ID NO 260
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Asn Ser Ala Ala Ala Asp Val Tyr Met Gln Leu Val Ile Val Tyr Gly
1               5                   10                  15

Pro Thr Ser Gly Arg Pro Pro Ile
            20                  25

<210> SEQ ID NO 261
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261
```

```
Asn Ser Ala Ala Ala Asp Pro Tyr Phe Gln Trp Leu Lys Ile Pro Gly
1               5                   10                  15

Pro Pro Ser Gly Arg Pro Pro Pro Arg
            20                  25
```

<210> SEQ ID NO 262
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

```
Asn Ser Ala Ala Ala Asp Thr Tyr Leu Gln Trp Leu Asp His Thr Gly
1               5                   10                  15

Pro Tyr Ser Gly Arg Pro Pro Pro Tyr
            20                  25
```

<210> SEQ ID NO 263
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

```
Asn Ser Ala Ala Ala Asp Ala Tyr Gly Gln Trp Leu Pro Ser Thr Gly
1               5                   10                  15

Pro Lys Ser Gly Arg Pro Pro Pro Leu Asn
            20                  25
```

<210> SEQ ID NO 264
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

```
Asn Ser Ala Ala Ala Asp Cys Tyr Thr Gln Trp Leu Ala Ser Pro Gly
1               5                   10                  15

Pro Lys Ser Gly Arg Pro Pro Pro His Val
            20                  25
```

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

```
Asn Ser Gln Gln Gln Ile Arg Thr Val Ser Gly
1               5                   10
```

<210> SEQ ID NO 266
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 266

Asn Ser Ala Ala Ala Asp Phe Tyr Val Gln Trp Leu Phe Thr Ser Gly
1               5                   10                  15

Pro Pro Ser Gly Arg Pro Pro Asp
            20                  25

<210> SEQ ID NO 267
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Asn Ser Ala Ala Ala Asp Leu Tyr Tyr Gln Trp Leu Ala Thr Tyr Gly
1               5                   10                  15

Pro Ala Ser Gly Arg Pro Pro Met
            20                  25

<210> SEQ ID NO 268
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asn Ser Ala Ala Ala Asp His Tyr Gly Gln Trp Leu Ser Val Pro Gly
1               5                   10                  15

Pro Asn Ser Gly Arg Pro Pro Ile
            20                  25

<210> SEQ ID NO 269
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Asn Ser Ala Ala Ala Asp Val Tyr Ile Gln Trp Leu Phe Val Thr Gly
1               5                   10                  15

Pro Phe Ser Gly Arg Pro Pro His
            20                  25

<210> SEQ ID NO 270
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Asn Ser Ala Ala Ala Asp Leu Tyr Ala Gln Trp Leu Ala Arg Leu Gly
1               5                   10                  15

Pro Pro Ser Gly Arg Pro Pro Pro
            20                  25

<210> SEQ ID NO 271
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Asn Ser Ala Ala Ala Asp Ser Tyr Thr Gln Trp Leu Pro Gly His Gly
1               5                   10                  15

Pro Ala Ser Gly Arg Pro Pro Leu Val
            20                  25

<210> SEQ ID NO 272
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Asn Ser Ala Ala Ala Asp Trp Tyr Tyr Gln Trp Leu Ser Ala Ser Gly
1               5                   10                  15

Pro Phe Val Trp Ser Ser Leu Pro Pro Arg
            20                  25

<210> SEQ ID NO 273
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Asn Ser Ala Ala Ala Asp Trp Tyr Ala Gln Trp Leu Leu Thr Arg Gly
1               5                   10                  15

Pro Ala Ser Gly Arg Pro Pro Pro Ser
            20                  25

<210> SEQ ID NO 274
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Asn Ser Ala Ala Ala Asp Pro Tyr Glu Gln Trp Leu Asn Val Pro Gly
1               5                   10                  15

Pro Pro Ser Gly Pro Ser Ser Pro Pro Arg Asn
            20                  25

<210> SEQ ID NO 275
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Asn Ser Ala Ala Ala Asp Ala Tyr Trp Gln Trp Leu Thr Ile Tyr Gly
1               5                   10                  15
```

```
Pro Val Ser Gly Arg Pro Pro Gln
            20                  25

<210> SEQ ID NO 276
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Asn Ser Ala Ala Ala Asp Thr Tyr Tyr Gln Trp Leu Thr Gln Thr Gly
1               5                   10                  15

Pro Leu Ser Gly Arg Pro Pro Pro Pro
            20                  25

<210> SEQ ID NO 277
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asn Ser Ala Ala Ala Asp Pro Tyr Phe Gln Trp Leu Lys Ile Pro Gly
1               5                   10                  15

Pro Pro Ser Gly Arg Pro Pro Pro Arg
            20                  25

<210> SEQ ID NO 278
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Variable amino acid
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (26)..(26)
<223> OTHER INFORMATION: Variable amino acid

<400> SEQUENCE: 278

Asn Ser Ala Ala Ala Asp Thr Tyr Leu Xaa Trp Xaa Asp His Thr Gly
1               5                   10                  15

Pro Tyr Ser Gly Arg Pro Pro Pro Tyr Xaa
            20                  25

<210> SEQ ID NO 279
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asn Ser Ala Ala Ala Asp Met Tyr Leu Gln Trp Leu Ala Ser Ser Gly
```

```
Pro Arg Ser Gly Arg Pro Pro Pro Tyr
            20                  25

<210> SEQ ID NO 280
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Asn Ser Ala Ala Ala Asp Gln Tyr Ser Gln Trp Leu Val Val Gly Gly
1               5                   10                  15

Pro Ser Ser Gly Arg Pro Ser Pro Pro Val Thr
            20                  25

<210> SEQ ID NO 281
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(15)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid
<220> FEATURE:
<221> NAME/KEY: MOD_RES
<222> LOCATION: (25)..(25)
<223> OTHER INFORMATION: Variable amino acid

<400> SEQUENCE: 281

Asn Ser Ala Ala Ala Asp Trp Tyr Thr Ser Val Val Xaa Xaa Xaa Gly
1               5                   10                  15

Ser Xaa Phe Trp Ser Ser Ser Pro Xaa Val
            20                  25

<210> SEQ ID NO 282
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Asn Ser Ala Ala Ala Asp Ser Tyr Lys Gln Trp Leu Pro Ala Leu Gly
1               5                   10                  15

Pro Ser Ser Gly Arg Pro Pro Pro Ser
            20                  25

<210> SEQ ID NO 283
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283
```

-continued

Asn Ser Ala Ala Ala Asp Ala Tyr Arg Ser Val Val Arg Ser Tyr Trp
1               5                   10                  15

Ser Tyr Phe Trp Ser Ser Ser Pro Pro Leu
            20                  25

<210> SEQ ID NO 284
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Asn Ser Ala Ala Ala Asp Tyr Tyr Arg Gln Trp Leu Ala Ile Ser Gly
1               5                   10                  15

Pro Leu Ser Gly Arg Pro Pro Pro Arg
            20                  25

<210> SEQ ID NO 285
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Asn Ser Ala Ala Ala Asp Asn Tyr Pro Gln Trp Leu Pro Pro Ala Gly
1               5                   10                  15

Pro Thr Ser Gly Arg Pro Pro Pro Gln
            20                  25

<210> SEQ ID NO 286
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Asn Ser Ala Ala Ala Asp Arg Tyr His Gln Trp Leu Arg Gln Lys Gly
1               5                   10                  15

Pro Gly Ser Gly Arg Pro Pro Pro Ala
            20                  25

<210> SEQ ID NO 287
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Asn Ser Ala Ala Ala Asp Leu Tyr Ser Gln Trp Leu Phe
1               5                   10

<210> SEQ ID NO 288
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 288

Asn Ser Ala Ala Ala Asp Lys Tyr
1               5

<210> SEQ ID NO 289
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Asn Ser Ala Ala Ala Asp His Tyr
1               5

<210> SEQ ID NO 290
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Asn Ser Ala Ala Ala Asp
1               5

<210> SEQ ID NO 291
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Asn Ser Ala Ala Ala Asp Gly Tyr Gly Gln Trp Leu His Lys Trp Gly
1               5                   10                  15

Pro Ser Ser Gly Arg Pro Pro Pro Arg
            20                  25

<210> SEQ ID NO 292
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Variable amino acid

<400> SEQUENCE: 292

Asn Ser Ala Ala Ala Asp Ile Tyr Val Gln Trp Leu His Glu Leu Gly
1               5                   10                  15

Pro Thr Ser Gly Leu Pro Xaa Arg Lys
            20                  25

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 293

Asn Ser Gln Gln Gln Ile Arg Thr Arg Ser Gly
1               5                   10

<210> SEQ ID NO 294
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Variable amino acid

<400> SEQUENCE: 294

Asn Ser Ala Ala Ala Asp Ile Tyr Leu Gln Trp Leu Gln Met Met Gly
1               5                   10                  15

Pro Leu Ser Gly Xaa Pro Pro Pro Thr
            20                  25

<210> SEQ ID NO 295
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Asn Ser Ala Ala Ala Asp Thr Tyr Tyr Gln Trp Leu Asn Pro Gln Gly
1               5                   10                  15

Pro Phe Ser Gly Arg Pro Pro Pro Ser
            20                  25

<210> SEQ ID NO 296
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Asn Ser Ala Ala Ala Asp Val Tyr Thr Gln Trp Leu Gly Lys Ser Gly
1               5                   10                  15

Pro Leu Ser Gly Arg Pro Pro Pro Ala Tyr
            20                  25

<210> SEQ ID NO 297
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Variable amino acid
<220> FEATURE:
<221> NAME/KEY: MOD_RES
<222> LOCATION: (23)..(25)
<223> OTHER INFORMATION: Variable amino acid

```
<400> SEQUENCE: 297

Asn Ser Ala Ala Ala Asp Glu Tyr Pro Gln Trp Leu Asn Thr Glu Gly
1               5                   10                  15

Pro His Ser Gly Xaa Pro Xaa Xaa Xaa
            20                  25

<210> SEQ ID NO 298
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asn Ser Ala Ala Ala Asp Val Tyr Val Gln Trp Leu Asn Ser Arg Gly
1               5                   10                  15

Pro Pro Ser Gly Arg Pro Pro Pro Leu
            20                  25

<210> SEQ ID NO 299
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Asn Ser Ala Ala Ala Asp Pro Tyr Arg Gln Trp Leu Arg Thr Pro Gly
1               5                   10                  15

Pro Arg Ser Gly Arg Pro Pro Pro His Leu
            20                  25

<210> SEQ ID NO 300
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Asn Ser Ala Ala Ala Asp Gln Tyr Thr Gln Trp Leu Tyr Thr Lys Gly
1               5                   10                  15

Pro Phe Ser Gly Arg Pro Pro Pro His
            20                  25

<210> SEQ ID NO 301
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(24)
<223> OTHER INFORMATION: Variable amino acid

<400> SEQUENCE: 301

Asn Ser Ala Ala Ala Asp Gln Tyr Arg Gln Trp Leu Trp Pro Thr Gly
1               5                   10                  15

Pro Gln Ser Gly Leu Pro Xaa Xaa Gly
            20                  25
```

```
<210> SEQ ID NO 302
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asn Ser Ala Ala Ala Asp Val Tyr Arg Gln Trp Leu Arg Pro Val Gly
1               5                   10                  15

Pro Thr Ser Gly Arg Pro Pro Arg
            20                  25

<210> SEQ ID NO 303
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Asn Ser Ala Ala Ala Asp Gln Tyr Leu Gln Trp Leu Leu Pro Pro Gly
1               5                   10                  15

Pro Ser Ser Gly Arg Pro Pro Lys
            20                  25

<210> SEQ ID NO 304
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Asn Ser Ala Ala Ala Asp Pro Tyr Pro Gln Trp Leu Met Leu Arg Gly
1               5                   10                  15

Pro Thr Ser Gly Arg Pro Ser Pro His Leu Asn
            20                  25

<210> SEQ ID NO 305
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Asn Ser Ala Ala Ala Asp
1               5

<210> SEQ ID NO 306
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Asn Ser Ala Ala Ala Asp Pro Tyr Trp Gln Trp Leu Leu Leu Thr Gly
1               5                   10                  15
```

Pro

<210> SEQ ID NO 307
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Asn Ser Ala Ala Thr Asp Arg Tyr Ala Gln Trp Leu Ala Ala Tyr Gly
1               5                   10                  15

Pro Arg Ser Gly Arg Pro Pro Pro Pro
            20                  25

<210> SEQ ID NO 308
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Variable amino acid

<400> SEQUENCE: 308

Asn Ser Ala Ala Ala Asp Ser Tyr Lys Gln Trp Leu Gly Glu Leu Gly
1               5                   10                  15

Pro Pro Ser Gly Leu Xaa Ser Pro Pro Leu
            20                  25

<210> SEQ ID NO 309
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Asn Ser Ala Ala Ala Asp Leu Tyr Gln Gln Trp Leu Ser
1               5                   10

<210> SEQ ID NO 310
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Variable amino acid
<220> FEATURE:
<221> NAME/KEY: MOD_RES
<222> LOCATION: (24)..(24)
<223> OTHER INFORMATION: Variable amino acid

<400> SEQUENCE: 310

Asn Ser Ala Ala Ala Asp Ser Tyr Ser Gln Trp Leu Pro Gly Pro Gly
1               5                   10                  15

Pro Asn Ser Gly Xaa Pro Gln Xaa His Val
            20                  25

```
<210> SEQ ID NO 311
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Asn Ser Ala Ala Ala Asp Trp Tyr Cys Gln Trp Leu Thr Arg Met Gly
1               5                   10                  15

Pro Pro Ser Gly Arg Pro Pro Pro Thr
            20                  25

<210> SEQ ID NO 312
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Asn Ser Ala Ala Ala Asp Asp Tyr Ala Gln Trp Leu Gly Val Glu Gly
1               5                   10                  15

Pro Arg Ser Gly Pro Pro Pro Thr
            20

<210> SEQ ID NO 313
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Asn Ser Ala Ala Ala Asp Gln Tyr Leu Gln Trp Leu Arg Met Thr Gly
1               5                   10                  15

Pro Met Ser Gly Arg Pro Pro Pro
            20

<210> SEQ ID NO 314
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Asn Ser Gln Gln Gln Ile Ile Thr Gly Ser Gly
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asn Ser Gln Gln Gln Ile Phe Thr Ser Ser Gly
1               5                   10
```

```
<210> SEQ ID NO 316
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Asn Ser Ala Ala Ala Asp Phe Tyr Gly Gln Trp Leu Val Lys Arg Gly
1               5                   10                  15

Pro Asn Ser Gly Arg Pro Pro Asn
            20                  25

<210> SEQ ID NO 317
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Asn Ser Ala Ala Ala Asp Glu Tyr Val Gln Trp Leu His Pro Cys Gly
1               5                   10                  15

Pro Asp Ser Gly Arg Pro Pro Lys
            20

<210> SEQ ID NO 318
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Variable amino acid

<400> SEQUENCE: 318

Asn Ser Ala Ala Ala Asp Thr Tyr Leu Gln Trp Leu Leu Gln Leu Gly
1               5                   10                  15

Pro His Ser Gly Leu Xaa Pro Gly Tyr
            20                  25

<210> SEQ ID NO 319
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Asn Ser Ala Ala Ala Asp Pro Tyr Trp Gln Trp Leu Leu Leu Thr Gly
1               5                   10                  15

Pro

<210> SEQ ID NO 320
<211> LENGTH: 25
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 320

Asn Ser Ala Ala Thr Asp Arg Tyr Ala Gln Trp Leu Ala Ala Tyr Gly
1               5                   10                  15

Pro Arg Ser Gly Arg Pro Pro Pro
            20                  25

<210> SEQ ID NO 321
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Asn Ser Ala Ala Ala Asp Ser Tyr Lys Gln Trp Leu Gly Glu Leu Gly
1               5                   10                  15

Pro Pro Ser Gly Arg Ser Ser Pro Leu
            20                  25

<210> SEQ ID NO 322
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Asn Ser Ala Ala Ala Asp Ala Tyr Leu Gln Trp Leu Ser Gln Val Gly
1               5                   10                  15

Pro His Ser Gly Arg Pro Pro Pro Ala Val
            20                  25

<210> SEQ ID NO 323
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Asn Ser Ala Ala Ala Asp Ser Tyr Ser Gln Trp Leu Pro Gly Pro Gly
1               5                   10                  15

Pro Asn Ser Gly Arg Pro Pro Pro Met
            20                  25

<210> SEQ ID NO 324
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Asn Ser Ala Ala Ala Asp Trp Tyr Cys Gln Trp Leu Thr Arg Met Gly
1               5                   10                  15

Pro Pro Ser Gly Arg Pro Pro Pro His Leu
            20                  25

```
<210> SEQ ID NO 325
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Asn Ser Ala Ala Ala Asp Asp Tyr Ala Gln Trp Leu Gly Val Glu Gly
1               5                   10                  15

Pro Arg Ser Gly Arg Pro Pro Thr
            20                  25

<210> SEQ ID NO 326
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Asn Ser Ala Ala Ala Asp Gln Tyr Leu Gln Trp Leu Arg Met Thr Gly
1               5                   10                  15

Pro Met Ser Gly Arg Pro Pro Pro
            20

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Asn Ser Gln Gln Gln Ile Ile Thr Gly Ser Gly
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Asn Ser Gln Gln Gln Ile Phe Thr Ser Ser Gly
1               5                   10

<210> SEQ ID NO 329
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Asn Ser Ala Ala Ala Asp Phe Tyr Gly Gln Trp Leu Val Lys Arg Gly
1               5                   10                  15

Pro Asn Ser Gly Arg Pro Pro Pro Asn
            20                  25
```

```
<210> SEQ ID NO 330
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Asn Ser Ala Ala Ala Asp Glu Tyr Val Gln Trp Leu His Pro Cys Gly
1               5                   10                  15

Pro Asp Ser Gly Arg Pro Pro Pro Lys
            20                  25

<210> SEQ ID NO 331
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Asn Ser Ala Ala Ala Asp Gln Tyr Gln Gln Trp Leu Lys Leu Leu Gly
1               5                   10                  15

Pro Arg Ser Gly Arg Pro Pro Pro Val
            20                  25

<210> SEQ ID NO 332
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asn Ser Ala Ala Ala Asp Ile Tyr Lys Gln Trp Leu His Asp Asp Gly
1               5                   10                  15

Pro Met Ser Gly Arg Pro Pro Pro Arg
            20                  25

<210> SEQ ID NO 333
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Asn Ser Gln Gln Gln Ile Val Thr Leu Ser Gly Tyr Arg Arg Met Val
1               5                   10                  15

Leu Val Leu Val Val Leu Pro Pro Cys Asn
            20                  25

<210> SEQ ID NO 334
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Asn Ser Ala Ala Ala Asp Thr Tyr Leu Gln Trp Leu Leu Gln Leu Gly
```

```
1               5                   10                  15

Pro His Ser Gly Arg Pro Pro Pro Tyr
            20                  25

<210> SEQ ID NO 335
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Asn Ser Ala Ala Ala Asp
1               5

<210> SEQ ID NO 336
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Asn Ser Ala Ala Ala Asp Pro Tyr Trp Gln Trp Leu Leu Leu Thr Gly
1               5                   10                  15

Pro

<210> SEQ ID NO 337
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Asn Ser Ala Ala Thr Asp Arg Tyr Ala Gln Trp Leu Ala Ala Tyr Gly
1               5                   10                  15

Pro Arg Ser Gly Arg Pro Pro Pro Pro
            20                  25

<210> SEQ ID NO 338
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Asn Ser Ala Ala Ala Asp Ser Tyr Lys Gln Trp Leu Gly Glu Leu Gly
1               5                   10                  15

Pro Pro Ser Gly Arg Ser Ser Pro Pro Leu
            20                  25

<210> SEQ ID NO 339
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339
```

-continued

Asn Ser Ala Ala Ala Asp Leu Tyr Gln Gln Trp Leu Ser
1               5                   10

<210> SEQ ID NO 340
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Asn Ser Ala Ala Ala Asp Ala Tyr Leu Gln Trp Leu Ser Gln Val Gly
1               5                   10                  15

Pro His Ser Gly Arg Pro Pro Pro Ala Val
            20                  25

<210> SEQ ID NO 341
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asn Ser Ala Ala Ala Asp Trp Tyr Cys Gln Trp Leu Thr Arg Met Gly
1               5                   10                  15

Pro Pro Ser Gly Arg Pro Pro Pro His Leu
            20                  25

<210> SEQ ID NO 342
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Asn Ser Ala Ala Ala Asp Asp Tyr Ala Gln Trp Leu Gly Val Glu Gly
1               5                   10                  15

Pro Arg Ser Gly Arg Pro Pro Pro Thr
            20                  25

<210> SEQ ID NO 343
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Asn Ser Ala Ala Ala Asp Gln Tyr Leu Gln Trp Leu Arg Met Thr Gly
1               5                   10                  15

Pro Met Ser Gly Arg Pro Pro Pro
            20

<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Asn Ser Ala Ala Ala Asp Pro Tyr Trp Gln Trp Leu Leu Leu Thr Gly
1               5                   10                  15

Pro

<210> SEQ ID NO 345
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Asn Ser Ala Ala Thr Asp Arg Tyr Ala Gln Trp Leu Ala Ala Tyr Gly
1               5                   10                  15

Pro Arg Ser Gly Arg Pro Pro Pro Pro
            20                  25

<210> SEQ ID NO 346
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Asn Ser Ala Ala Ala Asp Gln Tyr Leu Gln Trp Leu Arg Met Thr Gly
1               5                   10                  15

Pro Met Ser Gly Arg Pro Pro Pro
            20

<210> SEQ ID NO 347
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Asn Ser Ala Ala Ala Asp Lys Tyr Ala Gln Trp Leu Leu Ala Ala Gly
1               5                   10                  15

Pro Thr Ser Gly Arg Pro Pro Pro Pro
            20                  25

<210> SEQ ID NO 348
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Asn Ser Ala Ala Ala Asp Ala Tyr Glu Gln Trp Leu Pro Arg Pro Gly
1               5                   10                  15

Pro Asp Ser Gly Arg Pro Pro Arg Val
            20                  25

<210> SEQ ID NO 349

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Asn Ser Ala Ala Ala Asp Gln Tyr Pro Gln Trp Leu Thr Met Asp Gly
1               5                   10                  15

Pro Pro Ser Gly Arg Pro Pro Gly
            20                  25

<210> SEQ ID NO 350
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Asn Ser Ala Ala Ala Asp Ala Tyr Met Gln Trp Leu Thr Leu Met Gly
1               5                   10                  15

Pro Thr Ser Gly Arg Pro Pro Pro Leu
            20                  25

<210> SEQ ID NO 351
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asn Ser Gln Gln Gln Ile Leu Thr Arg Ser Gly
1               5                   10

<210> SEQ ID NO 352
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Asn Ser Ala Ala Ala Asp Ile Tyr Ile Gln Trp Leu Thr Arg Thr Gly
1               5                   10                  15

Pro Thr Ser Gly Arg Pro Pro Pro Phe
            20                  25

<210> SEQ ID NO 353
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Asn Ser Ala Ala Ala Asp Ala Tyr Asp Gln Trp Leu Pro Leu Pro Gly
1               5                   10                  15

Pro Lys Ser Gly Arg Pro Pro Pro Ala
            20                  25
```

```
<210> SEQ ID NO 354
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asn Ser Ala Ala Ala Asp Pro Tyr Pro Gln Trp Leu Ser Ser Arg Gly
1               5                   10                  15

Pro Leu Val Trp Ser Ser Ser Pro His Val
            20                  25

<210> SEQ ID NO 355
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Asn Ser Ala Ala Ala Asp Pro Tyr Leu Gln Trp Leu Val Leu Arg Gly
1               5                   10                  15

Pro His Ser Gly Arg Pro Pro Trp
            20                  25

<210> SEQ ID NO 356
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Variable amino acid

<400> SEQUENCE: 356

Asn Ser Ala Ala Ala Asp Asp Tyr Thr Gln Xaa Val Ser Asp Ser Gly
1               5                   10                  15

Ser Ser Val Trp Ser Ser Ser Pro Pro Val
            20                  25

<210> SEQ ID NO 357
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Asn Ser Ala Ala Ala Asp Arg Tyr Leu Gln Trp Leu Ser Thr Ile Gly
1               5                   10                  15

Pro Lys Ser Gly Arg Pro Pro Met
            20                  25

<210> SEQ ID NO 358
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 358

Asn Ser Ala Ala Ala Asp Ile Tyr Pro Gln Trp Leu Leu Asn Ser Gly
1               5                   10                  15

Pro Ser Ser Gly Arg Pro Pro Thr
            20                  25

<210> SEQ ID NO 359
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Asn Ser Ala Ala Ala Asp Ser Tyr Ser Gln Trp Leu Pro Val Leu Gly
1               5                   10                  15

Pro Val Ser Gly Arg Pro Pro Pro Arg
            20                  25

<210> SEQ ID NO 360
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Asn Ser Ala Ala Ala Asp Pro Tyr Arg Gln Trp Leu Val Thr Met Gly
1               5                   10                  15

Pro Pro Ser Gly Arg Pro Pro Pro Pro
            20                  25

<210> SEQ ID NO 361
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Asn Ser Ala Ala Ala Asp Ser Tyr His Gln Trp Leu Ser Thr Tyr Gly
1               5                   10                  15

Pro Asp Ser Gly Arg Pro Pro Pro Gln
            20                  25

<210> SEQ ID NO 362
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Asn Ser Gln Gln Gln Ile Trp Gln Trp Leu His Thr Gln Gly Pro Arg
1               5                   10                  15

Ser Gly Arg Pro Pro Pro Asn
            20
```

```
<210> SEQ ID NO 363
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Asn Ser Gln Gln Gln Ile Arg Thr Phe Ser Gly
1               5                   10

<210> SEQ ID NO 364
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Asn Ser Ala Ala Ala Asp Lys Tyr Ala Gln Trp Leu Leu Ala Ala Gly
1               5                   10                  15

Pro Thr Ser Gly Arg Pro Pro Pro Pro
            20                  25

<210> SEQ ID NO 365
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Asn Ser Ala Ala Ala Asp Ala Tyr Glu Gln Trp Leu Pro Arg Pro Gly
1               5                   10                  15

Pro Asp Ser Gly Arg Pro Pro Pro Arg Val
            20                  25

<210> SEQ ID NO 366
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Asn Ser Ala Ala Ala Asp Lys Tyr Ala Gln Trp Leu Leu Ala Ala Gly
1               5                   10                  15

Pro Thr Ser Gly Arg Pro Pro Pro Pro
            20                  25

<210> SEQ ID NO 367
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Asn Ser Ala Ala Ala Asp Ala Tyr Glu Gln Trp Leu Pro Arg Pro Gly
1               5                   10                  15
```

```
Pro Asp Ser Gly Arg Pro Pro Pro Arg Val
            20                  25

<210> SEQ ID NO 368
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Variable amino acid
<220> FEATURE:
<221> NAME/KEY: MOD_RES
<222> LOCATION: (24)..(24)
<223> OTHER INFORMATION: Variable amino acid

<400> SEQUENCE: 368

Asn Ser Ala Ala Ala Asp Pro Tyr Ile Gln Trp Leu His Lys His Gly
1               5                   10                  15

Pro Ile Ser Gly Arg Xaa Glu Xaa Pro Ser Arg Thr Leu Leu His
            20                  25                  30

<210> SEQ ID NO 369
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gly Lys His Ser Ile Asn Leu
1               5

<210> SEQ ID NO 370
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gly Asn Pro Leu Trp Gly Thr
1               5

<210> SEQ ID NO 371
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ser Ala Arg Gln Gln Ala Phe
1               5

<210> SEQ ID NO 372
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 372

Lys Pro Tyr Thr Tyr Leu Thr
1               5

<210> SEQ ID NO 373
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ser Pro Gln Thr His Gln Ala
1               5

<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Pro Leu Phe Ser Thr Arg Met
1               5

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

His Asn Leu Gln Pro Gly His
1               5

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Trp Ser Val Phe Pro Tyr Ser
1               5

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Arg Pro Thr Ala Gln Tyr Asp
1               5

<210> SEQ ID NO 378
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 378

Gly Leu Ser His Thr Ala Pro
1               5

<210> SEQ ID NO 379
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Variable amino acid

<400> SEQUENCE: 379

Leu Leu Leu Val Leu Val Leu Val Val Leu Pro Xaa Cys Asn
1               5                   10

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Thr Thr Leu His His Thr Asn
1               5

<210> SEQ ID NO 381
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Gln His Pro Pro Trp Arg Val
1               5

<210> SEQ ID NO 382
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Cys Arg Leu Val Leu Gly Leu Val Val Leu Pro Pro Ser Asn
1               5                   10

<210> SEQ ID NO 383
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 383

His His Ser Leu Thr Val Thr
1               5

<210> SEQ ID NO 384
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ala Ala Thr Asp Leu Arg Thr
1               5

<210> SEQ ID NO 385
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ser Pro Leu Pro Gln Ser Gln
1               5

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ser Pro Asn Lys Pro Leu His
1               5

<210> SEQ ID NO 387
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gly Met Pro Arg Pro Ala Ser
1               5

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ser Pro Ser Ser Ala Thr Ala
1               5

<210> SEQ ID NO 389
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 389

Gly Pro Phe Ser Thr Arg Asp
1               5

<210> SEQ ID NO 390
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ala Ser Pro Leu Thr
1               5

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Val Arg Pro His Gln Glu Phe
1               5

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Thr Pro Pro Thr Met Asp His
1               5

<210> SEQ ID NO 393
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ser Ile Glu Arg Ser Ala Asn
1               5

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Phe Gln Gly Asp Lys Thr Phe
1               5
```

<210> SEQ ID NO 395
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Ser Thr Thr Pro Leu Gly His
1               5

<210> SEQ ID NO 396
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Leu Pro Asp Asn Gln His Ser
1               5

<210> SEQ ID NO 397
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gln Thr Lys Thr Thr Met Ser
1               5

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Thr Val Asn Lys Pro Val Leu
1               5

<210> SEQ ID NO 399
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Arg Leu Gln Asp Thr Ala Gln
1               5

<210> SEQ ID NO 400
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Val His Thr Gln Gly Lys Ala
1               5

<210> SEQ ID NO 401
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

His Pro Thr Gln His Lys Asn
1               5

<210> SEQ ID NO 402
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gln Ala Lys Trp His Lys Ser
1               5

<210> SEQ ID NO 403
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Arg Leu Pro Ala Pro Pro His
1               5

<210> SEQ ID NO 404
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Tyr Pro Gln Glu Arg Thr Pro
1               5

<210> SEQ ID NO 405
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Met Pro Ser Arg Glu Pro Ile
1               5

<210> SEQ ID NO 406
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Phe Ser Asn His Ser Pro Trp
1               5

<210> SEQ ID NO 407
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Asn Ala Thr Leu Thr Arg Leu
1               5

<210> SEQ ID NO 408
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Ala Pro Trp Met Arg Pro Asp
1               5

<210> SEQ ID NO 409
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

His Pro His His Arg Trp Ala
1               5

<210> SEQ ID NO 410
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Ile Val Ala Thr Gln Ile Tyr
1               5

<210> SEQ ID NO 411
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Thr Asn Ser Asn Ala His His
```

-continued

```
1               5

<210> SEQ ID NO 412
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Ser Val Ala Leu Ser Ser Arg
1               5

<210> SEQ ID NO 413
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Ser Ile Leu Pro Arg Pro Phe
1               5

<210> SEQ ID NO 414
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Ser Ser Asn Ser Ser His His
1               5

<210> SEQ ID NO 415
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Ser His Val Asn Met Lys Asn
1               5

<210> SEQ ID NO 416
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Leu Asp Leu Arg Phe Pro
1               5

<210> SEQ ID NO 417
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 417

Pro Pro Asn Lys Ala Leu His
1               5

<210> SEQ ID NO 418
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Ser Pro Trp Gly Leu Ala Gln
1               5

<210> SEQ ID NO 419
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Ser Val Met Lys Gln Lys Met
1               5

<210> SEQ ID NO 420
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gln Ser Val Trp Gln Thr Asn
1               5

<210> SEQ ID NO 421
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gln Pro Ala Leu Ser Pro Arg
1               5

<210> SEQ ID NO 422
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Leu Asp Pro Thr Gly Arg His
1               5

<210> SEQ ID NO 423

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid

<400> SEQUENCE: 423

Xaa Xaa Pro Xaa Ser Xaa Xaa
1               5

<210> SEQ ID NO 424
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Ser Gln His Trp Ala Pro Ser Gly Ser Pro Trp Lys
1               5                   10

<210> SEQ ID NO 425
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Leu Pro Ile Pro Glu Arg
1               5

<210> SEQ ID NO 426
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Phe Asp Asn Phe Lys Thr Ile Ser Ser Ser Ser His
1               5                   10

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ser Thr Thr Leu Asn Asn Thr Thr Trp Arg Leu Tyr
1               5                   10
```

<210> SEQ ID NO 428
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Gln Glu Ala Leu Ser Arg Ser Pro Tyr Asp Ala Arg
1               5                   10

<210> SEQ ID NO 429
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Thr Trp Asn Ile Pro Asp Val Asp
1               5

<210> SEQ ID NO 430
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gly Leu Glu Phe Lys Ser Pro Leu Pro Ala Ser Ser
1               5                   10

<210> SEQ ID NO 431
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Val Ser Ser Gln Tyr Ser Val Thr Pro Ala Arg Val
1               5                   10

<210> SEQ ID NO 432
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Asp Ile His Ala Arg Ser Ala
1               5

<210> SEQ ID NO 433
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 433

Thr Ser Lys Gly Pro Thr Gln
1               5

<210> SEQ ID NO 434
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Thr Asn Thr Ser Val Lys Val
1               5

<210> SEQ ID NO 435
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Val Pro Ser Thr Leu Pro Arg
1               5

<210> SEQ ID NO 436
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Ser Asn Ser Thr Leu His Lys
1               5

<210> SEQ ID NO 437
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gln Ser Val Trp Gln Thr Asn
1               5

<210> SEQ ID NO 438
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Gln Phe Ser Thr Asn Pro Arg
1               5

<210> SEQ ID NO 439
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

His Tyr Pro Ser Ile Thr His
1               5

<210> SEQ ID NO 440
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Asp Pro Leu Leu Pro Pro Met
1               5

<210> SEQ ID NO 441
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Gly Ala Ile Pro His Phe Arg
1               5

<210> SEQ ID NO 442
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Ser His Val Asn Met Lys Asn
1               5

<210> SEQ ID NO 443
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Gln Pro Thr Lys Val Pro Gly
1               5

<210> SEQ ID NO 444
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Leu Cys Arg Val Leu Val Leu Val Val Leu Pro Pro Ile Asn
```

-continued

```
1               5                   10

<210> SEQ ID NO 445
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Phe Asn Thr Leu Arg Thr Ala
1               5

<210> SEQ ID NO 446
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Leu Asp Leu Arg Phe Pro Gln
1               5

<210> SEQ ID NO 447
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Asn Ser Gln Gln Gln Ile Ile Thr Arg Ser Gly Tyr Arg Met Arg Val
1               5                   10                  15

Leu Arg Ser Gly Arg Pro Pro Pro Arg
            20                  25

<210> SEQ ID NO 448
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Variable amino acid
<220> FEATURE:
<221> NAME/KEY: MOD_RES
<222> LOCATION: (23)..(24)
<223> OTHER INFORMATION: Variable amino acid

<400> SEQUENCE: 448

Asn Ser Ala Ala Ala Asp Ser Tyr Asn Gln Trp Leu His Thr Thr Gly
1               5                   10                  15

Pro Ser Ser Gly Xaa Pro Xaa Xaa Pro Leu
            20                  25

<210> SEQ ID NO 449
<211> LENGTH: 25
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<221> NAME/KEY: MOD_RES
<222> LOCATION: (23)..(24)
<223> OTHER INFORMATION: Variable amino acid

<400> SEQUENCE: 449

Asn Ser Ala Ala Ala Asp Asn Tyr Lys Gln Trp Leu Asn Tyr Ile Gly
1               5                   10                  15

Pro Ala Ser Gly Arg Pro Xaa Xaa Gln
            20                  25

<210> SEQ ID NO 450
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Asn Ser Gln Gln Gln Ile Arg Thr Leu Ser Gly
1               5                   10

<210> SEQ ID NO 451
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Asn Ser Ala Ala Ala Asp Phe Tyr Gln Gln Trp Leu Pro Ala His Gly
1               5                   10                  15

Pro Thr Ser Gly Arg Pro Pro Pro Pro
            20                  25

<210> SEQ ID NO 452
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Asn Ser Ala Ala Ala Asp Arg Tyr Glu Gln Trp Leu Arg Thr Cys Gly
1               5                   10                  15

Pro Leu Ser Gly Arg Pro Pro Pro Ser
            20                  25

<210> SEQ ID NO 453
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Asn Ser Ala Ala Ala Asp Pro Tyr Pro Gln Trp Leu Arg Arg Arg Gly
1               5                   10                  15

Pro Arg Ser Gly Arg Pro Pro Pro Arg
            20                  25

```
<210> SEQ ID NO 454
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(24)
<223> OTHER INFORMATION: Variable amino acid

<400> SEQUENCE: 454

Asn Ser Ala Ala Ala Asp Pro Tyr Ile Gln Trp Leu Arg His His Gly
1               5                   10                  15

Pro Leu Ser Gly Xaa Xaa Xaa Xaa Tyr
            20                  25

<210> SEQ ID NO 455
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Variable amino acid

<400> SEQUENCE: 455

Asn Ser Ala Ala Ala Asp Arg Tyr His Gln Trp Leu Pro Arg Arg Gly
1               5                   10                  15

Pro Ala Ser Gly Xaa Pro Pro Pro Arg
            20                  25

<210> SEQ ID NO 456
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Asn Ser Ala Ala Ala Asp Pro Tyr Asn Gln Trp Leu Leu Met His Gly
1               5                   10                  15

Pro Arg Ser Gly Arg Pro Ser Pro Pro Arg Asn
            20                  25

<210> SEQ ID NO 457
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Asn Ser Gln Gln Gln Ile Arg Thr Phe Ser Gly
1               5                   10

<210> SEQ ID NO 458
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 458

Asn Ser Gln Gln Gln Met Arg Thr Gly Ser Gly
1               5                   10

<210> SEQ ID NO 459
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Variable amino acid
<220> FEATURE:
<221> NAME/KEY: MOD_RES
<222> LOCATION: (25)..(25)
<223> OTHER INFORMATION: Variable amino acid

<400> SEQUENCE: 459

Asn Ser Ala Ala Ala Asp Pro Tyr Leu Gln Trp Leu His Arg Val Gly
1               5                   10                  15

Pro Xaa Ser Gly Arg Pro Pro Pro Xaa
            20                  25

<210> SEQ ID NO 460
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Asn Ser Ala Ala Ala Asp Pro Tyr Arg Gln Trp Leu Arg Arg Pro Gly
1               5                   10                  15

Pro Arg Ser Gly Arg Pro Pro Pro Arg
            20                  25

<210> SEQ ID NO 461
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Asn Ser Ala Ala Ala Asp Leu Tyr Leu Gln Trp Leu Ser Leu Tyr Gly
1               5                   10                  15

Pro Asp Ser Gly Arg Pro Pro Pro Thr
            20                  25

<210> SEQ ID NO 462
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Asn Ser Ala Ala Ala Asp Thr Tyr Ala Gln Trp Leu Arg Ala Trp Gly
```

```
                1               5                   10                  15

Pro Ser Ser Gly Arg Pro Pro Phe
            20                  25

<210> SEQ ID NO 463
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Asn Ser Gln Gln Gln Ile Val Thr Val Ser Gly
1               5                   10

<210> SEQ ID NO 464
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Variable amino acid

<400> SEQUENCE: 464

Asn Ser Ala Ala Ala Xaa Ser Tyr Ser Gln Trp Leu Arg Arg Gly Gly
1               5                   10                  15

Pro Ala Ser Gly Arg Pro Pro Pro Arg
            20                  25

<210> SEQ ID NO 465
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Variable amino acid
<220> FEATURE:
<221> NAME/KEY: MOD_RES
<222> LOCATION: (25)..(25)
<223> OTHER INFORMATION: Variable amino acid

<400> SEQUENCE: 465

Asn Ser Ala Ala Ala Asp Pro Tyr Phe Gln Trp Leu Leu Pro Leu Gly
1               5                   10                  15

Pro Ile Ser Gly Arg Xaa Pro Arg Xaa
            20                  25

<210> SEQ ID NO 466
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(24)
<223> OTHER INFORMATION: Variable amino acid

<400> SEQUENCE: 466
```

```
Asn Ser Ala Ala Ala Asp Lys Tyr Asp Gln Trp Leu Cys Tyr Ala Gly
1               5                   10                  15

Pro Arg Ser Gly Leu Xaa Xaa Xaa Trp
            20                  25
```

<210> SEQ ID NO 467
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Variable amino acid

<400> SEQUENCE: 467

```
Asn Ser Ala Ala Ala Asp Leu Tyr Phe Gln Trp Leu Ile Lys Val Gly
1               5                   10                  15

Pro Phe Ser Gly Leu Pro Gln Xaa Gly Leu
            20                  25
```

<210> SEQ ID NO 468
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Variable amino acid
<220> FEATURE:
<221> NAME/KEY: MOD_RES
<222> LOCATION: (24)..(24)
<223> OTHER INFORMATION: Variable amino acid

<400> SEQUENCE: 468

```
Asn Ser Gln Gln Gln Ile Arg Thr Arg Arg Leu Lys Arg Pro Gly Pro
1               5                   10                  15

Ser Ser Gly Arg Xaa Pro Gln Xaa
            20
```

<210> SEQ ID NO 469
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

```
Asn Ser Ala Ala Ala Asp Arg Tyr His Gln Trp Leu Arg Arg Arg Gly
1               5                   10                  15

Pro Arg Ser Gly Arg Pro Pro Arg
            20                  25
```

<210> SEQ ID NO 470
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 470

Asn Ser Gln Gln Gln Ile Ile Thr Ser Ser Gly
1               5                   10

<210> SEQ ID NO 471
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Asn Ser Ala Ala Ala Asp Pro Tyr Lys Gln Trp Leu Lys Arg Arg Gly
1               5                   10                  15

Pro Arg Ser Gly Arg Pro Pro Pro Pro
            20                  25

<210> SEQ ID NO 472
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Asn Ser Gln Gln Gln Met Gly Thr Val Ser Gly
1               5                   10

<210> SEQ ID NO 473
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Asn Ser Ala Ala Ala Asp His Tyr Leu Gln Trp Leu Asn Asn Leu Gly
1               5                   10                  15

Pro Glu Ser Gly Arg Pro Pro Pro Lys
            20                  25

<210> SEQ ID NO 474
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Asn Ser Ala Ala Ala Asp Trp Tyr Ser Gln Trp Leu Glu Ser Lys Gly
1               5                   10                  15

Pro Ala Ser Gly Arg Pro Pro Pro Asn
            20                  25

<210> SEQ ID NO 475
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 475

Asn Ser Ala Ala Ala Asp Asp Tyr Pro Gln Trp Leu Thr Arg Thr Gly
1               5                   10                  15

Pro Ser Ser Gly Arg Pro Pro Pro Thr
            20                  25

<210> SEQ ID NO 476
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Asn Ser Ala Ala Ala Asp Phe Tyr Thr Gln Trp Leu Ser Gly Pro Gly
1               5                   10                  15

Pro Thr Ser Gly Arg Pro Pro Pro Ser
            20                  25

<210> SEQ ID NO 477
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Asn Ser Ala Ala Ala Asp Lys Tyr Asp Gln Trp Leu Cys Tyr Ala Gly
1               5                   10                  15

Pro Arg Ser Gly Arg Pro Pro Pro Trp
            20                  25

<210> SEQ ID NO 478
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Asn Ser Ala Ala Ala Asp Leu Tyr Phe Gln Trp Leu Ile Lys Val Gly
1               5                   10                  15

Pro Phe Ser Gly Arg Pro Pro Pro Val
            20                  25

<210> SEQ ID NO 479
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Asn Ser Gln Gln Gln Ile Arg Thr Arg Arg Phe Lys Glu Ala Gly Ser
1               5                   10                  15

Phe Val Trp Ser Ser Pro Pro Leu
            20                  25

<210> SEQ ID NO 480
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Asn Ser Ala Ala Ala Asp Arg Tyr His Gln Trp Leu Arg Arg Arg Gly
1               5                   10                  15

Pro Arg Ser Gly Arg Pro Pro Pro Arg
            20                  25

<210> SEQ ID NO 481
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Asn Ser Gly Ala Ala Asp Arg Tyr Trp Gln Trp Leu Lys Pro Thr Gly
1               5                   10                  15

Pro Arg Ser Gly Arg Pro Pro Pro Arg
            20                  25

<210> SEQ ID NO 482
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Asn Ser Gln Gln Gln Ile Ile Thr Ser Ser Gly
1               5                   10

<210> SEQ ID NO 483
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Asn Ser Ala Ala Ala Asp Gly Tyr Ser Gln Trp Leu Ser Thr Gln Gly
1               5                   10                  15

Pro Trp Ser Gly Arg Pro Pro Pro Asp
            20                  25

<210> SEQ ID NO 484
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Asn Ser Ala Ala Ala Asp Pro Tyr Lys Gln Trp Leu Lys Arg Arg Gly
1               5                   10                  15

Pro Arg Ser Gly Arg Pro Pro Pro Arg
            20                  25
```

```
<210> SEQ ID NO 485
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Asn Ser Gln Gln Gln Met Gly Thr Val Ser Gly
1               5                   10

<210> SEQ ID NO 486
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Asn Ser Ala Ala Ala Asp His Tyr Leu Gln Trp Leu Asn Asn Leu Gly
1               5                   10                  15

Pro Glu Ser Gly Arg Pro Pro Pro Lys
            20                  25

<210> SEQ ID NO 487
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Asn Ser Ala Ala Ala Asp Trp Tyr Ser Gln Trp Leu Glu Ser Lys Gly
1               5                   10                  15

Pro Ala Ser Gly Arg Pro Pro Pro Asp
            20                  25

<210> SEQ ID NO 488
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Asn Ser Ala Ala Ala Asp Asp Tyr Pro Gln Trp Leu Thr Arg Thr Gly
1               5                   10                  15

Pro Ser Ser Gly Arg Pro Pro Pro Thr
            20                  25

<210> SEQ ID NO 489
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Variable amino acid

<400> SEQUENCE: 489
```

Asn Ser Ala Ala Ala Asp Pro Tyr Ala Gln Trp Leu Arg Ala Thr Gly
1               5                   10                  15

Pro Arg Ser Gly Xaa Pro Pro Arg
            20              25

<210> SEQ ID NO 490
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Asn Ser Ala Ala Ala Asp Gly Leu Arg Ser Val Val Thr
1               5                   10

<210> SEQ ID NO 491
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Asn Ser Ala Ala Ala Asp Phe Tyr Thr Gln Trp Leu Ser Gly Pro Gly
1               5                   10                  15

Pro Thr Ser Gly Arg Pro Pro Pro Ser
            20              25

<210> SEQ ID NO 492
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Asn Ser Ala Ala Ala Asp Arg Tyr Ala Gln Trp Leu Leu Thr Val Gly
1               5                   10                  15

Pro Ile Ser Gly Arg Pro Ser Pro Pro Val
            20              25

<210> SEQ ID NO 493
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Asn Ser Ala Ala Ala Asp Pro Tyr Arg Gln Trp Leu Pro Ala Arg Gly
1               5                   10                  15

Pro Arg Ser Gly Arg Pro Pro Pro Arg
            20              25

<210> SEQ ID NO 494
<211> LENGTH: 25
<212> TYPE: PRT
<213> ORGANISM: Artificial Sequence
<220> FEATURE:
<223> OTHER INFORMATION: Description of Artificial Sequence: Synthetic

```
                    peptide

<400> SEQUENCE: 494

Asn Ser Ala Ala Ala Asp Tyr Tyr His Gln Trp Leu Lys Ala Ala Gly
1               5                   10                  15

Pro Ser Ser Gly Arg Pro Pro Arg
            20                  25

<210> SEQ ID NO 495
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Asn Ser Ala Ala Ala Asp Lys Tyr Asp Gln Trp Leu Cys Tyr Ala Gly
1               5                   10                  15

Pro Arg Ser Gly Arg Pro Pro Pro Trp
            20                  25

<210> SEQ ID NO 496
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Asn Ser Ala Ala Ala Asp Leu Tyr Phe Gln Trp Leu Ile Lys Val Gly
1               5                   10                  15

Pro Phe Ser Gly Arg Pro Pro Pro Val
            20                  25

<210> SEQ ID NO 497
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Asn Ser Gln Gln Gln Ile Arg Thr Arg Arg Phe Lys Glu Ala Gly Ser
1               5                   10                  15

Phe Val Trp Ser Ser Pro Pro Leu
            20                  25

<210> SEQ ID NO 498
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Asn Ser Ala Ala Ala Asp Arg Tyr His Gln Trp Leu Arg Arg Arg Gly
1               5                   10                  15

Pro Arg Ser Gly Arg Pro Pro Pro Arg
            20                  25
```

```
<210> SEQ ID NO 499
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Asn Ser Gly Ala Ala Asp Arg Tyr Trp Gln Trp Leu Lys Pro Thr Gly
1               5                   10                  15

Pro Arg Ser Gly Arg Pro Pro Arg
            20                  25

<210> SEQ ID NO 500
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Asn Ser Gln Gln Gln Ile Ile Thr Ser Ser Gly
1               5                   10

<210> SEQ ID NO 501
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Asn Ser Ala Ala Ala Asp Gly Tyr Ser Gln Trp Leu Ser Thr Gln Gly
1               5                   10                  15

Pro Trp Ser Gly Arg Pro Pro Asp
            20                  25

<210> SEQ ID NO 502
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Asn Ser Ala Ala Ala Asp Pro Tyr Lys Gln Trp Leu Lys Arg Arg Gly
1               5                   10                  15

Pro Arg Ser Gly Arg Pro Pro Arg
            20                  25

<210> SEQ ID NO 503
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Asn Ser Gln Gln Gln Met Gly Thr Val Ser Gly
1               5                   10
```

<210> SEQ ID NO 504
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Asn Ser Ala Ala Ala Asp His Tyr Leu Gln Trp Leu Asn Asn Leu Gly
1               5                   10                  15

Pro Glu Ser Gly Arg Pro Pro Pro Lys
            20                  25

<210> SEQ ID NO 505
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Asn Ser Ala Ala Ala Asp Trp Tyr Ser Gln Trp Leu Glu Ser Lys Gly
1               5                   10                  15

Pro Ala Ser Gly Arg Pro Pro Pro Asp
            20                  25

<210> SEQ ID NO 506
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Asn Ser Ala Ala Ala Asp Asp Tyr Pro Gln Trp Leu Thr Arg Thr Gly
1               5                   10                  15

Pro Ser Ser Gly Arg Pro Pro Pro Thr
            20                  25

<210> SEQ ID NO 507
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Variable amino acid

<400> SEQUENCE: 507

Asn Ser Ala Ala Ala Asp Pro Tyr Ala Gln Trp Leu Arg Ala Thr Gly
1               5                   10                  15

Pro Arg Ser Gly Xaa Pro Pro Pro Arg
            20                  25

<210> SEQ ID NO 508
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 508

Asn Ser Ala Ala Ala Asp Gly Leu Arg Ser Val Val Thr
1               5                   10

<210> SEQ ID NO 509
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Asn Ser Ala Ala Ala Asp Phe Tyr Thr Gln Trp Leu Ser Gly Pro Gly
1               5                   10                  15

Pro Thr Ser Gly Arg Pro Pro Pro Ser
            20                  25

<210> SEQ ID NO 510
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Asn Ser Ala Ala Ala Asp Arg Tyr Ala Gln Trp Leu Leu Thr Val Gly
1               5                   10                  15

Pro Ile Ser Gly Arg Pro Ser Pro Pro Val
            20                  25

<210> SEQ ID NO 511
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Asn Ser Ala Ala Ala Asp Pro Tyr Arg Gln Trp Leu Pro Ala Arg Gly
1               5                   10                  15

Pro Arg Ser Gly Arg Pro Pro Pro Arg
            20                  25

<210> SEQ ID NO 512
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Asn Ser Ala Ala Ala Asp Tyr Tyr His Gln Trp Leu Lys Ala Ala Gly
1               5                   10                  15

Pro Ser Ser Gly Arg Pro Pro Pro Arg
            20                  25

<210> SEQ ID NO 513
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Variable amino acid

<400> SEQUENCE: 513

Asn Ser Ala Ala Ala Asp Arg Tyr His Gln Trp Leu Pro Arg Arg Gly
1               5                   10                  15

Pro Ala Ser Xaa Arg Pro Pro Pro Arg
            20                  25

<210> SEQ ID NO 514
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Asn Ser Ala Ala Ala Asp Trp Tyr Ser Gln Trp Leu Leu Arg Thr Gly
1               5                   10                  15

Pro Arg Ser Gly Arg Pro Pro Pro Val
            20                  25

<210> SEQ ID NO 515
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Asn Ser Ala Ala Ala Asp Gln Tyr Ala Gln Trp Leu Ser Arg Leu Gly
1               5                   10                  15

Pro Leu Ser Gly Arg Pro Pro Pro Thr
            20                  25

<210> SEQ ID NO 516
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Asn Ser Ala Ala Ala Asp Arg Tyr Ile Gln Trp Leu Ala Thr Ser Gly
1               5                   10                  15

Pro Leu Ser Gly Arg Pro Pro Pro Arg
            20                  25

<210> SEQ ID NO 517
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Asn Ser Ala Ala Ala Asp Gln Tyr Pro Gln Trp Leu Pro Leu Ala Gly
```

```
1               5                   10                  15

Pro His Ser Gly Arg Pro Pro Pro Lys
            20                  25

<210> SEQ ID NO 518
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Asn Ser Gln Gln Gln Ile Leu Thr Val Ser Gly
1               5                   10

<210> SEQ ID NO 519
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Asn Ser Ala Ala Ala Asp Arg Tyr His Gln Trp Leu Pro Arg Arg Gly
1               5                   10                  15

Pro Ala Ser Gly Arg Pro Pro Pro Arg
            20                  25

<210> SEQ ID NO 520
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Asn Ser Ala Ala Ala Asp Pro Tyr Ser Gln Trp Leu Gln Thr Pro Gly
1               5                   10                  15

Pro Thr Ser Gly Arg Pro Pro Pro Gln Val
            20                  25

<210> SEQ ID NO 521
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Asn Ser Ala Ala Ala Asp Ser Tyr Pro Gln Trp Leu Ser Thr Thr Gly
1               5                   10                  15

Pro Arg Ser Gly Arg Pro Pro Pro Val
            20                  25

<210> SEQ ID NO 522
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 522

Asn Ser Ala Ala Ala Asp Leu Tyr Trp Gln Trp Leu Ser Met Pro Gly
1               5                   10                  15

Pro Leu Ser Gly Arg Pro Pro Ile
            20                  25

<210> SEQ ID NO 523
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Asn Ser Gln Gln Gln Ile Phe Thr Leu Ser Gly
1               5                   10

<210> SEQ ID NO 524
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Asn Ser Gln Gln Gln Ile Arg Thr Arg Ser Gly Tyr Arg Arg Met Gly
1               5                   10                  15

Pro Arg Ser Gly Arg Pro Pro Arg
            20                  25

<210> SEQ ID NO 525
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Asn Ser Ala Ala Ala Asp Leu Tyr Met Gln Trp Leu Ala Val Met Gly
1               5                   10                  15

Pro Asp Ser Gly Arg Pro Pro Leu
            20                  25

<210> SEQ ID NO 526
<211> LENGTH: 63
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Asn Ser Ala Ala Ala Asp Gly Tyr Arg Gln Trp Leu Pro Pro Ala Gly
1               5                   10                  15

Pro Lys Ser Gly Arg Pro Pro Tyr Gln Ala Cys Arg Arg Ala Pro
            20                  25                  30

Gly Ile Ser Leu Gln Glu Asn Ser Ala Ala Ala Asp Arg Tyr Tyr Gln
        35                  40                  45

Trp Leu Leu Val Val Gly Pro Val Ser Gly Arg Pro Pro Ile
    50                  55                  60
```

<210> SEQ ID NO 527
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Asn Ser Ala Ala Ala Asp Pro Tyr His Gln Trp Leu Arg Thr Phe Gly
1               5                   10                  15

Pro Tyr Ser Gly Arg Pro Pro Pro Arg
            20                  25

<210> SEQ ID NO 528
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Asn Ser Ala Ala Ala Asp Ser Tyr Arg Gln Trp Leu Asn Lys Thr Gly
1               5                   10                  15

Pro Ile Ser Gly Arg Pro Pro Pro Leu
            20                  25

<210> SEQ ID NO 529
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Asn Ser Gly Ala Ala Asp Arg Tyr Trp Gln Trp Leu Lys Pro Thr Gly
1               5                   10                  15

Pro Arg Ser Gly Arg Pro Pro Pro Arg
            20                  25

<210> SEQ ID NO 530
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Asn Leu Tyr Ile Gln Trp Leu Lys Asp Gly Gly Pro Ser Ser Gly Arg
1               5                   10                  15

Pro Pro Pro Ser
            20

<210> SEQ ID NO 531
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)

```
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (12)..(14)
<223> OTHER INFORMATION: Variable amino acid
<220> FEATURE:
<221> NAME/KEY: MOD_RES
<222> LOCATION: (17)..(17)
<223> OTHER INFORMATION: Variable amino acid
<220> FEATURE:
<221> NAME/KEY: MOD_RES
<222> LOCATION: (24)..(24)
<223> OTHER INFORMATION: Variable amino acid

<400> SEQUENCE: 531

Asn Ala Ala Ala Asp Xaa Tyr Xaa Gln Trp Leu Xaa Xaa Xaa Gly Pro
1               5                   10                  15

Xaa Ser Gly Arg Pro Pro Xaa
            20

<210> SEQ ID NO 532
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Ser Ile Gly Tyr Leu Pro Leu
1               5

<210> SEQ ID NO 533
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Leu Thr Ala Glu Leu Thr Pro
1               5

<210> SEQ ID NO 534
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Ile Gln Trp Leu Lys Asp Gly Gly Pro Ser Ser Gly Arg Pro Pro Pro
1               5                   10                  15

Ser

<210> SEQ ID NO 535
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 535

Asn Leu Tyr Ile Gln
1               5

<210> SEQ ID NO 536
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Leu Arg Ala Leu Cys Gln Thr
1               5

<210> SEQ ID NO 537
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

His Arg Leu Gly Leu Gly Cys
1               5

<210> SEQ ID NO 538
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Lys Thr Ser Ile Ala Gln Gln
1               5

<210> SEQ ID NO 539
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Leu Asn Thr His Ser Arg Asn
1               5

<210> SEQ ID NO 540
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Ala Met Arg Tyr His Phe
1               5

<210> SEQ ID NO 541
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 541

Asp Arg Tyr Pro Gln Trp Leu Asn Gly Met Gly Pro Ser Ser Gly Arg
1               5                   10                  15

Pro Pro Pro Asn
            20

<210> SEQ ID NO 542
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Asp Ala Tyr Pro Gln Trp Leu Phe Thr Pro Gly Pro Thr Ser Gly Arg
1               5                   10                  15

Pro Pro Pro Leu
            20

<210> SEQ ID NO 543
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Asp Pro Tyr Ala Gln Trp Leu Gln Ser Met Gly Pro His Ser Gly Arg
1               5                   10                  15

Pro Pro Pro Arg
            20

<210> SEQ ID NO 544
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Asp Met Tyr Ala Gln Trp Leu Asp Asn Met Gly Pro His Ser Gly Arg
1               5                   10                  15

Pro Pro Pro Tyr
            20

<210> SEQ ID NO 545
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Asp Ala Tyr Ser Gln Trp Leu Leu Gln Thr Gly Pro Tyr Ser Gly Arg
1               5                   10                  15

Pro Ser Pro Arg Val
```

```
                    20

<210> SEQ ID NO 546
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Asp Thr Tyr Ile Gln Trp Leu Lys Ile Asn Gly Pro Arg Leu Val Val
1               5                   10                  15

Leu Pro Pro Arg Asn
            20

<210> SEQ ID NO 547
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Asp Ala Tyr Gly Gln Trp Leu Arg Thr Ser Gly Pro Leu Ser Gly Arg
1               5                   10                  15

Ser Leu Pro Pro Arg
            20

<210> SEQ ID NO 548
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Asp Trp Tyr Gln Gln Trp Leu Pro Pro Gly Gly Pro Gly Ser Gly Arg
1               5                   10                  15

Pro Pro Pro His Leu
            20

<210> SEQ ID NO 549
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Asp Leu Tyr Leu Gln Trp Leu Asp
1               5

<210> SEQ ID NO 550
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Tyr Thr Gln Trp Leu Tyr Leu Gln Gly Pro Asn Ser Gly Arg Pro Pro
```

```
1               5                   10                  15
Pro Tyr

<210> SEQ ID NO 551
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Ala Ala Ala Asp Pro Tyr Ala Gln Trp Leu Gln Ser Met Gly Pro His
1               5                   10                  15

Ser Gly Arg Pro Pro Pro Arg
            20

<210> SEQ ID NO 552
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
            20                  25                  30

Val Leu Lys Gln
        35

<210> SEQ ID NO 553
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Leu Lys Asp Gly Gly Pro Ser Ser Gly Arg Pro Pro Pro Ser
1               5                   10

<210> SEQ ID NO 554
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Met Leu Thr His Ser Pro
1               5

<210> SEQ ID NO 555
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555
```

```
Val Phe Met Val Leu Gly Leu Val Val Leu Pro Pro Leu
1               5                   10
```

<210> SEQ ID NO 556
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

```
Gln Trp Leu Leu Ser Cys Gly Pro Lys Ser Gly Arg Pro Pro Pro Asn
1               5                   10                  15
```

<210> SEQ ID NO 557
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

```
Gly Leu Gly Val Leu Cys Leu Val Val Leu Pro Pro Leu
1               5                   10
```

<210> SEQ ID NO 558
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

```
Arg Leu Met Val Leu Pro Ser Gly Arg Pro Pro Pro Ser
1               5                   10
```

<210> SEQ ID NO 559
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

```
Gly Pro Ala Ser Gly Arg Pro Pro Pro His Val
1               5                   10
```

<210> SEQ ID NO 560
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

```
Val Trp Ser Ser Ser Pro Pro Leu
1               5
```

<210> SEQ ID NO 561
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 561

Trp Cys Met Val Leu Ile Leu Val Val Leu Pro Pro Ile Asn
1               5                   10

<210> SEQ ID NO 562
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Cys Cys Arg Val Leu Phe Leu Val Val Leu Pro Pro Gly Asn
1               5                   10

<210> SEQ ID NO 563
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Trp Gly Leu Val Leu Arg Leu Val Val Leu Pro Pro Leu Asn
1               5                   10

<210> SEQ ID NO 564
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Gly Pro Leu Ser Gly Arg Pro Pro Pro Arg
1               5                   10

<210> SEQ ID NO 565
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Variable amino acid

<400> SEQUENCE: 565

Gln Trp Leu Arg Ala Ile Gly Pro Gly Ser Gly Xaa Pro Pro Pro Gln
1               5                   10                  15

<210> SEQ ID NO 566
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566
```

```
Gln Trp Leu Glu Ser Gln Gly Pro Leu Ser Gly Arg Pro Pro Lys
1               5                   10                  15

<210> SEQ ID NO 567
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Variable amino acid
<220> FEATURE:
<221> NAME/KEY: MOD_RES
<222> LOCATION: (17)..(17)
<223> OTHER INFORMATION: Variable amino acid

<400> SEQUENCE: 567

Tyr Thr Gln Trp Leu Trp Ser Arg Gly Pro Ala Ser Gly Arg Xaa Pro
1               5                   10                  15

Xaa Gly

<210> SEQ ID NO 568
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Variable amino acid
<220> FEATURE:
<221> NAME/KEY: MOD_RES
<222> LOCATION: (12)..(12)
<223> OTHER INFORMATION: Variable amino acid

<400> SEQUENCE: 568

Leu Leu Leu Val Leu Leu Leu Val Xaa Pro Gln Xaa Ile Asn
1               5                   10

<210> SEQ ID NO 569
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Tyr Leu Gln Trp Leu Ser Ser Thr Gly Pro Thr Ser Gly Arg Pro Pro
1               5                   10                  15

Pro Thr

<210> SEQ ID NO 570
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Ser Gly Leu Pro Pro Pro Glu
1               5
```

```
<210> SEQ ID NO 571
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Ala Gly Pro Leu Ser Gly Arg Pro Pro Pro His
1               5                   10

<210> SEQ ID NO 572
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Ile Leu Leu Val Leu Ser Leu Val Val Leu Pro Pro Leu Asn
1               5                   10

<210> SEQ ID NO 573
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(12)
<223> OTHER INFORMATION: Variable amino acid

<400> SEQUENCE: 573

Ile Arg Met Val Leu Ile Leu Val Xaa Xaa Xaa Xaa Ser Asn
1               5                   10

<210> SEQ ID NO 574
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Ser Gly Arg Pro Pro Pro Glu
1               5

<210> SEQ ID NO 575
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Ile Leu Leu Val Leu Ser Leu Val Val Leu Pro Pro Leu Asn
1               5                   10

<210> SEQ ID NO 576
<211> LENGTH: 14
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 576

Ile Arg Met Val Leu Ile Leu Val Val Leu Pro Pro Ser Asn
1               5                   10

<210> SEQ ID NO 577
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Tyr Leu Gln Trp Leu Ser Ser Thr Gly Pro Thr Ser Gly Arg Pro Pro
1               5                   10                  15

Pro Thr

<210> SEQ ID NO 578
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Ser Gly Arg Pro Pro Pro Glu
1               5

<210> SEQ ID NO 579
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Ala Gly Pro Leu Ser Gly Arg Pro Pro Pro His
1               5                   10

<210> SEQ ID NO 580
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Ser Gly Arg Pro Pro Pro Glu
1               5

<210> SEQ ID NO 581
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

-continued

```
Gln Ala Cys Arg Arg Ala Pro Gly Ile Ser Leu Gln Glu Asn Ser Ala
1               5                   10                  15

Ala Ala Asp Val Tyr Glu Gln Trp Leu Gln Ala Pro Gly Pro Arg Ser
            20                  25                  30

Gly Arg Pro Pro Val
        35
```

<210> SEQ ID NO 582
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

```
Ser Arg Leu Val Leu Gly Leu Val Val Leu Pro Pro Ile Asn
1               5                   10
```

<210> SEQ ID NO 583
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

```
Arg Ile Trp Val Leu Gly Leu Val Val Leu Pro Pro Leu
1               5                   10
```

<210> SEQ ID NO 584
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

```
Pro Leu Pro Val Pro Ile Cys Cys Cys Arg Ile Arg Gln Gln Gln Ile
1               5                   10                  15

Ile Thr Leu Ser Gly
            20
```

<210> SEQ ID NO 585
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

```
Leu Leu Leu Val Leu Leu Leu Val Val Leu Pro Pro Arg Asn
1               5                   10
```

<210> SEQ ID NO 586
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

```
Pro Gly Pro Ser Ser Gly Arg Pro Pro Leu Leu
1               5                   10

<210> SEQ ID NO 587
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Arg Leu Arg Val Leu Phe Leu Val Val Leu Pro Pro Ser Asn
1               5                   10

<210> SEQ ID NO 588
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Asn Leu
1

<210> SEQ ID NO 589
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Phe
1

<210> SEQ ID NO 590
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Val Thr Thr
1

<210> SEQ ID NO 591
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Trp Ser
1

<210> SEQ ID NO 592
<211> LENGTH: 3
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 592

Trp Pro Thr
1

<210> SEQ ID NO 593
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Asp Ser Phe
1

<210> SEQ ID NO 594
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Ser Val Pro
1

<210> SEQ ID NO 595
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Glu Trp Ser
1

<210> SEQ ID NO 596
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Asp
1
```